(12) United States Patent
Marinier et al.

(10) Patent No.: US 8,343,999 B2
(45) Date of Patent: *Jan. 1, 2013

(54) THIAZOLYL COMPOUNDS USEFUL AS KINASE INHIBITORS

(75) Inventors: Anne Marinier, Kirkland (CA); Marco Dodier, Wotton (CA); Stephan Roy, Levis (CA); Kurt Zimmermann, Durham, CT (US); Xiaopeng Sang, Glastonbury, CT (US); Mark D. Wittman, Wallingford, CT (US); David R. Langley, Meriden, CT (US); Ramkumar Rajamani, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 374 days.

This patent is subject to a terminal disclaimer.

(21) Appl. No.: 12/595,065

(22) PCT Filed: Apr. 9, 2008

(86) PCT No.: PCT/US2008/059735
§ 371 (c)(1),
(2), (4) Date: Jan. 11, 2010

(87) PCT Pub. No.: WO2008/124757
PCT Pub. Date: Oct. 16, 2008

(65) Prior Publication Data
US 2010/0120770 A1    May 13, 2010

Related U.S. Application Data

(60) Provisional application No. 60/910,841, filed on Apr. 10, 2007.

(51) Int. Cl.
*A61K 31/4427* (2006.01)
*C07D 417/14* (2006.01)

(52) U.S. Cl. .................................. 514/318; 546/193
(58) Field of Classification Search .............. 514/318; 546/193
See application file for complete search history.

(56) References Cited

U.S. PATENT DOCUMENTS
2003/0100567 A1    5/2003    Bilodeau et al.
2010/0048581 A1*   2/2010    Marinier et al. ......... 514/252.18

FOREIGN PATENT DOCUMENTS
| WO | WO 02/50071 | 6/2002 |
| WO | WO 2006/078621 | 7/2006 |
| WO | 2008/079873 | * 7/2009 |

OTHER PUBLICATIONS

Jagabandhu et al., Discovery and SAR of 2-amino-5-(thioaryl)thiazoles as potent and selective Itk inhibitors, Bioorganic and Medicinal Chemistry Letters, vol. 16, No. 14, pp. 3706-3712 (2006).

* cited by examiner

*Primary Examiner* — Celia Chang
(74) *Attorney, Agent, or Firm* — Elliott Korsen

(57) ABSTRACT

The invention provides compounds of formula I

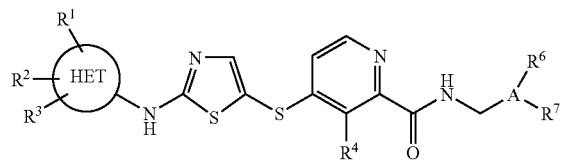

and pharmaceutically acceptable salts thereof.
The formula I thiazolyl compounds inhibit tyrosine kinase activity thereby making them useful as anticancer agents and for the treatment of Alzheimer's disease.

4 Claims, No Drawings

THIAZOLYL COMPOUNDS USEFUL AS KINASE INHIBITORS

FIELD OF THE INVENTION

The invention relates to novel thiazolyl compounds that are useful as anti-cancer agents. This invention also relates to pharmaceutical compositions containing the compounds and methods of using the compounds for the treatment of proliferative and other diseases, in particular, certain types of cancer.

BACKGROUND OF THE INVENTION

The invention relates to thiazolyl compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, Alzheimer's disease, angiogenic diseases and immunologic disorders (Powis, G.; Workman P. Signaling Targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Tyrosine kinases play a critical role in signal transduction for several cellular functions including cell proliferation, carcinogenesis, apoptosis, and cell differentiation. Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Ab1, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes.

It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and (h) factors that improve manufacturing costs or feasibility.

SUMMARY OF THE INVENTION

The invention provides compounds of Formula I, including stereoisomers, tautomers and pharmaceutically acceptable salts thereof, which are useful as inhibitors of tyrosine kinase enzymes.

The invention also provides pharmaceutical compositions comprising a pharmaceutically acceptable carrier and one or more of the compounds of the present invention or a stereoisomer, tautomer or pharmaceutically acceptable salt thereof. The invention also provides a method for treating a condition associated with one or more tyrosine kinase inhibitors comprising administering to a patient in need of such treatment, a therapeutically effective amount of a compound of formula I or a stereoisomer, tautomer or pharmaceutically acceptable salt thereof, and optionally one or more other anticancer agent or treatment.

The invention also provides methods for treating cancer using the compounds of the invention or a stereoisomer, tautomer or pharmaceutically acceptable salt thereof.

The invention also provides the compounds of the present invention or a stereoisomer, tautomer or pharmaceutically acceptable salt thereof, for use in therapy. The present invention also provides the use of the compounds of the present invention or a stereoisomer, tautomer or pharmaceutically acceptable salt thereof, for the manufacture of a medicament for the treatment of a proliferative disease such as cancer.

These and other features of the invention will be set forth in the expanded form as the disclosure continues.

DETAILED DESCRIPTION OF THE INVENTION

The invention provides for novel thiazolyl compounds useful as anti-cancer agents, pharmaceutical compositions employing such novel compounds and for methods of using such compounds.

In accordance with the invention, there are disclosed compounds of formula I

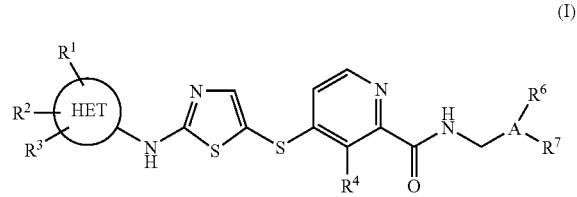

(I)

or a pharmaceutically acceptable salt or a stereoisomer thereof, wherein:

HET is a heteroaryl or heterocyclyl group;

A is a cycloalkyl or heterocyclyl group;

$R^1$, $R^2$ and $R^3$ are independently selected from the group consisting of hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl and alkylcarbonyl, or $R^1$ and $R^2$ or $R^2$ and $R^3$ can be taken together to form an optionally substituted carbocyclic or heterocyclic ring;

$R^4$ is hydrogen, alkyl, substituted alkyl, hydroxy, cyano or halogen;

$R^6$ and $R^7$ are independently selected from the group consisting of hydrogen, alkyl, substituted alkyl, aryl, substituted aryl, alkylidene, substituted alkylidene, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, cyanoalkyl, sulfonamide, substituted sulfonamide, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, heteroalkyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, alkylaminocarbonyl, —COOalkyl, —COaminoalkyl, —COalkyl, —COcycloalkyl, —COheteroaryl and —CO substituted heteroaryl.

In another aspect of the invention, there are disclosed compounds of formula II

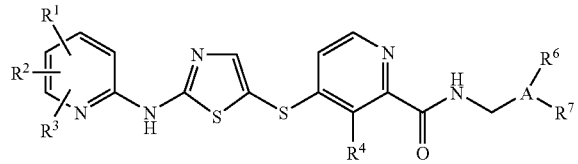

or a pharmaceutically acceptable salt or a stereoisomer thereof, wherein:

A is a cycloalkyl or heterocyclyl group;

$R^1$, $R^2$ and $R^3$ are independently selected from the group consisting of hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl, alkylcarbonyl, or $R^1$ and $R^2$ or $R^2$ and $R^3$ can be taken together to form an optionally substituted carbocyclic or heterocyclic ring;

$R^4$ is hydrogen, alkyl, substituted alkyl, hydroxy, cyano or halogen;

$R^6$ and $R^7$ are independently selected from the group consisting of hydrogen, alkyl, substituted alkyl, aryl, substituted aryl, alkylidene, substituted alkylidene, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, cyanoalkyl, sulfonamide, substituted sulfonamide, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, heteroalkyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, alkylaminocarbonyl, —COOalkyl, —COaminoalkyl, —COalkyl, —COcycloalkyl, —COheteroaryl and —CO substituted heteroaryl.

In another aspect of the invention, there are disclosed compounds of formula III

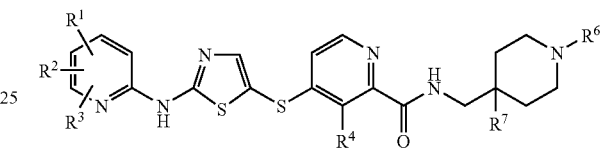

or a pharmaceutically acceptable salt or a stereoisomer thereof, wherein:

$R^1$, $R^2$ and $R^3$ are independently selected from the group consisting of hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, nitro, carboxy, alkoxycarbonyl, alkylcarbonyloxy, carbamoyl, substituted carbamoyl, alkenyl, substituted alkenyl, alkynyl, substituted alkynyl, alkylcarbonyl, or $R^1$ and $R^2$ or $R^2$ and $R^3$ can be taken together to form an optionally substituted carbocyclic or heterocyclic ring;

$R^4$ is hydrogen, alkyl, substituted alkyl, hydroxy, cyano or halogen;

$R^6$ and $R^7$ are independently selected from the group consisting of hydrogen, alkyl, substituted alkyl, aryl, substituted aryl, alkylidene, substituted alkylidene, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, cyanoalkyl, sulfonamide, substituted sulfonamide, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, heteroalkyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, alkylaminocarbonyl, —COOalkyl, —COaminoalkyl, —COalkyl, —COcycloalkyl, —COheteroaryl and —CO substituted heteroaryl.

In another aspect of the invention, there are disclosed compounds of formula IV

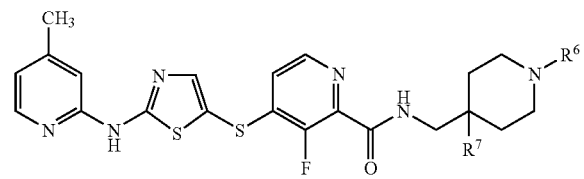

(IV)

or a pharmaceutically acceptable salt or a stereoisomer thereof, wherein:

$R^6$ and $R^7$ are independently selected from the group consisting of hydrogen, alkyl, substituted alkyl, aryl, substituted aryl, alkylidene, substituted alkylidene, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, cyanoalkyl, sulfonamide, substituted sulfonamide, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, heteroalkyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, alkylaminocarbonyl, —COOalkyl, —COaminoalkyl, —COalkyl, —COcycloalkyl, —COheteroaryl and —CO substituted heteroaryl.

Representative $R^6$ of the invention include hydrogen, alkyl, hydroxyalkyl, arylalkyl, —COOalkyl, —COaminoalkyl, —COalkyl, —COcycloalkyl, —COheterocyclyl and —CO substituted heterocyclyl.

Representative compounds of the invention include the following:

Tert-butyl 4-((3-fluoro-4-(2-(4-methylpyridin-2-ylamino)thiazol-5-ylthio)picolinamido)methyl)-4-phenylpiperidine-1-carboxylate, 3-Fluoro-N-((1-methyl-4-phenylpiperidin-4-yl)methyl)-4-(2-(4-methylpyridin-2-ylamino)thiazol-5-ylthio)picolinamide, 3-Fluoro-N-((1-(2-hydroxyethyl)-4-phenylpiperidin-4-yl)methyl)-4-(2-(4-methylpyridin-2-ylamino)thiazol-5-ylthio)picolinamide, 3-Fluoro-N-((1-methyl-4-(pyridin-4-yl)piperidin-4-yl)methyl)-4-(2-(4-methylpyridin-2-ylamino)thiazol-5-ylthio)picolinamide, N-((1-(2-(dimethylamino)acetyl)-4-phenylpiperidin-4-yl)methyl)-3-fluoro-4-(2-(4-methylpyridin-2-ylamino)thiazol-5-ylthio)picolinamide, 3-Fluoro-4-(2-(4-methylpyridin-2-ylamino)thiazol-5-ylthio)-N-((1-(methylsulfonyl)-4-phenylpiperidin-4-yl)methyl)picolinamide, 3-Fluoro-N-((1-(2-methoxyethyl)-4-phenylpiperidin-4-yl)methyl)-4-(2-(4-methylpyridin-2-ylamino)thiazol-5-ylthio)picolinamide, 3-Fluoro-N-((1-(2-hydroxy-2-methylpropyl)-4-phenylpiperidin-4-yl)methyl)-4-(2-(4-methylpyridin-2-ylamino)thiazol-5-ylthio)picolinamide 3-Fluoro-N-((1-(2-hydroxyethyl)-4-phenylpiperidin-4-yl)methyl)-4-(2-(5-((methylamino)methyl)pyridin-2-ylamino)thiazol-5-ylthio)picolinamide 3-fluoro-4-(2-(4-methylpyridin-2-ylamino)thiazol-5-ylthio)-N-((4-phenyltetrahydro-2H-pyran-4-yl)methyl)picolinamide, 3-fluoro-N-((1-(4-fluorophenyl)-4-hydroxycyclohexyl)methyl)-4-(2-(4-methylpyridin-2-ylamino)thiazol-5-ylthio)picolinamide (3-fluoro-4-(2-(4-methylpyridin-2-ylamino)thiazol-5-ylthio)pyridin-2-yl)(isoindolin-2-yl)methanone, N-((4-(2,3-dichlorophenyl)-1-methylpiperidin-4-yl)methyl)-3-fluoro-4-(2-(4-methylpyridin-2-ylamino)thiazol-5-ylthio)picolinamide, N-((4-cyclohexyl-1-methylpiperidin-4-yl)methyl)-3-fluoro-4-(2-(4-methylpyridin-2-ylamino)thiazol-5-ylthio)picolinamide 3-fluoro-N-((1-methyl-4-(5-methylisoxazol-3-yl)piperidin-4-yl)methyl)-4-(2-(4-methylpyridin-2-ylamino)thiazol-5-ylthio)picolinamide, 3-fluoro-N-((1-(2-hydroxyethyl)-4-(pyridin-3-yl)piperidin-4-yl)methyl)-4-(2-(4-methylpyridin-2-ylamino)thiazol-5-ylthio)picolinamide, methyl 4-((3-fluoro-4-(2-(4-methylpyridin-2-ylamino)thiazol-5-ylthio)picolinamido)methyl)-4-(pyridin-4-yl)piperidine-1-carboxylate, and (S)-3-amino-4-(4-((3-fluoro-4-(2-(4-methylpyridin-2-ylamino)thiazol-5-ylthio)picolinamido)methyl)-4-phenylpiperidin-1-yl)-4-oxobutanoic acid, or pharmaceutically acceptable salts thereof.

In another embodiment the present invention provides a pharmaceutical composition comprising a pharmaceutically acceptable carrier and one or more of the compounds of the present invention or a stereoisomer, tautomer or pharmaceutically acceptable salt thereof.

In another embodiment the present invention provides a pharmaceutical composition comprising a pharmaceutically acceptable carrier and a therapeutically effective amount of one or more of the compounds of the present invention or a stereoisomer, tautomer or pharmaceutically acceptable salt thereof.

In another embodiment the present invention provides a method for treating protein kinase related disorders comprising: administering to a patient in need of such treatment a therapeutically effective amount of one or more of the compounds of the present invention or a stereoisomer, tautomer or pharmaceutically acceptable salt thereof.

In another embodiment the present invention provides a method for treating tyrosine kinase related disorders comprising: administering to a patient in need of such treatment a therapeutically effective amount of one or more of the compounds of the present invention or a stereoisomer, tautomer or pharmaceutically acceptable salt thereof.

In another embodiment, the protein kinase related disorder is selected from the group consisting of cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

In another embodiment, the present invention provides a method of treating a patient in need of protein kinase related disorder treatment, comprising: administering a compound of the present invention or a stereoisomer, tautomer or pharmaceutically acceptable salt thereof in an amount effective to treat a protein kinase related disorder.

In another embodiment, the present invention provides a pharmaceutical composition further comprising one or more additional anticancer agent or treatment, such as radiation therapy.

In another embodiment, the present invention provides a compound of the present invention for use in therapy.

In another embodiment, the present invention provides a compound of the present invention for use in therapy for treating a protein kinase related disorder.

In another embodiment, the present invention provides a compound of the present invention for use in therapy for treating a tyrosine kinase related disorder.

In another embodiment, the present invention also provides the use of a compound of the present invention for the manufacture of a medicament for the treatment of a protein kinase related disorder.

In another embodiment, the present invention also provides the use of a compound of the present invention for the manufacture of a medicament for the treatment of a tyrosine kinase related disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a protein kinase related disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

The following are definitions of terms that may be used in the specification. The initial definition provided for a group or term herein applies to that group or term throughout the specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" or "alkylene" refers to both branched and straight-chain saturated aliphatic hydrocarbon groups of 1 to 20 carbon atoms, preferably 1 to 7 carbon atoms. The expression "lower alkyl" refers to unsubstituted alkyl groups of 1 to 4 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "alkenyl" or "alkenylene" refers to hydrocarbon chains of either a straight or branched configuration having the specified number of carbon atoms and one or more unsaturated carbon-carbon bonds which may occur in any stable point along the chain. These may be groups of 2 to 20 carbon atoms, preferably 2 to 15 carbon atoms, and most preferably 2 to 8 carbon atoms, having one to four double bonds. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" or "alkynylene" refers to hydrocarbon chains of either a straight or branched configuration and one or more carbon-carbon triple bonds which may occur in any stable point along the chain. These may include groups of 2 to 20 carbon atoms, preferably 2 to 15 carbon atoms, and most preferably 2 to 8 carbon atoms, having one to four triple bonds. Examples of alkynyl include, but are not limited to s ethynyl, propynyl, butynyl, pentynyl, hexynyl and the like.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "alkoxy" or "alkyloxy" refers to an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

The term "halogen" or "halo" refers to fluorine, chlorine, bromine and iodine.

The term "haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "carbocyclic ring" or "carbocyclyl" refers to stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl. When the term "carbocycle" is used, it is intended to include "aryl".

As used herein, the term "bicyclic carbocycle" or "bicyclic carbocyclic group" refers to a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like.

Heteroaryl groups can be substituted or unsubstituted.

Exemplary substituents include one or more alkyl or arylalkyl groups as described above or one or more groups described above as alkyl substituents.

The terms "heterocycle", "heterocyclic" and "heterocyclyl" refer to an optionally substituted, saturated, partially unsaturated or fully unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized to —NO—, —SO—, or —SO$_2$— and the nitrogen heteroatoms may also optionally be quaternized. The heterocyclic group may be attached at any heteroatom or carbon atom. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "heteroatoms" shall include oxygen, sulfur and nitrogen.

The term "alkylsulfone" refers to —$R^kS(=O)_2R^k$, wherein $R^k$ is an alkyl or substituted alkyl.

The term "oxo" refers to the divalent radical =O.

The term "carbamate" refers to the group —$OC(=O)NH_2$.

The term "amide" refers to the group —$C(=O)NH_2$.

The term "sulfonamide" refers to the group —$SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —$C(=O)NR'''R''$ wherein $R'''$ and $R''$ are independently selected from H, alkyl, substituted alkyl, alkenyl, substituted alkenyl, cycloalkyl, and substituted cycloalkyl, provided at least one of $R'''$ or $R''$ is a substituted moiety.

A substituted sulfonamide, for example, refers to the group —$SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group —$OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group —$NHC(=O)NH_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —$N(O)_2$.

The term "thio" refers to the group —SH.

The term "alkylthio" refers to the group —$SR^s$ where $R^s$ is an alkyl, substituted alkyl, cycloalkyl, or substituted cycloalkyl.

The term "thioalkyl" refers to the group —$R^tS$ where $R^t$ is an alkyl, substituted alkyl, cycloalkyl, or substituted cycloalkyl.

The term "alkylsulfonyl" refers to the group —$S(=O)_2R^u$ where $R^u$ is an alkyl, substituted alkyl, cycloalkyl, or substituted cycloalkyl.

The term "alkylsulfinyl" refers to the group —$S(=O)R^v$ where $R^v$ is an alkyl, substituted alkyl, cycloalkyl, or substituted cycloalkyl.

The term "carboxy" refers to the group —$C(=O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —$C(=O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —$OC(=O)R^x$, where $R^x$ is an alkyl or substituted alkyl, or an aryl or substituted aryl, respectively.

The term "carbamoyl" refers to the groups —$OC(=O)NH_2$, —$OC(=O)NHR^x$, and/or —$OC(=O)NR^yR^z$, wherein $R^y$ and $R^z$ are independently selected from alkyl and substituted alkyl.

The group —$NR^6(C=O)R^9$ refers to a group where $R^6$ is selected from hydrogen, lower alkyl and substituted lower alkyl, and $R^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a $C(=O)$.

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed according to methods known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the invention may be delivered in prodrug form. Thus, the invention is intended to cover prodrugs of the claimed compounds, methods of delivering the same and compositions containing the same. "Prodrugs" are intended to include any covalently bonded carriers that release an active parent drug of the invention in vivo when such prodrug is administered to a mammalian subject. Prodrugs of the invention are prepared by modifying functional groups present in the compound in such a way that the modifications are cleaved, either in routine manipulation or in vivo, to the parent compound. Prodrugs include compounds of the invention wherein a hydroxy, amino, or sulfhydryl group is bonded to any group that, when the prodrug of the invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the invention.

Various forms of prodrugs are well known in the art. For examples of such prodrug derivatives, see:

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice*, ed. F. D. King, The Royal Society of Chemistry, Cambridge, UK, 1994, which is incorporated herein by reference in its entirety.

It should further be understood that solvates (e.g., hydrates) of the compounds of formula I are also with the scope of the invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that these recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The invention further includes compositions comprising one or more compounds of the invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human, in need of such treatment which comprises administering to said animal an effective amount of a compound of formula I or a pharmaceutically acceptable salt thereof as defined herein before.

Further, another aspect of the invention provides for the use of a compound of formula I or a pharmaceutically acceptable salt thereof in the manufacture of a medicament for use in the treatment of certain types of cancer including cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®)

and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib (Sprycel®), Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*, 11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

If formulated as a fixed dose, a combination product can, for example, utilize a dosage of the compound of formula I within the dosage range described above and the dosage of another anti-cancer agent/treatment within the approved dosage range for such known anti-cancer agent/treatment. If a combination product is inappropriate, the compound of formula I and the other anti-cancer agent/treatment can, for example, be administered simultaneously or sequentially. If administered sequentially, the present invention is not limited to any particular sequence of administration. For example, compounds of formula I can be administered either prior to, or after, administration of the known anti-cancer agent or treatment.

The compounds may be administered in a dosage range of about 0.05 to 200 mg/kg/day, preferably less than 100 mg/kg/day, in a single dose or in 2 to 4 divided doses.

Biological Assays

A. CDK 2/cyclin E Kinase Assay

The assays were performed in U-bottom 384-well plates. The final assay volume was 30 µl prepared from 15 µl additions of enzyme and substrates (fluoresceinated CDK2E substrate peptide and ATP) and test compounds in assay buffer (100 mM HEPES pH 7.4, 10 mM $MgCl_2$, 0.015% Brij35 and 4 mM DTT). The reaction was initiated by the combination of bacterially expressed, CDK2E with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-peptide, 1.5 µM; CDK2E, 0.2 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

B. FLT3

The assays were performed in U-bottom 384-well plates. The final assay volume was 30 µl prepared from 15 µl additions of enzyme and substrates (fluoresceinated FLT3 substrate peptide and ATP) and test compounds in assay buffer (100 mM HEPES pH 7.4, 10 mM $MgCl_2$, 0.015% Brij35 and 4 mM DTT). The reaction was initiated by the combination of FLT3 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 200 µM, FL-peptide, 1.5 µM; FLT3, 4.5 nM and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

C. GSK3-β

The assays were performed in U-bottom 384-well plates. The final assay volume was 30 µl prepared from 15 µl additions of enzyme and substrates (fluoresceinated peptide FL-GSK substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of GSK3-β with substrates and test compounds. The reaction was incubated at room temperature for 60 min. and terminated by adding 30 µl of 35 mM EDTA to each sample. The reaction mixture was analyzed on the Caliper LabChip 3000 (Caliper, Hopkinton, Mass.) by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 30 µM; FL-GSK substrate, 1.5 µM; His-GSK3B, 2.4 nM; and DMSO, 1.6%.

D. IGF1-Receptor Tyrosine Kinase Assay

The assays were performed in U-bottom 384-well plates. The final assay volume was 30 µl prepared from 15 µl additions of enzyme and substrates (fluoresceinated IGF1R substrate peptide and ATP) and test compounds in assay buffer (100 mM HEPES pH 7.4, 10 mM $MnCl_2$, 0.015% Brij35 and 4 mM DTT). The reaction was initiated by the combination of IGF1-receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 µM; FL-peptide, 1.5 µM; IGF1-Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Compounds described herein were tested in the above assay. The following results were obtained.

| In vitro kinase data for IGF-1R | |
|---|---|
| Example # | IGF-1R IC50 (uM) |
| 2 | 0.009 |
| 5 | 0.003 |
| 11 | 0.004 |
| 12 | 0.006 |
| 18 | 0.001 |
| 22 | 0.003 |

-continued

In vitro kinase data for IGF-1R

| Example # | IGF-1R IC50 (uM) |
| --- | --- |
| 24 | 0.001 |
| 33 | 0.320 |
| 44 | 25.000 |
| 58 | 0.003 |
| 74 | 0.009 |
| 77 | 0.009 |
| 86 | 5.691 |
| 87 | 0.423 |
| 88 | 0.349 |
| 89 | 0.358 |
| 90 | 0.311 |
| 92 | 2.003 |
| 93 | 3.260 |
| 95 | 4.522 |

E. Insulin Receptor Tyrosine Kinase Assay

The assays were performed in U-bottom 384-well plates. The final assay volume was 30 µl prepared from 15 µl additions of enzyme and substrates (fluoresceinated InsR substrate peptide and ATP) and test compounds in assay buffer (100 mM HEPES pH 7.4, 10 mM MnCl$_2$, 0.015% Brij35 and 4 mM DTT). The reaction was initiated by the combination of Insulin Receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 µM; FL-peptide, 1.5 µM; Insulin Receptor, 14 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis

F. JAK2

The assays were performed in U-bottom 384-well plates. The final assay volume was 30 µl prepared from 15 µl additions of enzyme and substrates (fluoresceinated peptide FL-JAK2 substrate and ATP) and test compounds in assay buffer (100 mM HEPES pH 7.2, 10 mM MgCl$_2$, 0.015% Brij35, 25 mM β-glycerolphosphate and 4 mM DTT). The reaction was initiated by the combination of activated JAK2 with substrates and test compounds. The reaction was incubated at room temperature for 60 min. and terminated by adding 30 µl of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-JAK2 peptide, 1.5 µM; His-CDKS/p25, 2.6 nM; and DMSO, 1.6%.

G. LCK Kinase Assay

The assays were performed in U-bottom 384-well plates. The final assay volume was 30 µl prepared from 15 µl additions of enzyme and substrates (fluoresceinated LCK substrate peptide and ATP) and test compounds in assay buffer (100 mM HEPES pH 7.4, 10 mM MnCl$_2$, 0.015% Brij35 and 4 mM DTT). The reaction was initiated by the combination of LCK with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 3 µM; FL-peptide, 1.5 µM; Lck, 1 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

H. MapKapK2

The assays were performed in U-bottom 384-well plates. The final assay volume was 30 µl prepared from 15 µl additions of enzyme and substrates (fluoresceinated MK2 substrate peptide and ATP) and test compounds in assay buffer (100 mM HEPES pH 7.4, 10 mM MgCl$_2$, 0.015% Brij35 and 4 mM DTT). The reaction was initiated by the combination of MapKapK2 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 1 µM; FL-peptide, 1.5 µM; MapKapK2, 0.08 nM; Brij35, 0.015% and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

I. Met Kinase Assay

Kinase reactions consisted of 0.75 ng of baculovirus expressed GST-Met, 3 ug poly(Glu/Tyr) (Sigma), 0.12 µCi 33P γ-ATP, 1 µM ATP in 30 µl kinase buffer (20 mm TRIS-Cl, 5 mM MnCl$_2$, 0.1 mg/ml BSA, 0.5 mM DTT). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity (IC$_{50}$). Compounds were dissolved at 10 mM in dimethylsulfoxide (DMSO) and evaluated at seven concentrations, each in triplicate.

J. p38alpha Assay

The assays were performed in U-bottom 384-well plates. The final assay volume was 30 µl prepared from 15 µl additions of enzyme and substrates (fluoresceinated P38a substrate peptide and ATP) and test compounds in assay buffer (100 mM HEPES pH 7.2, 10 mM MgCl$_2$, 0.015% Brij35 and 4 mM DTT). The reaction was initiated by the combination of activated p38alpha with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38alpha, 6 nM; and DMSO, 1.6%.

K. p38beta Assay

The assays were performed in U-bottom 384-well plates. The final assay volume was 30 µl prepared from 15 µl additions of enzyme and substrates (fluoresceinated P38b substrate peptide and ATP) and test compounds in assay buffer (100 mM HEPES pH 7.2, 10 mM $MgCl_2$, 0.015% Brij35 and 4 mM DTT). The reaction was initiated by the combination of activated p38beta with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38beta, 1 nM; and DMSO, 1.6%.

L. Protein Kinase A

The assays were performed in U-bottom 384-well plates. The final assay volume was 30 µl prepared from 15 µl additions of enzyme and substrates (fluoresceinated PKA substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase A with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM, Protein kinase A 1 nM, and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

M. Protein Kinase C-alpha

The assays were performed in U-bottom 384-well plates. The final assay volume was 30 µl prepared from 15 µl additions of enzyme and substrates (fluoresceinated PKCa substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase C-alpha with lipids, substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 1 µM; FL-peptide, 1.5 µM; Protein kinase C-alpha, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

N. TrkA Kinase Assay

Kinase reactions consisted of 0.12 ng of baculovirus expressed His-TrkA, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

O. TrkB Kinase Assay

Kinase reactions consisted of 0.75 ng of baculovirus expressed His-TrkB, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

P. IGF-1R Sal Tumor Model

A salivary gland adenocarcinoma that developed spontaneously in a transgenic mouse (MCI-19) was excised and cut into fragments of about 20 mg. Tumor fragments were implanted s.c. into the ventral thoracic region of a group of six female, athymic BALB/c nu/nu mice (Harley Sprague-Dawley, Indianapolis, Ind.), using a 13-gauge trocar. Once established, the salivary gland-derived tumor line was designated IGF1R-Sal and was propagated as a tumor xenograft in nude mice. Tumors were passaged every 2 weeks, at which time the tumor reached f500 to 1,000 mm3 in size. For treatment studies, nude micebearing IGF1R-Sal tumors of about 100 mm3 in size were sorted into groups of five for treatment with vehicle (80% polyethylene glycol 400 in water) alone or the test article. Compounds were administered either on a bid schedule (oral doses 8 hours apart) or on a once a day schedule orally (qd) for 4 consecutive days. Tumors were measured at the start and end of treatment. Activity was measured as % tumor growth inhibition (% TGI). The % TGI was determined using the following formula $(C_t - T_t)/(C_t - C_o)$ where $C_t$ is defined as the median tumor size of the control group at the end of treatment, $C_o$ is defined as the median tumor size of the control group at the start of treatment, and $T_t$ is defined as the median tumor size of the treated group at the end of treatment.

Compounds described herein were tested in the above assay. The following results were obtained.

| In vivo data | | | |
|---|---|---|---|
| Example | % TGI | Dose (mg/kg) | Schedule |
| 2 | 107% | 12.5 | qd |
| 5 | 102% | 12.5 | qd |

-continued

In vivo data

| Example | % TGI | Dose (mg/kg) | Schedule |
|---------|-------|--------------|----------|
| 11 | 19% | 12.5 | qd |
| 12 | 92% | 12.5 | qd |
| 74 | 100% | 50 | qd |
| 77 | 114% | 25 | qd |

Methods of Preparation

In general, the compounds of formula I can be prepared in accordance with Scheme I and the general knowledge of one skilled in the art. Tautomers and solvates (e.g., hydrates) of the compounds of formula I are also within the scope of the invention. Methods of solvation are generally known in the art. Accordingly, the compounds of the instant invention can be in the free or hydrate form, and can be obtained by methods exemplified in Scheme I.

The substituted aminothiazole intermediates VI may be prepared via a palladium-catalyzed reaction with a bromo- or chloro-heterocycle or heteroaromatic and 2-aminothiazole. These Buchwald/Hartwig type reactions are well-known to those skilled in the art and are performed in toluene, THF or dioxane and involve a palladium catalyst such as tris(dibenzylideneacetone)dipalladium (0), tetrakis(triphenylphsophine)palladium (0), palladium (II) acetate and the like, a base such as sodium or potassium carbonate or phosphate and a ligand such as XANTPHOS (9,9-dimethyl-4,5-bis(diphenylphosphino)xanthene). The same type of palladium-coupling reaction may be done with an amino-heterocycle or heteroaromatic and 2-chloro or 2-bromothiazole to give the same desired aminothiazole intermediates VI. In another approach, the substituted aminothiazole intermediates VI may be prepared by the heat-promoted displacement of various chloro- or bromo-heterocycles or heteroaromatics.

These substituted aminothiazole intermediates VI may be then further substituted to the corresponding bromides VIIb or thiocyanates VIIa by reaction with bromine in chloroform or by treatment with bromine and sodium or potassium thiocyanate in methanol.

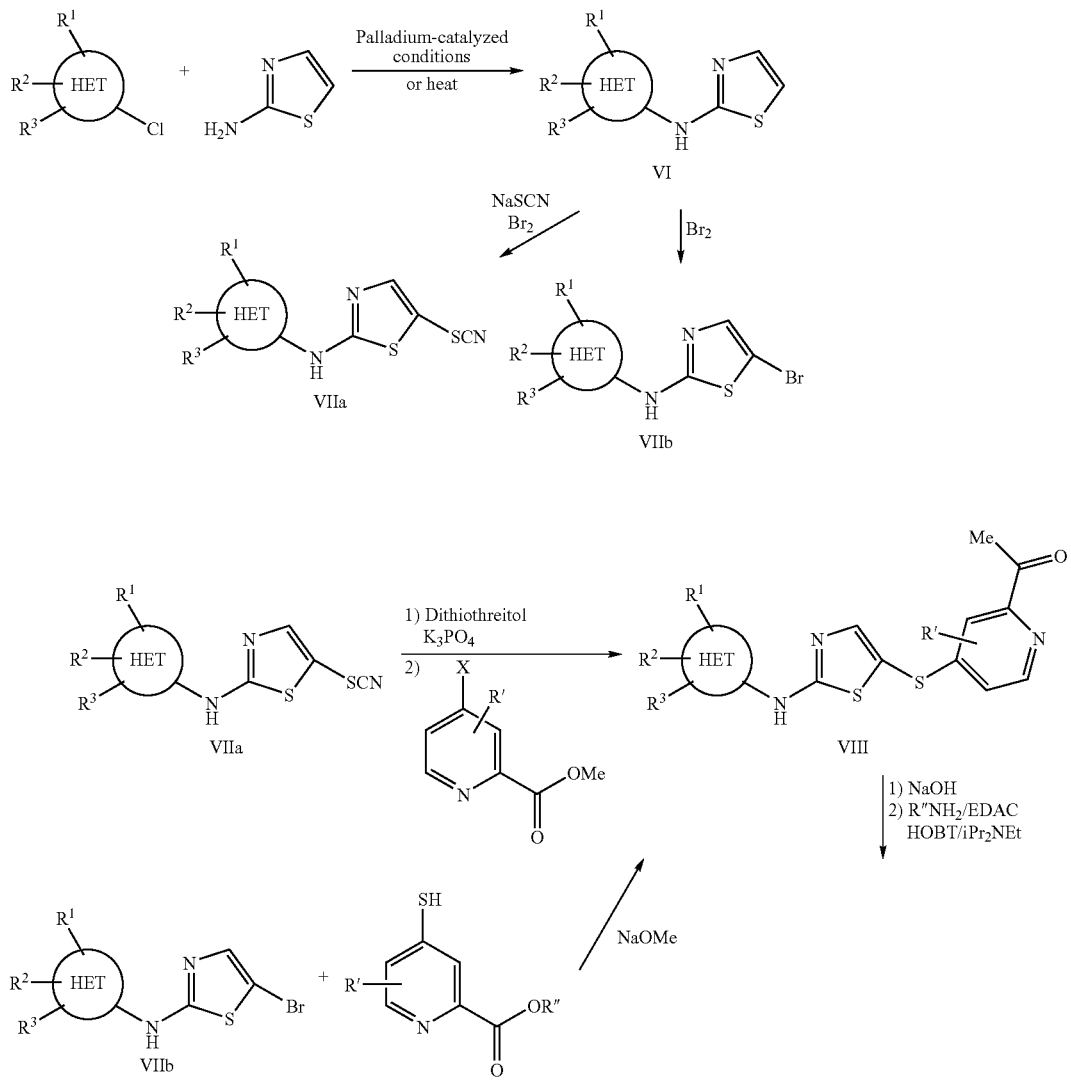

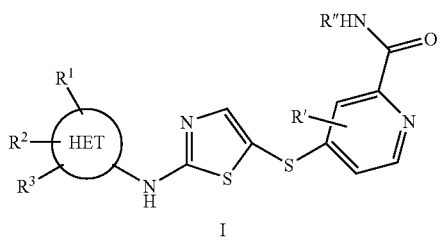

The bromides VIIb can then be substituted with various substituted thiopyridines bearing an ester or carboxylic acid in position 2 in presence of any number of organic bases such as sodium methoxide in methanol. In another approach, the thiocyanates VIIa may first react with dithiothreitol in methanol and then with various substituted halopyridines bearing an ester or carboxylic acid in position 2 in presence of a base such as sodium hydroxide or potassium phosphate. The resulting ester intermediates VIII may then be saponified to the corresponding acids and coupled with various amines in presence of any number of reagents known in the art for forming and catalyzing amide formation between amines and acids such as DCC, EDCI, EDAC (1-[3-dimethylaminopropyl]-3-ethyl carbodiimide hydrochloride), dimethylaminopyridine (DMAP), hydroxybenzotriazole (HOBT), and bases such as diisopropylethylamine, triethylamine and the like to afford the compounds of type I.

SCHEME II

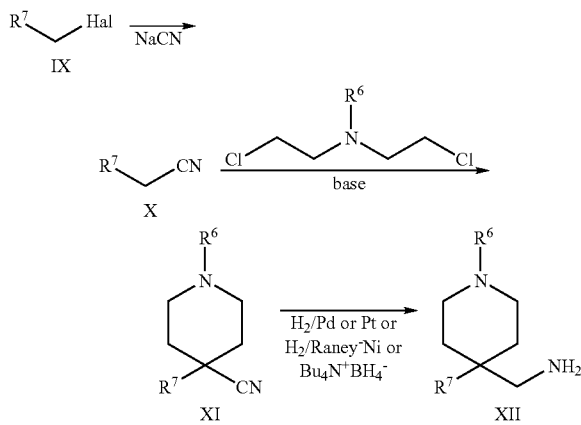

The substituted 4-aminomethyl-piperidines XII may be prepared as shown in Scheme II. Commercially available (optionally substituted) aryl- or heteroaryl-methylhalides IX may be treated with an inorganic cyanide, such as sodium cyanide, to give substituted acetonitriles X, which may be reacted with N-protected bis-(2-chloroethyl)amine and base to give piperidines XI. These may be reduced by transition metal catalyzed hydrogenation or hydride reagents to the corresponding methylamines XII.

Complete hydrogenation can be achieved under of number of conditions known in the art to convert the unsaturated ring into its saturated counterpart.

The invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

All temperatures are in degrees Celsius (° C.) unless indicated otherwise herein.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm)

The following abbreviations may be employed herein: n-BuOH: n-butyl alcohol, CDCl$_3$: Chloroform-d, D$_2$O: deuterium oxide, DCM: dichloromethane, DMA: dimethylamine, DMF: dimethyl formamide, DMSO™ dimethyl sulfoxide, EDC: 1,2-dichloroethane, EtOH: ethanol, EtOAc: ethyl acetate, HCl: hydrochloric acid, HOAc: acetic acid, IPA: isopropyl alcohol, K$_2$CO$_3$: potassium carbonate, MeOH: methanol, MgSO$_4$: magnesium sulfate, NaHCO$_3$: sodium bicarbonate, Na$_2$SO$_4$: sodium sulfate, NH$_4$Cl: ammonium chloride, NH$_3$: ammonia, N$_2$: nitrogen, POCl$_3$: phosphorous oxychloride, THF: tetrahydrofuran, TFA: trifluoroacetic acid, Bn: benzyl, Me: methyl, Et: ethyl, min.: minute(s), h or hr(s): hour(s), L: liter, mL: milliliter, μL: microliter, g: gram(s), mg: milligram(s), mol.: moles, mmol; millimole(s), meq.: milliequivalent, RT or rt: room temperature, ret. t.: HPLC retention time (minutes), sat or sat'd: saturated, aq.: aqueous, TLC: thin layer chromatography, HPLC: high performance liquid chromatography, RP HPLC: reverse phase HPLC, Prep HPLC: preparative reverse phase HPLC, LC/MS: high performance liquid chromatography/mass spectrometry, MS: mass spectrometry, NMR: nuclear magnetic resonance, and mp: melting point, XANTPHOS: 9,9-dimethyl-4,5-bis(diphenylphosphino)xanthene, MeCN: acetonitrile, DMF: N,N-dimethylformamide, EDAC: 1-[3-dimethylaminopropyl]-3-ethyl carbodiimide hydrochloride, HOBT: 1-hydroxybenzotriazole hydrate, TMSCN: trimethylsilyl cyanide, LAH: lithium aluminum hydride, MOMCl: methoxymethyl chloride HPLC Conditions A: Primesphere C18, 4.6×30 mm, 2 min. gradient, 0% B to 100% B, Solvant A: 10% MeCN-90% water-0.1% TFA, Solvant B: 90% MeCN-10% water-0.1% TFA, 4 mL/min., 220 nm.

B: Primesphere C18, 4.6×30 mm, 2 mM. gradient, 0% B to 100% B, Solvant A: 10% MeCN-90% water-5 mM NH$_4$OAc, Solvant B: 90% MeCN-10% water-5 mM NH$_4$OAc, 4 mL/min, 220 nm.

C: ZorbaxSB C18, 4.6×75 mm, 8 min. gradient, 0% B to 100% B, Solvant A:10% MeCN-90% water-0.1% TFA, Solvant B: 90% MeCN-10% water-0.1% TFA, 2.5 mL/min., 220 nm.

D: Luna 5u C18, 4.6×30 mm, 2 min. gradient, 0% B to 100% B, Solvant A: 10% MeCN-90% water-0.1% TFA, Solvant B: 90% MeCN-10% water-0.1% TFA, 4 mL/min., 220 nm.

E: Luna 5u C18, 4.6×30 mm, 2 min. gradient, 0% B to 100% B, Solvant A: 10% MeCN-90% water-5 mM NH₄OAc, Solvant B: 90% MeCN-10% water-5 mM NH₄OAc, 4 mL/min, 254 nm.

F: Luna 5u C18, 4.6×30 mm, 2 min. gradient, 0% B to 100% B, Solvant A: 10% MeCN-90% water-0.1% TFA, Solvant B: 90% MeCN-10% water-0.1% TFA, 4 mL/min., 254 nm.

G: Phenomenex C18 4.6×30 mm column, 2 min gradient, 0-100% B, then 1 min 100% B, 5 mL/min. 220 nm, Solvent A: 5% CH3CN-95% H2O-10 mM Ammonium Acetate; Solvent B: 95% CH3CN-5% H2O-10 mM Ammonium Acetate.

H: Waters Sunfire C18 4.6×150 mm, 3.5 um column, 10 min gradient, 0-100% B, then 5 min 100% B, 1 mL/min. 220 nm, Solvent A: 5% CH3CN-95% H2O-0.1% TFA; Solvent B: 95% CH3CN-5% H2O-0.1% TFA.

I: Phenomenex C18 4.6×30 mm column, 2 min gradient, 0-100% B, then 1 min 100% B, 5 mL/min. 220 nm, Solvent A: 10% CH3OH-90% H2O-0.1% TFA; Solvent B: 90% CH3OH-10% H2O-0.1% TFA;

J: Phenomenex C18 4.6×30 mm column, 3 min gradient, 0-100% B, then 1 min 100% B, 5 mL/min. 220 nm, Solvent A: 5% CH3CN-95% H2O-10 mM Ammonium Acetate; Solvent B: 95% CH3CN-5% H2O-10 mM Ammonium Acetate.

K: Waters Sunfire C18 4.6×150 mm, 3.5 um column, 20 min gradient, 0-100% B, then 5 min 100% B, 1 mL/min. 220 nm, Solvent A: 5% CH₃CN-95% H2O-0.1% TFA; Solvent B: 95% CH3CN-5% H2O-0.1% TFA.

L: Phenomenex C18 10 um, 3.0×50 mm column, 2 min gradient, 0-100% B, then 1 min 100% B, 5 mL/min. 220 nm, Solvent A: 10% CH₃OH-90% H2O-0.1% TFA; Solvent B: 90% CH₃OH-10% H2O-0.1% TFA;

M: Phenomenex 10 um 4.6×50 mm column, 2 min gradient, 0-100% B, then 1 min 100% B, 5 mL/min. 220 nm, Solvent A: 5% CH3CN-95% H2O-10 mM Ammonium Acetate; Solvent B: 95% CH3CN-5% H2O-10 mM Ammonium Acetate.

N: Phenomenex Gemini C18 4.6×150 mm 3.5 um column, 15 min gradient, 10-100% B, then 5 min 100% B, 1 mL/min. Solvent A: 5% CH3OH-95% H2O-10 mM Ammonium bicarbonate; Solvent B: 95% CH₃OH-5% H2O-10 mM Ammonium bicarbonate, 220 nm.

O: Waters Sunfire C18 4.6×150 mm, 3.5 um column, 10 min gradient, 10-100% B, then 5 min 100% B, 1 mL/min. Solvent A: 5% CH3CN-95% H2O-0.1% TFA; Solvent B: 95% CH₃CN-5% H2O-0.1% TFA, 220 nm.

P: Waters Sunfire C18 4.6×150 mm, 3.5 um column, 15 min gradient, 10-100% B, then 5 min 100% B, 1 mL/min. Solvent A: 5% CH3CN-95% H2O-0.1% TFA; Solvent B: 95% CH3CN-5% H2O-0.1% TFA, 220 nm.

Q: Waters Xbridge Phenyl column 4.6×150 mm 3.5 um, 10 min gradient, 0-100% B, 5 mL/min. Solvent A: 5% CH3CN-95% H2O-0.1% TFA; Solvent B: 95% CH3CN-5% H2O-0.1% TFA, 220 nm.

1. Preparation of the Intermediates

Synthesis of the Various Thiazoles

A) Synthesis of N-(thiazol-2-yl)pyridine-2-amine

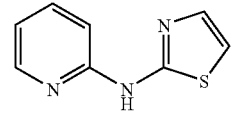 [SMILES: c1ccc(Nc2nccs2)nc1]

A suspension of 2-aminothiazole (7.35 g, 73.39 mmol), 2-chloropyridine (10.0 g, 88.07 mmol, 1.2 eq), sodium carbonate (10.98 g, 0.102 mol, 1.4 eq) and 9,9-dimethyl-4,5-bis (diphenylphosphino)xanthene (XANTPHOS) (0.509 g, 0.881 mmol, 0.012 eq) in toluene (160 mL, bubbled with argon for 5 minutes) was bubbled again with argon for 5 additional minutes. Tris(dibenzylideneacetone)dipalladium (0) (0.269 g, 0.293 mmol, 0.004 eq) was then added to the suspension which was heated at 140° C. for 4 days. The mixture was cooled to RT and filtered. The resulting solid was suspended in water and stirred for 2 hours, after which, filtration of the suspension gave a solid which was dried overnight under vacuum (10.329 g). The toluene filtrate was evaporated and the residue was triturated from methanol to give a solid (1.055 g). The two solids were combined and afforded the title compound (11.384 g, 87%). ¹H NMR (400 MHz, DMSO-d6) δ (ppm): 6.91 (1H, dd, J=7.1, 5.1 and 0.8 Hz), 7.00 (1H, d, J=3.5 Hz), 7.06 (1H, d, J=8.3 Hz), 7.38 (1H, d, J=3.5 Hz), 7.69 (1H, ddd, J=8.3, 7.1 and 1.8 Hz), 8.29 (1H, ddd, J=5.1, 1.8 and 0.8 Hz), 11.24 (1H, s). LC/MS (M+H)⁺: 178. HPLC ret. time (Condition A): 0.668 min.

B) Synthesis of 4-methyl-N-(thiazol-2-yl)pyridine-2-amine

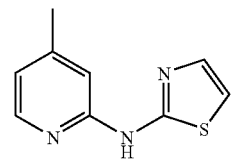

A suspension of 4-methyl-2-chloropyridine (5.10 g, 40.0 mmol), 2-aminothiazole (4.81 g, 48 mmol, 1.2 eq), sodium carbonate (5.94 g, 56.0 mmol, 1.4 eq) and XANTPHOS (0.278 g, 0.48 mmol, 0.012 eq) in THF (100 mL, bubbled with argon for 5 minutes) was bubbled again with argon for 5 additional minutes. Tris(dibenzylideneacetone)dipalladium (0) (0.146 g, 0.16 mmol, 0.004 eq) was then added to the suspension which was heated at 130° C. for 2 days. Additional quantities of XANTPHOS (0.278 g) and tris(dibenzylideneacetone)dipalladium (0) (0.146 g) were added again and the reaction was heated at 130° C. for 4 more days. The mixture was cooled to RT and filtered. The resulting solid was suspended in water and stirred for 1 hour. After filtration, the resulting solid was dried under vacuum overnight. The THF filtrate was evaporated and the residue was combined to the previously isolated solid. This was precipitated from MeOH to give the title compound (5.14 g, 67%) as a solid. The mother liquor was evaporated and the residue purified by silica gel chromatography (50% ethyl acetate/dichloromethane to 100% ethyl acetate) and afforded the title material (0.825 g, 11%) as a solid. $^1$H NMR (400 MHz, CDCl$_3$) δ (ppm): 2.36 (3H, s), 6.71 (1H, s), 6.75 (1H, br d, J=5.1 Hz), 6.84 (1H, d, J=3.5 Hz), 7.43 (1H, d, J=3.5 Hz), 8.24 (1H, d, J=5.3 Hz). LC/MS (M+H)$^+$: 192. HPLC ret. time (Condition A): 1.285 min.

C) Synthesis of tert-butyl(6-(thiazolyl-2-ylamino)pyridine-3-yl)methylcarbamate

1. Synthesis of tent-butyl(6-chloropyridin-3-yl)methylcarbamate

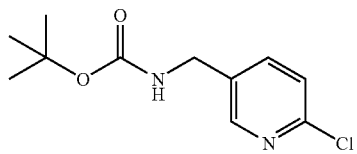 [SMILES: CC(C)(C)OC(=O)NCc1ccc(Cl)nc1]

A stirred solution of (6-chloropyridin-3-yl)methanamine (6.56 g, 46.01 mmol) in dichloromethane (50 mL) was treated with triethylamine (11.2 mL, 80.51 mmol, 1.75 eq) and di-tert-butyl-di-carbonate (12.55 g, 57.51 mmol, 1.25 eq) at room temperature and this mixture was stirred overnight. Aqueous saturated ammonium chloride was added to the mixture and the two phases were separated. The aqueous phase was extracted with dichloromethane (3×) and the combined organic layers were dried over anhydrous magnesium sulfated, filtered and concentrated to give the title material (12.17 g, >100%) as a solid. $^1$H NMR (400 MHz, CDCl$_3$) δ (ppm): 1.47 (9H, s), 4.33 (1H, d, J=6.1 Hz), 4.95 (1H, br s), 7.32 (1H, d, 8.0 Hz), 7.64 (1H, br dd, J=7.8 and 1.5 Hz), 8.33 (1H, d, J=2.0 Hz). Traces of Net$_3$HCl salt were detected by NMR. LC/MS (M+H)$^+$: 243. The compound was used as such for the next reaction.

2. Synthesis of tert-butyl(6-(thiazolyl-2-ylamino)pyridine-3-yl)methylcarbamate

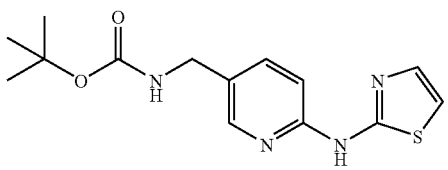 [SMILES: CC(C)(C)OC(=O)NCc1ccc(Nc2nccs2)nc1]

A suspension of tert-butyl(6-chloropyridin-3-yl)methylcarbamate (13.06 g, ~53.9 mmol, crude), 2-aminothiazole (8.10 g, 80.9 mmol, 1.5 eq), sodium carbonate (8.00 g, 75.5 mmol), XANTPHOS (0.374 g, 0.647 mmol, 0.012 eq) in THF (125 mL, bubbled with argon for 5 minutes) was bubbled again with argon for 5 additional minutes. Tris(dibenzylideneacetone)dipalladium (0) (0.198 g, 0.216 mmol, 0.004 eq) was then added to the suspension which was heated at 130° C. for 1 day. Additional quantities of XANTPHOS (0.374 g) and tris(dibenzylideneacetone)dipalladium (0) (0.198 g) were added again and the reaction was heated at 130° C. overnight. The mixture was cooled to RT and filtered. The resulting solid was suspended in water and stirred for 1 hour. After filtration, the resulting solid was dried under vacuum overnight. The THF filtrate was evaporated and the residue was triturated from methanol to give a solid. The solids were combined to give the title material (13.91 g, 84%). $^1$H NMR (400 MHz, DMSO-d6) δ (ppm): 1.39 (9H, s), 4.06 (1H, d, J=6.1 Hz), 6.99 (1H, d, J=3.5 Hz), 7.02 (1H, d, J=8.6 Hz), 7.37 (1H, d, J=3.5 Hz), 7.39 (1H, br s), 7.58 (1H, dd, J=8.6 and 2.0 Hz), 8.15 (1H, br d, J~1.8 Hz), 11.21 (1H, s). LC/MS (M+H)$^+$: 307. HPLC ret. time (Condition A): 1.247 min.

D) Synthesis of tert-butyl methyl((6-(thiazol-2-ylamino)pyridin-3-yl)methyl)carbamate

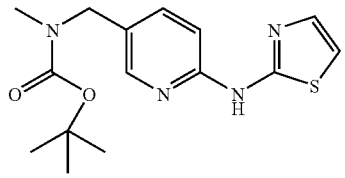 [SMILES: CN(Cc1ccc(Nc2nccs2)nc1)C(=O)OC(C)(C)C]

1. Synthesis of tert-butyl (6-chloropyridin-3-yl)methyl (methyl)carbamate

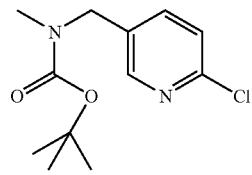 [SMILES: CN(Cc1ccc(Cl)nc1)C(=O)OC(C)(C)C]

A solution of tert-butyl(6-(thiazolyl-2-ylamino)pyridine-3-yl)methylcarbamate (1.52 g crude, ~6.28 mmol) in THF (10 mL) was treated with sodium hydride (60% in oil, 0.360 g, 9.42 mmol) at 0° C. The reaction was then stirred at 23° C. for 45 minutes, then iodomethane (0.47 mL, 7.53 mmol) was added and the reaction was stirred overnight. Sat. aq ammonium chloride was then added and the two phases were separated. The aqueous phase was extracted with ethyl acetate (3×) and the combined organic layers were dried over anhydrous magnesium sulfate, filtered and concentrated to give the crude title material (1.50 g). The residue was purified on Biotage (hexane/ethylacetate 3:1 to 1:3) and gave the title material (1.24 g, 77%). $^1$H NMR (400 MHz, CDCl$_3$) δ ppm: 1.50 (9H, s) 2.86 (2H, d, J=19.70 Hz) 4.42 (s, 3H) 7.33 (1H, d, J=8.08 Hz) 7.57 (1H, d, J=17.94 Hz) 8.30 (1H, d, J=1.77 Hz). LCMS (M+H)$^+$: 257, 259. HPLC ret. time (Conditions B): 1.743 min.

2. Synthesis of tert-butyl methyl((6-(thiazol-2-ylamino)pyridin-3-yl)methyl)carbamate

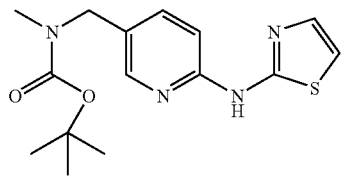 [SMILES: CN(Cc1ccc(Nc2nccs2)nc1)C(=O)OC(C)(C)C]

A suspension of 2-aminothiazole (0.556 g, 5.55 mmol, 1.15 eq), tert-butyl (6-chloropyridin-3-yl)methyl(methyl)carbamate (1.24 g, 4.83 mmol), sodium carbonate (0.717 g, 6.76 mol, 1.4 eq) and 9,9-dimethyl-4,5-bis(diphenylphosphino)xanthene (XANTPHOS) (0.034 g, 0.058 mmol, 0.012 eq) in THF (12 mL, bubbled with argon for 5 minutes) was bubbled again with argon for 5 additional minutes. Tris(dibenzyl ideneacetone)dipalladium (0) (0.018 g, 0.019 mmol, 0.004 eq) was then added to the suspension which was heated at 130° C. for 18 hours. Tris(dibenzylideneacetone)dipalladium (0) (0.018 g, 0.019 mmol, 0.004 eq) and 9,9-dimethyl-4,5-bis(diphenyl phosphino)xanthene (XANTPHOS) (0.034 g, 0.058 mmol, 0.012 eq) were added again and the reaction was stirred for 18 more hours. The same was repeated a second time. The mixture was cooled down to RT and filtered. The THF filtrate was evaporated and the residue (1.72 g) was purified on Biotage silica gel chromatography (hexane/ethyl acetate 1:1 to 0:1) to give the title material (0.934 g, 60%). $^1$H NMR (400 MHz, CDCl$_3$) δ ppm: 1.52 (9H, s), 2.84 (3H, s), 4.40 (2H, s), 6.86 (1H, d, J=3.54 Hz), 6.92 (1H, d, J=8.59 Hz), 7.44 (1, d, J=3.79 Hz), 7.57 (1H, d, J=19.45 Hz) 8.27 (1H, s).

Synthesis of the Various Bromides or Thiocyanates

A) Synthesis of 5-bromo-N-(pyridine-2-yl)thiazol-2-amine

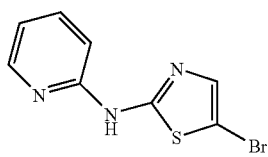 [SMILES: Brc1cnc(Nc2ccccn2)s1]

To a stirred suspension of N-(pyridin-2-yl)thiazol-2-amine (9.76 g, 55.07 mmol) in degassed chloroform (180 mL) was added bromine (3.11 mL, 60.6 mmol, 1.1 eq) at 23° C. The reaction was stirred for 15 minutes and followed by LC/MS. Bromine (2×0.3 mL) was added until reaction completed. The mixture was cooled to 0° C. and 10% aq. NaHSO$_3$ (150 mL) was added. The suspension changed color and the solid was filtered, washed with water and vacuum dried overnight. The title compound was obtained as a solid (10.79 g, 77%). $^1$H NMR (400 MHz, DMSO-d6) δ ppm 6.94-6.99 (1H, m), 7.04 (1H, d, J=8.34 Hz) 7.45 (1H, s), 7.74 (1 H, td, J=7.83, 1.77 Hz), 8.31 (1 H, d, J=5.31 Hz), 11.54 (1 H, s). LC/MS (M+H)$^+$: 256, 258; (M−H)$^−$: 254, 256.

B) Synthesis of 5-bromo-N-(4-methyl-pyridine-2-yl)thiazol-2-amine

The title material was prepared as described in the synthesis of 5-bromo-N-(pyridine-2-yl)thiazol-2-amine (Example A above). LC/MS (M+H)$^+$: 270, 272. HPLC ret. time: 1.407 min. (Condition A).

C) Synthesis of N-(pyridin-2-yl)-5-thiocyanatothiazol-2-amine

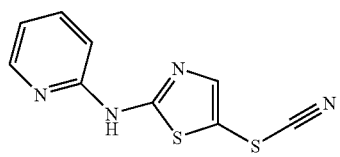 [SMILES: N#CSc1cnc(Nc2ccccn2)s1]

To a suspension of N-(pyridin-2-yl)thiazol-2-amine (4.26 g, 24 mmol) and sodium thiocyanate (3.9 g, 48 mmol, 2 eq) in methanol (100 mL) at 0° C., was slowly added bromine (1.23 mL, 24 mmol, 1 eq) over 2 min, then the temperature was raised to 23° C. and the mixture was stirred for 3 h. The resulting suspension was added to stirring cold water (400 mL) and the resulting precipitate was collected by filtration and vacuum dried (4.5 g, 80%). $^1$H NMR (400 MHz, DMSO-d6) δ ppm 7.00-7.08 (1 H, m), 7.11 (1 H, d, J=8.34 Hz), 7.74-7.84 (1 H, m), 7.89 (1 H, s), 8.39 (1 H, d, J=5.05 Hz), 11.93 (1 H, s). LC/MS (M+H)$^+$: 235.

D) Synthesis of N-(4-methylpyridin-2-yl)-5-thiocyanatothiazol-2-amine

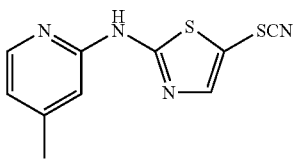

To a suspension of 4-methyl-N-(thiazol-2-yl)pyridine-2-amine (15.4 g, 80.5 mmol) and sodium thiocyanate (13.06, 161.05 mmol) in methanol (250 mL) was added dropwise bromine (4.55 mL, 88.57 mmol) over 20 min. The mixture was stirred at 23° C. After 1 h, HPLC shows complete conversion. The mixture was diluted with H$_2$O (700 mL) and concentrated on rotovap to remove the major part of the methanol. The resulting precipitate was collected by filtration and vacuum dried to give the title material (16.6 g, 100%). H$^1$ NMR (400 MHz, DMSO-d6) δ (ppm): 2.31 (3H, s), 6.89 (1H, d, J=5.30 Hz), 6.91 (1H, s), 7.87 (1H, s), 8.24 (1H, d, J=5.05 Hz), 11.85 (1H, s).

HPLC ret. time (Condition A): 1.585 min.

The thiocyanates outlined in Table 1 were prepared according to the procedure described to prepare N-(pyridin-2-yl)-5-thiocyanatothiazol-2-amine or N-(4-methylpyridin-2-yl)-5-thiocyanatothiazol-2-amine (Examples C or D above).

TABLE 1

| Structure | Name | LC/MS (M + H)+ | Ret. Time (min.) | HPLC conditions |
|---|---|---|---|---|
| 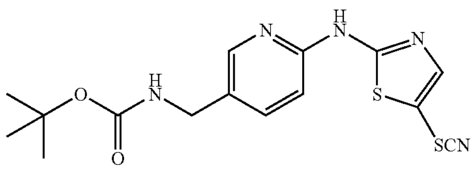 | tert-butyl (6-(5-thiocyanatothiazol-2-ylamino)pyridin-3-yl)methylcarbamate | 364 | 1.802 | B |
| 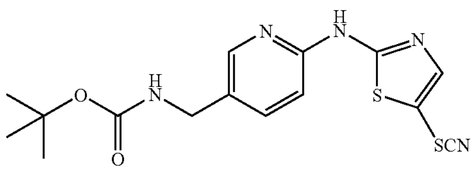 | tert-butyl methyl((6-(5-thiocyanatothiazol-2-ylamino)pyridin-3-yl)methyl)carbamate | 378 | 2.102 | A |

Synthesis of the Various Amines

A) Synthesis of tert-butyl 4-(aminomethyl)-4-phenylpiperidine-1-carboxylate

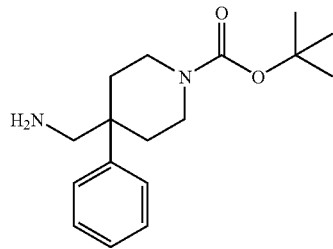 [SMILES: CC(C)(C)OC(=O)N1CCC(CN)(c2ccccc2)CC1]

1. Preparation of tert-butyl 4-cyano-4-phenylpiperidine-1-carboxylate

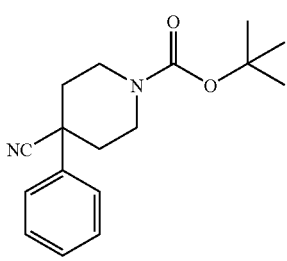

To a stirred solution of 4-phenylpiperidine-4-carbonitrile (2.0 g, 8.98 mmol) and triethylamine (1.314 mL, 9.43 mmol) in dichloromethane (10 mL) was added di-tert-butyl dicarbonate (1.99 g, 9.16 mmol) at 23° C. The resulting solution was stirred for 2 hours, then washed with water (2×), dried over anhydrous magnesium sulfate, filtered and concentrated to give the title material (2.6 g, 100%) as an oil.

2. Preparation of tert-butyl 4-(aminomethyl)-4-phenylpiperidine-1-carboxylate

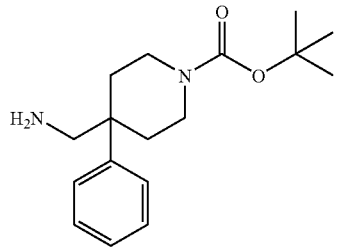 [SMILES: CC(C)(C)OC(=O)N1CCC(CN)(c2ccccc2)CC1]

Tert-butyl 4-cyano-4-phenylpiperidine-1-carboxylate (2.6 g, 9.08 mmol) was dissolved in 15% acetic acid/ethanol and hydrogenated at 50 psi over platinum oxide (0.052 g) for a week. HPLC showed only 50% conversion and the reaction was resubmitted to the same conditions and hydrogenated for 4 more days. The reaction was then filtered and the filtrate was evaporated. The residue was diluted with ethyl acetate and 1N hydrochloric acid. The aqueous phase was collected, basified with sodium carbonate and extracted with ethyl acetate. The combined organic phases were dried over anhydrous magnesium sulfate, filtered and concentrated to give the title material (0.835 g, 32%) as an oil which was used as such for the next reaction. LC/MS (M-(t-Bu)+H)+: 235. HPLC ret. time (Condition B): 1.322 min.

B) Synthesis of (1-methyl-4-phenylpiperidin-4-yl)methanamine

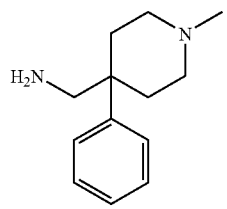

1. Preparation of 1-methyl-4-phenylpiperidine-4-carbonitrile

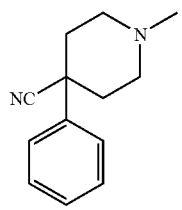

4-Phenylpiperidine-4-carbonitrile (1.35 g, 6.062 mmol) was dissolved in N,N-dimethylformamide/trimethylorthoformate (1:1, 12 mL) and treated with paraformaldehyde (0.596 mL, 18.19 mmol), triacetoxyborohydride (3.854 g, 18.185 mmol) and acetic acid (1 mL). The mixture was stirred at 23° C. overnight, then diluted with 1N hydrochloric acid and washed with ethyl acetate. The aqueous phase was basified with aqueous sodium bicarbonate and extracted with ethyl acetate. The combined organic extracts were dried over anhydrous magnesium sulfate, filtered and concentrated to give the title material (1.05 g, 50%) as an oil. LC/MS (M+H)$^+$: 200. HPLC ret. time (Condition B): 1.315 min. $^1$H NMR (400 MHz, CDCl$_3$) δ ppm: 2.10-2.21 (4H, m), 2.41 (3H, s), 2.53 (2H, td, J=11.81, 3.41 Hz), 2.99 (2H, d, J=12.38 Hz), 7.32-7.38 (1H, m), 7.39-7.45 (2H, m), 7.49-7.54 (2H, m).

2. Preparation of (1-methyl-4-phenylpiperidin-4-yl)methanamine

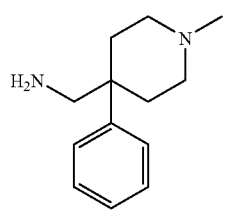

A solution of 1-methyl-4-phenylpiperidine-4-carbonitrile (1.0 g, 4.99 mmol) in THF (25 mL) was slowly added to a suspension of LAH (0.379, 9.99 mmol) in THF (10 mL). The reaction was stirred for 2 hours and then quenched with sodium sulfate decahydrate. This was stirred for 30 minutes, and then ethyl acetate was added. The mixture was stirred 10 minutes, and then filtered on celite. The filtrate was concentrated on rotovap to give the desired compound (0.916 g, 96%) as an oil. $^1$H NMR (400 MHz, CDCl$_3$) δ ppm: 1.79-1.89 24H, m), 2.18-2.28 (7H, m), 2.55-2.65 (2H, m), 2.77 (2H, s), 7.21-7.27 (1H, m), 7.28-7.39 (4H, m).

C) Synthesis of 2-(4-(aminomethyl)-4-phenylpiperidin-1-yl)ethanol

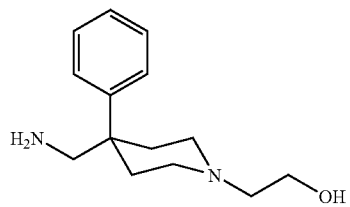 [SMILES: NCC1(c2ccccc2)CCN(CCO)CC1]

The title material was prepared as described for the synthesis of (1-methyl-4-phenylpiperidin-4-yl)methanamine (Example B above) in using 2-(tert-butyldimethylsilyloxy)acetaldehyde and by doing an acidic work-up (HCl 5N) after the reductive amination to remove the protecting group. LC/MS (M+H)$^+$: 235. HPLC ret. time (Condition A): 0.143 min.

D) Synthesis of (1-benzyl-4-phenylpiperidin-4-yl)methanamine

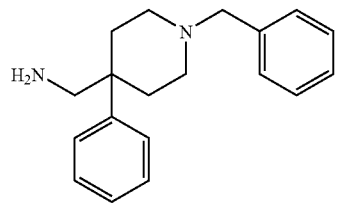 [SMILES: NCC1(c2ccccc2)CCN(Cc2ccccc2)CC1]

A suspension of 1-benzyl-4-phenylpiperidine-4-carbonitrile (2.0 g, 6.39 mmol) in THF (25 mL) was slowly added to a suspension of lithium aluminum hydride (0.340 g, 8.95 mmol) in THF (10 mL) and the reaction was stirred at 23° C. for 3 hours. The reaction was then quenched with sodium sulfate decahydrate and stirred for 30 minutes. Ethyl acetate was added and the reaction was stirred for 10 more minutes, and then filtered on celite. The filtrate was concentrated to give an oil (1.45 g, 81%) which was used as such for the next reaction. $^1$H NMR (400 MHz, CDCl$_3$) δ ppm: 1.81-1.91 (2H, m), 2.23-2.28 (4H, m), 2.65-2.67 (2H, m), 2.78 (2H, s), 3.45 (2H, s), 7.23-7.34 (8H, m), 7.36-7.41 (2H, m).

E) Synthesis of quinuclidin-4-ylmethanamine

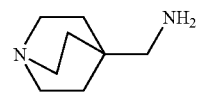

A solution of 4-cyanoquinuclidine (0.30 g, 2.2 mmol) in diethyl ether (5 mL) was slowly added to a suspension of LAH (0.167 g, 4.41 mmol) in diethyl ether (15 mL) at 0° C. The reaction was stirred at 23° C. for 3 h, then quenched with sodium sulfate decahydrate and stirred for 30 more minutes. Ethyl acetate was then added and, after 30 minutes, celite was added and the suspension was filtered on celite. The filtrate was concentrated to dryness to give an oil (0.310 g, quant.). The compound was used as such for the next reaction. $^1$H NMR (400 MHz, CDCl$_3$) δ ppm: 1.31-1.40 (6H, m), 2.43 (2H, s), 2.86-2.94 (6H, m).

F) Synthesis of (1-methyl-4-(pyridin-2-yl)piperidin-4-yl)methanamine

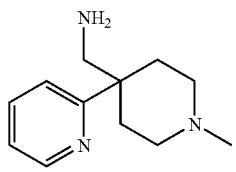

1. Preparation of 1-methyl-4-(pyridin-2-yl)piperidine-4-carbonitrile

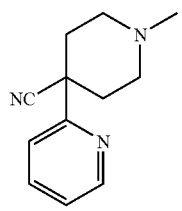

A solution of 2-pyridyl acetonitrile (1.0 g, 8.54 mmol) in DMSO (8 mL) was treated with sodium hydride (1.195 g, 29.88 mmol) portionwise. The resulting brown suspension was stirred at 23° C. for 30 minutes. 2-Chloro-N-(2-chloroethyl)-N-methylethanamine (1.81 g, 9.39 mmol) was then slowly added over 5 minutes, then the suspension was heated at 65° C. overnight. The reaction was then diluted with 1N hydrochloric acid and washed with ethyl acetate (2×). The aqueous phase was basified with 1N sodium hydroxide and extracted with ethyl acetate (3×). The combined extracts were washed with water (5×) and brine, dried over anhydrous magnesium sulfate, filtered and concentrated to give an oil. This was purified on Biotage silica gel column (1% to 10% (methanol+1% ammonia) in dichloromethane) to give the desired product as an oil (0.583 g, 34%). $^1$H NMR (400 MHz, CDCl$_3$) δ ppm: 2.14-2.25 (2H, m), 2.30-2.38 (2H, m), 2.40 (3H, s), 2.51 (td, J=12.25 and 2.27 Hz), 2.99 (2H, d, J=12.13 Hz), 7.25-7.36 (1H, m), 7.56 (1H, d, J=8.08 Hz), 7.75 (1H, td, J=7.71 and 1.77 Hz), 8.64 (1H, d, J=4.80 Hz). LC/MS (M+H)$^+$: 202. HPLC ret. time (Condition E): 1.025 min.

2. Preparation of (1-methyl-4-(pyridin-2-yl)piperidin-4-yl)methanamine

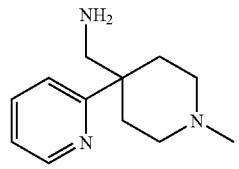

A solution of 1-methyl-4-(pyridin-2-yl)piperidine-4-carbonitrile (0.544 g, 2.70 mmol) in tetrahydrofuran (10 mL) was slowly added to a suspension of lithium aluminum hydride (0.205 g, 5.41 mmol) in tetrahydrofuran (10 mL) at 23° C. The reaction was stirred overnight, then quenched with sodium sulfate decehydrate. This was stirred for 1 hour, then ethyl acetate was added and the slurry was stirred for 2 more hours. Celite was added and the paste was filtered on Celite. The filtrate was concentrated to afford an oil (0.518 g, 93%) which was used as such for the next reaction. $^1$H NMR (400 MHz, CDCl$_3$) δ ppm: 1.76-1.88 (2H, m), 2.07-2.19 (2H, m), 2.23 (3H, s), 2.43 (2H, br d, J=14.6 Hz), 2.58-2.69 (2H, m), 2.87 (2H, s), 7.16 (1H, ddd, J=7.52, 4.86 and 1.01 Hz), 7.33 (1H, d, J=8.08 Hz), 7.69 (1H, td, J=7.77 and 1.89 Hz), 8.65 (1H, d, J=4.80 and 1.01 Hz).

G) Synthesis of (1-methyl-4-(pyridin-4-yl)piperidin-4-yl)methanamine

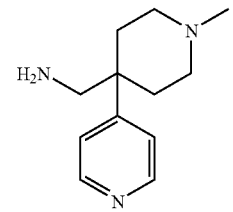

1. Preparation of 1-methyl-4-(pyridin-4-yl)piperidine-4-carbonitrile

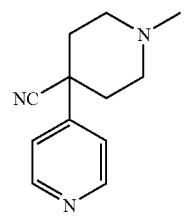

A solution of 4-pyridyl acetonitrile hydrochloride (1.0 g, 6.47 mmol) in DMSO (8 mL) was treated with sodium hydride (0.735 g, 29.11 mmol) portionwise. The resulting suspension was stirred at 23° C. for 30 minutes. 2-Chloro-N-(2-chloroethyl)-N-methylethanamine (1.37 g, 7.11 mmol) was then slowly added over 5 minutes, then the suspension was heated at 65° C. overnight. The reaction was then diluted with 1N hydrochloric acid and washed with ethyl acetate (2×). The aqueous phase was basified with 5N sodium hydroxide and extracted with ethyl acetate (3×). The combined extracts were washed with water (5×), dried over anhydrous magnesium sulfate, filtered and concentrated to give an oil (0.200 g, 15%) which was used as such for the next reaction. $^1$H NMR (400 MHz, CDCl$_3$) δ ppm: 2.10-2.17 (3H, m), 2.31-2.37 (1H, m), 2.42 (3H, s), 2.47-2.57 (2H, m), 3.01 (2G, d, J=12.6 Hz), 7.45 (2H, dd, J=4.55 and 1.52 Hz), 8.68 (2H, dd, J=4.55 and 1.77 Hz).

2. Preparation of (1-methyl-4-(pyridin-4-yl)piperidin-4-yl)methanamine

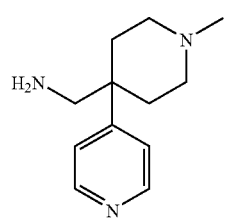

A solution of 1-methyl-4-(pyridin-4-yl)piperidine-4-carbonitrile (0.200 g, 0.994 mmol crude) in tetrahydrofuran (10 mL) was slowly added to a suspension of lithium aluminum hydride (0.075 g, 1.99 mmol) in tetrahydrofuran (10 mL) at 23° C. The reaction was stirred overnight and quenched with sodium sulfate decehydrate. This was stirred for 1 hour, then ethyl acetate was added and the slurry was stirred for 2 more hours. Celite was added and the resulting paste was filtered on Celite. The filtrate was concentrated to afford an oil (0.120 g, 59%) which was used as such for the next reaction.

H) Synthesis of (1-tert-butyl-4-phenylpiperidin-4-yl)methanamine

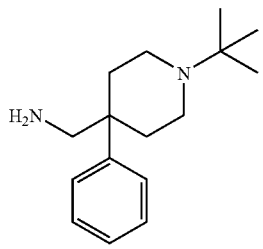 [SMILES: CC(C)(C)N1CCC(CN)(c2ccccc2)CC1]

1. Preparation of N,N-bis(2-chloroethyl)-2-methylpropan-2-amine

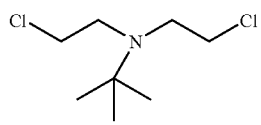

Thionyl chloride (30 mL, 409.2 mmol) was diluted in chloroform (40 mL) and stirred at 20° C. 2,2'-(Tert-butylazanediyl)diethanol (30 g, 186 mmol) in chloroform (20 mL) was added dropwise over 45 minutes. The resulting mixture was stirred for 18 hours at 20° C. and refluxed for 2 hours. The mixture was cooled and methanol (~10 mL) was added, followed by ethyl ether (~50 mL). The resulting precipitate was filtered, washed with ethyl ether and dried under vacuum to give the title material (35 g, 81%) as the HCl salt. $^1$H NMR (400 MHz, CDCl$_3$) δ ppm: 1.60 (9H, s), 3.20 (2H, s), 3.68 (2H, s), 4.12-4.19 (2H, m), 4.21-4.28 (2H, m), 12.66 (1H, s).

2. Preparation of 1-tert-butyl-4-phenylpiperidine-4-carbonitrile

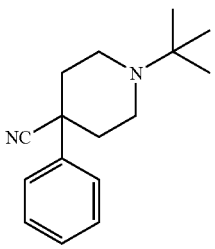

A solution of phenyl acetonitrile (1.0 g, 8.54 mmol) in DMSO (8 mL) was treated with sodium hydride (0.717 g, 29.88 mmol) portionwise. The resulting-suspension was stirred at 23° C. for 30 minutes. N,N-bis(2-chloroethyl)-2-methylpropan-2-amine (2.20 g, 9.39 mmol) was then slowly added over 5 minutes, then the suspension was heated at 65° C. overnight. The reaction was then diluted with 1N hydrochloric acid and washed with ethyl acetate (2×). The aqueous phase was basified with sat. aq. sodium carbonate and extracted with ethyl acetate (3×). The combined extracts were washed with water (5×), dried over anhydrous magnesium sulfate, filtered and concentrated to give an oil (1.40 g, 68%) which solidified on standing and was used as such for the next reaction. $^1$H NMR (400 MHz, CDCl$_3$) δ ppm: 2.10-2.17 (3H, m), 2.31-2.37 (1H, m), 2.42 (3H, s), 2.47-2.57 (2H, m), 3.01 (2G, d, J=12.6 Hz), 7.45 (2H, dd, J=4.55 and 1.52 Hz), 8.68 (2H, dd, J=4.55 and 1.77 Hz).

3. Preparation of (1-tert-butyl-4-phenylpiperidin-4-yl)methanamine

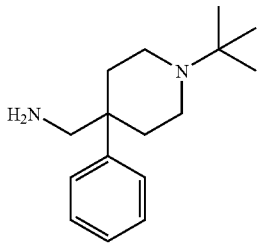 [SMILES: CC(C)(C)N1CCC(CN)(c2ccccc2)CC1]

A solution of (1-tert-butyl-4-phenylpiperidin-4-yl)methanamine (1.40 g, 5.777 mmol) in tetrahydrofuran (10 mL) was slowly added to a suspension of lithium aluminum hydride (0.438 g, 11.55 mmol) in tetrahydrofuran (10 mL) at 23° C. The reaction was stirred overnight and quenched with sodium sulfate decehydrate. The reaction mixture was stirred for 1 hour, then ethyl acetate was added and the slurry was stirred for 2 more hours. Celite was added and the resulting slurry was filtered on Celite. The filtrate was concentrated to afford an oil (1.25 g, 87%) which was used as such for the next reaction. $^1$H NMR (400 MHz, CDCl$_3$) δ ppm: 1.04 (9H, s), 1.79-1.90 (2H, m), 2.21-2.28 (2H, m), 2.38 (2H, t, J=9.85 Hz), 2.75 (2H, d, J=3.79 Hz), 2.78 (2H, s), 7.23 (1H, t, J=6.95 Hz), 7.31-7.40 (4H, m). LC/MS (M+H)$^+$: 247. HPLC ret. time (conditions D): 0.350 min.

I) Synthesis of (1-tert-butyl-4-(2-fluorophenyl)piperidin-4-yl)methanamine

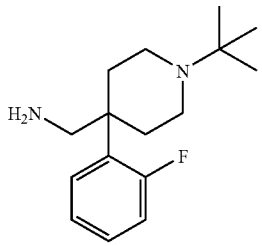 [SMILES: CC(C)(C)N1CCC(CN)(c2ccccc2F)CC1]

The title material was prepared as described in the synthesis of (1-tert-butyl-4-phenylpiperidin-4-yl)methanamine (Synthesis of amines, Example H) using 2-(2-fluorophenyl)acetonitrile.

J) Synthesis of tert-butyl 4-(aminomethyl)-4-(2,3-dichlorophenyl)piperidine-1-carboxylate

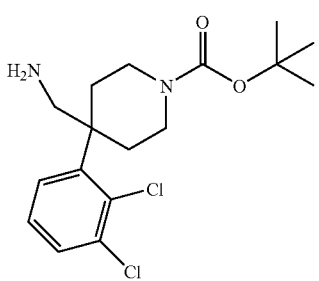 [SMILES: CC(C)(C)OC(=O)N1CCC(CN)(c2cccc(Cl)c2Cl)CC1]

1. Preparation of 2-(2,3-dichlorophenyl)acetonitrile

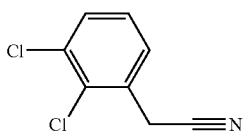

2,3-Dichlorobenzylchloride (5.0 g, 25.5 mmol) was dissolved in 100 ml DMSO. 9.2 g NaCN (188 mmol) were added and the mixture stirred at room temperature for 16 hours. The reaction mixture was diluted with water, and the product extracted with ether. The organic layers were washed with water (2×) and brine, then dried over magnesium sulfate, filtered and concentrated. The product was used as. Crude yield~quantitative. An analytical sample was purified by column chromatography on silica, using a gradient from 10% to 75% dichloromethane in hexanes as eluent. The combined aqueous layers and wash liquids were treated with 100 ml bleach to oxidize the excess cyanide to less toxic materials.

2. Preparation of tert-butyl 4-cyano-4-(2,3-dichlorophenyl)piperidine-1-carboxylate

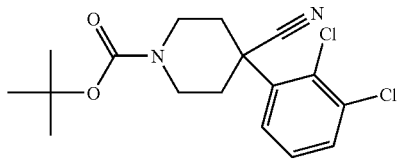 [SMILES: CC(C)(C)OC(=O)N1CCC(C#N)(c2cccc(Cl)c2Cl)CC1]

2-(2,3-dichlorophenyl)acetonitrile (2.49 g crude, est. 83% purity, 11 mmol), 2.70 g tert-butyl bis(2-chloroethyl)carbamate (J. Med. Chem. 1992, 35, 11, 2033-2039) (11 mmol), 19.5 g aesium carbonate (60 mmol) and 200 ml DMSO were combined in a round bottom flask and stirred at room temperature for 4 days. The reaction mixture was diluted with ethyl acetate and the organic layer washed with 1M aq. KHSO$_4$ solution, and then saturated aq. NaHCO$_3$ solution, then brine. The organic layer was dried over magnesium sulfate, filtered and concentrated. The product was purified by column chromatography on silica, using a gradient from 5% to 35% ethyl acetate in hexanes as eluent. 2.3 g of the title compound were isolated as an oil (59% yield)

3. Preparation of tert-butyl 4-(aminomethyl)-4-(2,3-dichlorophenyl)-piperidine-1-carboxylate

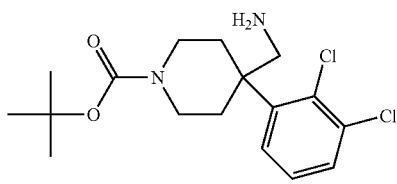 [SMILES: CC(C)(C)OC(=O)N1CCC(CN)(c2cccc(Cl)c2Cl)CC1]

Tert-butyl 4-cyano-4-(2,3-dichlorophenyl)piperidine-1-carboxylate (2.30 g, 6.47 mmol) was dissolved in 75 ml of a 7M solution of NH$_3$ in MeOH. Raney Nickel (~2 g aq. suspension) was added and the mixture shaken on a PARR apparatus under 60 psi of hydrogen for 4 days. The catalyst was removed by filtration through a layer of Celite and the crude reaction mixture concentrated. The crude product (1.90 g yellow oil) was used in the next reaction (amide bond formation) "as is".

K) Synthesis of tert-butyl 4-(aminomethyl)-4-(3,4-dichlorophenyl)piperidine-1-carboxylate

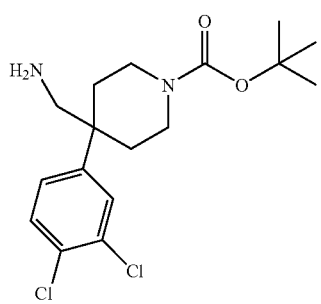 [SMILES: CC(C)(C)OC(=O)N1CCC(CN)(c2ccc(Cl)c(Cl)c2)CC1]

The compound was prepared following steps 2 and 3 of the 3-step sequence described above for amine example J, but using (3,4-Dichlorophenyl)-acetonitrile as starting material.

L) Synthesis of tert-butyl 4-(aminomethyl)-4-(pyridin-4-yl)piperidine-1-carboxylate

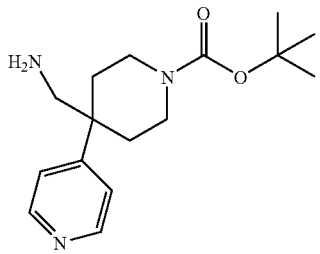 [SMILES: CC(C)(C)OC(=O)N1CCC(CN)(c2ccncc2)CC1]

1. Preparation of tert-butyl 4-cyano-4-(pyridin-4-yl)piperidine-1-carboxylate

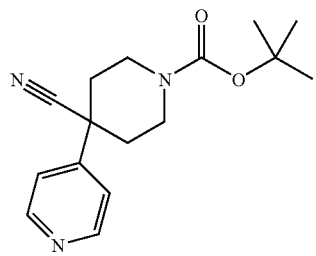 [SMILES: CC(C)(C)OC(=O)N1CCC(C#N)(c2ccncc2)CC1]

4-Cyanomethylpyridinium hydrochloride (1.0 g, 6.5 mmol), 2.0 g tert-butyl bis(2-chloroethyl)carbamate (J. Med. Chem. 1992, 35, 11, 2033-2039) (8.1 mmol), 9.1 g caesium carbonate (28 mmol) and 20 ml DMSO were combined in a round bottom flask and stirred at room temperature for 20 hours. The reaction mixture was diluted with ethyl acetate and the organic layer washed with water, then brine. The organic layer was dried over magnesium sulfate, filtered and concentrated. The product was purified by column chromatography on silica, using a gradient from 10% to 100% ethyl acetate in hexanes as eluent. 778 mg of the title compound were isolated as an oil (42% yield)

2. Preparation of tert-butyl 4-(aminomethyl)-4-(pyridin-4-yl)piperidine-1-carboxylate

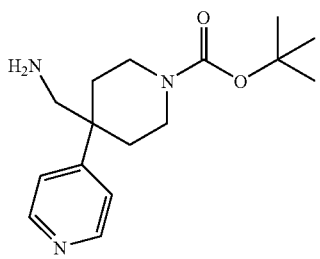 [SMILES: CC(C)(C)OC(=O)N1CCC(CN)(c2ccncc2)CC1]

Using the same procedure as described for amine example J, step 3. Yield 85%

M) Synthesis of tert-butyl 4-(aminomethyl)-4-(pyridin-3-yl)piperidine-1-carboxylate

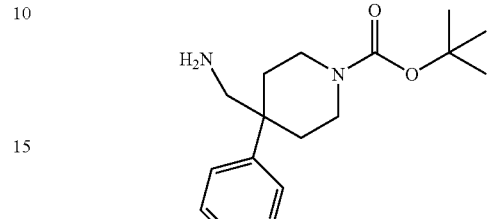

The compound was prepared following the same 2-step sequence described above for amine example L, but using 3-Pyridyl-acetonitrile as starting material and using Pd(OH)$_2$ as hydrogenation catalyst.

N) Synthesis of tert-butyl 4-(aminomethyl)-4-(pyridin-2-yl)piperidine-1-carboxylate

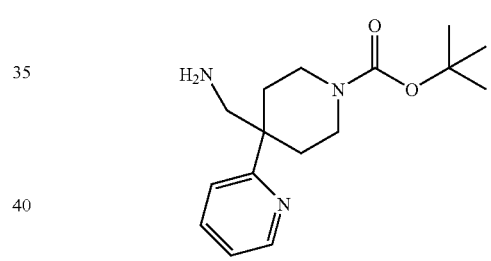

The compound was prepared following the same 2-step sequence described above for amine example L, but using 2-Pyridyl-acetonitrile as starting material and using Pd(OH)$_2$ as hydrogenation catalyst.

O) Synthesis of tert-butyl 4-(aminomethyl)-4-(2-fluorophenyl)piperidine-1-carboxylate

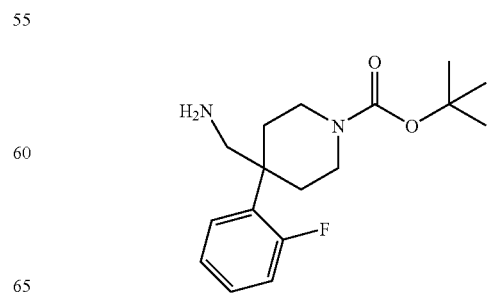

The compound was prepared following steps 2 and 3 of the 3-step sequence described above for amine example J, but using (2-fluorophenyl)-acetonitrile as the starting material.

P) Synthesis of tert-butyl 4-(aminomethyl)-4-(4-fluorophenyl)piperidine-1-carboxylate

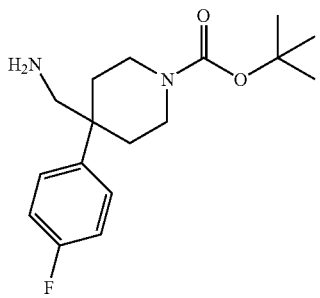 [SMILES: CC(C)(C)OC(=O)N1CCC(CN)(c2ccc(F)cc2)CC1]

The compound was prepared following steps 2 and 3 of the 3-step sequence described above for amine example J, but using (4-fluorophenyl)-acetonitrile as starting material.

Q) Synthesis of tert-butyl 4-(aminomethyl)-4-(2,4-difluorophenyl)piperidine-1-carboxylate

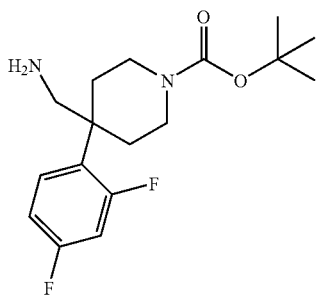 [SMILES: CC(C)(C)OC(=O)N1CCC(CN)(c2ccc(F)cc2F)CC1]

The compound was prepared following steps 2 and 3 of the 3-step sequence described above for amine example J, but using (2,4-difluorophenyl)-acetonitrile as starting material.

R) Synthesis of tert-butyl 4-(aminomethyl)-4-cyclohexylpiperidine-1-carboxylate

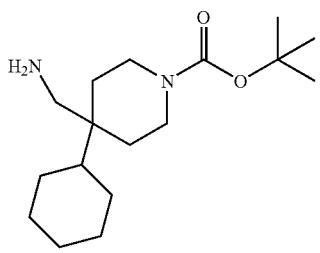 [SMILES: CC(C)(C)OC(=O)N1CCC(CN)(C2CCCCC2)CC1]

Tert-butyl 4-(aminomethyl)-4-phenylpiperidine-1-carboxylate (355 mg, 1.22 mmol) and 1.15 g PtO$_2$ (5.1 mmol) in 125 ml ethanol were shaken in PARR apparatus under 60 psi of hydrogen for 20 hours. Celite was loaded on top of an ion exchange cartridge (MCX, Phenomenex, 6 g adsorbent). The crude reaction slurry was filtered through this set-up, the pyrophoric catalyst washed with ethanol and water and removed. The cartridge was washed with methanol and then the product eluted with a 2 M solution of NH$_3$ in MeOH. The eluent was concentrated to give 234 mg of the title compound as an oil.

S) Synthesis of tert-butyl 4-(aminomethyl)-4-(5-methylisoxazol-3-yl)piperidine-1-carboxylate

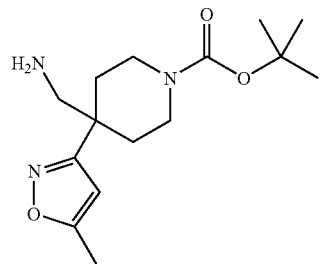 [SMILES: Cc1cc(C2(CN)CCN(C(=O)OC(C)(C)C)CC2)no1]

1. Preparation of 2-(5-methylisoxazol-3-yl)acetonitrile

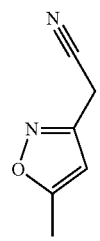

The compound was prepared following the procedure described above as step 1 in the synthesis of amine example J. The crude product was ~95% pure and was used "as is". Crude yield 95%.

2. Preparation of tert-butyl 4-cyano-4-(5-methylisoxazol-3-yl)piperidine-1-carboxylate

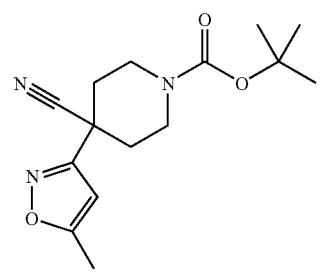 [SMILES: Cc1cc(C2(C#N)CCN(C(=O)OC(C)(C)C)CC2)no1]

The compound was prepared following the procedure described above as step 1 in the synthesis of amine example L. Column chromatography conditions: silica, gradient elution, 5% ethyl acetate in hexanes to 100% ethyl acetate. The title compound was isolated after evaporation of the product containing fractions. (0.50 g, 26% yield over 2 steps).

3. Preparation of tert-butyl 4-(aminomethyl)-4-(5-methylisoxazol-3-yl)piperidine-1-carboxylate

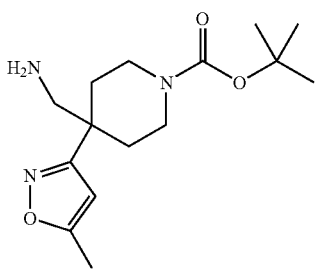 [SMILES: Cc1cc(C2(CN)CCN(C(=O)OC(C)(C)C)CC2)no1]

470 mg tert-butyl 4-cyano-4-(5-methylisoxazol-3-yl)piperidine-1-carboxylate and 1.24 g Bu$_4$NBH$_4$ were dissolved in 10 ml dichloromethane in a sealed tube and heated in a microwave reactor to 80 C for 1 hour. The reaction mixture was cooled to room temperature, the vial opened and the excess borohydride was quenched by slow addition of 5 ml MeOH. After stirring for 1 hour the vial was re-sealed and heated to 100 C. for 20 minutes (to hydrolyse the boron complex of the product). The reaction mixture was poured into sat. aq. NaHCO$_3$ solution and extracted with dichloromethane. The organic layer was washed with brine, dryed over MgSO$_4$, filtered and concentrated. The crude title amine (0.51 g, quant. yield) was used "as is".

T) Synthesis of 4-(aminomethyl)-4-(4-fluorophenyl)cyclohexanol

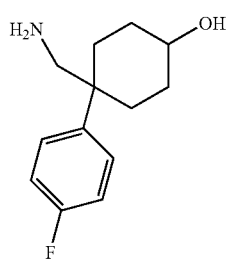

100 mg 1-(4-fluorophenyl)-4-oxocyclohexanecarbonitrile was hydrogenated as described for step 3 of amine example J. Both the cyano and keto functionality were reduced to a homogenous product of currently unknown configuration at the secondary alcohol carbon.

U) Synthesis of (4-phenyltetrahydro-2H-pyran-4-yl)methanamine

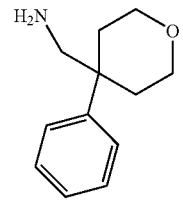 [SMILES: NCC1(c2ccccc2)CCOCC1]

Hattersley, P. J.; Lockhart, Ian M.; Some reactions with 4-cyano-4-phenyltetrahydropyran; Journal of Medicinal Chemistry (1967), 10(1), 128-9.

V) Synthesis of (1-(3,4-dimethoxyphenyl)cyclohexyl)methanamine

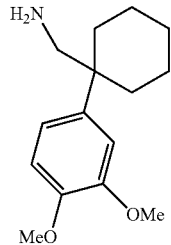

Hadida, Ruah Sara S.; Singh, Ashvani K.; Miller, Mark T.; Hamilton, Matthew; Grootenhuis, Peter D. J. Preparation of phenethyl (hetero)aryl amides as modulators of ATP-binding cassette (ABC) transporters. PCT Int. Appl. (2005), 160 pp. CODEN: PIXXD2 WO 2005035514 A2 20050421 CAN 142:411216 AN 2005:346999 CAPLUS Eliason, James F.; Ramuz, Henri; Kaufmann-schmid, Franz Alois. Preparation of 2-(6-phenyl-4-azahexyl)-1,3-dithianes for reducing chloroquine resistance in treatment of malaria and for reducing polydrug resistance in treatment of cancer. Eur. Pat. Appl. (1993), 32 pp. CODEN: EPXXDW EP 523493 A1 19930120 CAN 119:72613 AN 1993:472613 CAPLUS Markaryan, E. A.; Arustamyan, Zh. S. Isoquinoline derivatives. X. Synthesis of 2-aralkyl-4-spirocyclohexane-6,7-dimethoxy-1,2,3,4-tetrahydroisoquinolines and their acyclic analogs. Armyanskii Khimicheskii Zhurnal (1974), 27(9), 779-84. CODEN: AYKZAN ISSN:0515-9628. CAN 82:139935 AN 1975:139935 CAPLUS

W) Synthesis of (4-(2-fluorophenyl)-1-methylpiperidin-4-yl)methanamine

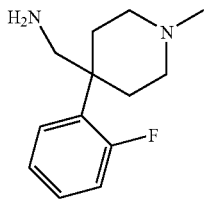 [SMILES: CN1CCC(CN)(c2ccccc2F)CC1]

Ong, Helen H.; Profitt, James A.; Fortunato, James; Glamkowski, Edward J.; Ellis, Daniel B.; Geyer, Harry M., III; Wilker, Jeffrey C.; Burghard, Harald. Novel tetracyclic spiropiperidines. 3. 1-Arylspiro[indoline-3,4'-piperidine]s as potential antidepressants. Journal of Medicinal Chemistry (1983), 26(7), 981-6.

EXAMPLE 1

Tert-butyl 4-((3-fluoro-4-(2-(4-methylpyridin-2-ylamino)thiazol-5-ylthio)picolinamido)methyl)-4-phenylpiperidine-1-carboxylate

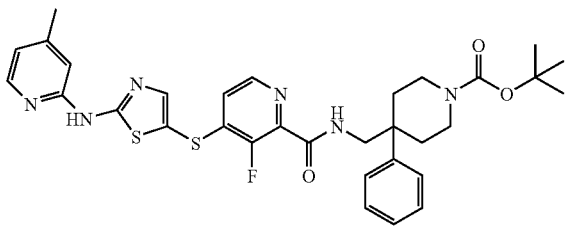 [SMILES: Cc1ccnc(Nc2ncc(Sc3ccnc(C(=O)NCC4(c5ccccc5)CCN(C(=O)OC(C)(C)C)CC4)c3F)s2)c1]

A. Synthesis of methyl 4-chloro-3-fluoropicolinate

The title compound was prepared according to the procedure described in Org. Prep. and Proc. Int., 29 (1), 117-122 (1997). A suspension of lithium 3-fluoropicolinate (20.0 g, 136 mmol) and sodium bromide (28.0 g, 272 mmol, 2 eq) in thionyl chloride (99 mL, 1.36 umol, 10 eq) was heated to reflux (95° C.) with an argon flush. The reaction was refluxed for 2 days then thionyl chloride (50 mL, 680 mmol, 5 eq) was added again and the reaction was refluxed for 3 more days. The mixture was then evaporated and the residue cooled down to 0° C. Methanol (300 mL) was cautiously added by portions and the mixture was stirred at 23° C. overnight. The reaction was then partitioned into ethyl acetate/sat. aq sodium carbonate and the aqueous phase was extracted with ethyl acetate. The combined organic layers were dried over magnesium sulfate, filtered and concentrated. The residue was dissolved in boiling hexanes and the residual black tar was decanted. The filtrate was evaporated to give the title material (24.36 g, 94%) as a solid. $^1$H NMR (400 MHz, DMSO-d6) δ ppm 3.92 (3H, s), 8.01 (1H, t, J=5.1 Hz), 8.50 (1H, d, J=5.1 Hz). LC/MS (M+H)$^+$: 190.

B. Synthesis of 3-fluoro-4-(2-(4-methylpyridin-2-ylamino)thiazol-5-ylthio)picolinic acid

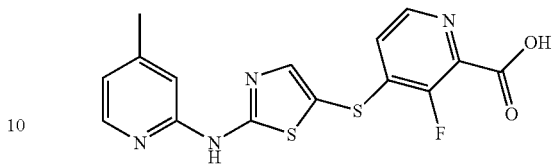

To a suspension of N-(4-methylpyridin-2-yl)-5-thiocyanatothiazol-2-amine (3.4 g, 13.69 mmol, described in the synthesis of thiocyanates, Example D) in methanol (150 mL, previously bubbled with argon) was added dithiothreitol (3.70 g, 23.96 mmol). The reaction was stirred at 23° C. for 10 minutes, and then methyl 4-chloro-3-fluoropicolinate (2.27 g, 11.98 mmol) was added followed by an aqueous solution of NaOH (1N, 12 mL, 11.98 mmol). The resulting reaction was stirred for 1 hour, and then concentrated to ~¼ of the volume. The mixture was then diluted with water (200 mL) and neutralized with ammonium chloride. The resulting solid was collected by filtration and vacuum dried to give the crude title material (5.7 g) as a solid. This solid was purified on silica gel Biotage chromatography (ethyl acetate) to give the title material (3.01 g, 70%) as a solid. $^1$H NMR of the compound showed contamination with dithiothreitol. The compound was used as such for the next reaction.

The solid was dissolved in THF (100 mL) and the solution was treated with aqueous sodium hydroxide (1N, 12 mL, 11.95 mmol). The reaction was stirred at 23° C. for 2 hours, then diluted with water and neutralized with 1N aq. HCl. The mixture was concentrated to remove THF and the resulting solid was collected by filtration and vacuum dried to give the title material (1.86 g, 64%) as a solid. $^1$H NMR (400 MHz, DMSO-d6) δ ppm: 2.31 (3H, s), 6.67-6.73 (1H, m), 6.84 (1H, d, J=4.55 Hz), 6.92 (1H, s), 7.74-7.78 (1H, m), 8.04 (1H, d, J=4.29 Hz), 8.17 (1H, t, J=4.55 Hz).

C. Synthesis of tent-butyl 4-((3-fluoro-4-(2-(4-methylpyridin-2-ylamino)thiazol-5-ylthio)picolinamido) methyl)-4-phenylpiperidine-1-carboxylate

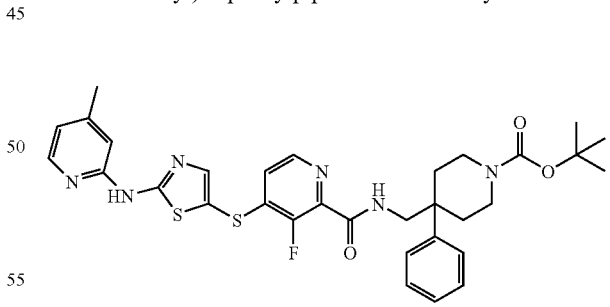

Tert-butyl 4-(aminomethyl)-4-phenylpiperidine-1-carboxylate (0.385 g, 1.325 mmol, 1.2 eq) was dissolved in NMP (10 mL) and to this solution was added 3-fluoro-4-(2-(pyridin-2-ylamino)thiazol-5-ylthio)picolinic acid (0.400 g, 1.104 mmol), EDAC (0.317 g, 1.656 mmol, 1.5 eq), HOBt (0.149 g, 1.104 mmol, 1 eq) and diisopropylethylamine (0.983 mL, 5.52 mmol, 5 eq). The resulting mixture was stirred at 23° C. for 2 days. The mixture was then diluted with 10% water/90% acetonitrile/0.05% TFA, purified on preparative HPLC (ammonium acetate/water/acetonitrile) and freeze dried to give the title compound (0.270 g, 39%). ¹H NMR (400 MHz, DMSO-d6) δ ppm: 1.38 (9H, s), 1.75 (2H, ddd, J=13.5, 10.2, 3.3 Hz), 2.04-2.15 (2H, m), 2.31 (3H, s), 2.91 (2H, br s), 3.42 (2H, d, J=6.32 Hz), 3.59-3.70 (2H, m), 6.86 (1H, t, J=5.3 Hz), 6.91 (1H, s), 7.03 (1H, t, J=5.31 Hz), 7.25 (1H, t, J=7.07 Hz), 7.34-7.45 (4H, m), 7.81 (1H, s), 8.16 (1H, t, J=4.55 Hz), 8.21 (1H, d, J=5.05 Hz), 8.25 (1H, d, J=6.44 Hz), 11.78 (1H, s). LC/MS (M+H)⁺: 635. HPLC ret. time (Condition C): 7.033 min.

EXAMPLE 2

3-Fluoro-N-((1-methyl-4-phenylpiperidin-4-yl)methyl)-4-(2-(4-methylpyridin-2-ylamino)thiazol-5-ylthio)picolinamide

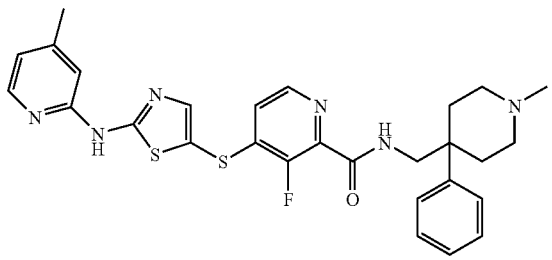 [SMILES: Cc1ccnc(Nc2ncc(Sc3ccnc(C(=O)NCC4(c5ccccc5)CCN(C)CC4)c3F)s2)c1]

The title material was prepared as described in Example 1 using 1-methyl-4-phenylpiperidin-4-yl)methanamine (described in the synthesis of amines, Example B). LC/MS (M+H)⁺: 549. HPLC ret. time (Condition C): 4.191 min. HRMS calcd: 549.1907; found: 549.1884.

EXAMPLE 3

Tert-butyl 4-((3-fluoro-4-(2-(4-methylpyridin-2-ylamino)thiazol-5-ylthio)picolinamido)methyl)piperidine-1-carboxylate

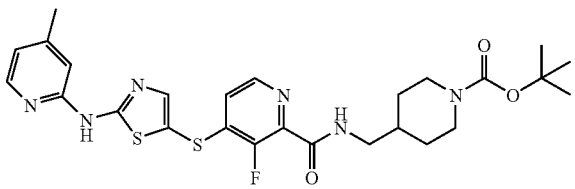 [SMILES: Cc1ccnc(Nc2ncc(Sc3ccnc(C(=O)NCC4CCN(C(=O)OC(C)(C)C)CC4)c3F)s2)c1]

The title material was prepared as described in Example 1 using tert-butyl 4-(aminomethyl)piperidine-1-carboxylate (commercially available). LC/MS (M+H)⁺: 559. HPLC ret. time (Condition C): 5.926 min.

EXAMPLE 4

3-Fluoro-4-(2-(4-methylpyridin-2-ylamino)thiazol-5-ylthio)-N-(quinuclidin-4-ylmethyl)picolinamide

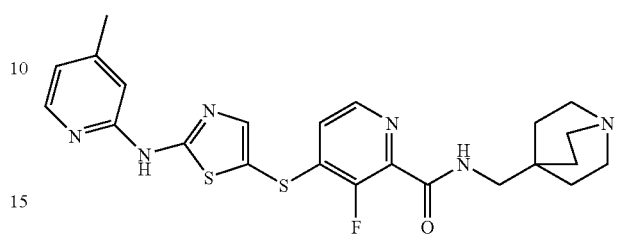

The title material was prepared as described in Example 1 using quinuclidin-4-ylmethanamine (described in the synthesis of amines, Example E). LC/MS (M+H)⁺: 485. HPLC ret. time (Condition C): 3.455 min.

EXAMPLE 5

3-Fluoro-N-((1-(2-hydroxyethyl)-4-phenylpiperidin-4-yl)methyl)-4-(2-(4-methylpyridin-2-ylamino)thiazol-5-ylthio)picolinamide

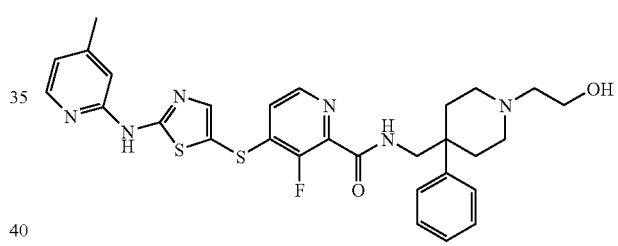

The title material was prepared as described in Example 1 using 2-(4-(aminomethyl)-4-phenylpiperidin-1-yl)ethanol (described in the synthesis of amines, Example C). LC/MS (M+H)⁺: 579. HPLC ret. time (Condition C): 4.078 min. HRMS calcd: 579.2012; found: 579.2002.

EXAMPLE 6

N-((1-benzyl-4-phenylpiperidin-4-yl)methyl)-3-fluoro-4-(2-(4-methylpyridin-2-ylamino)thiazol-5-ylthio)picolinamide

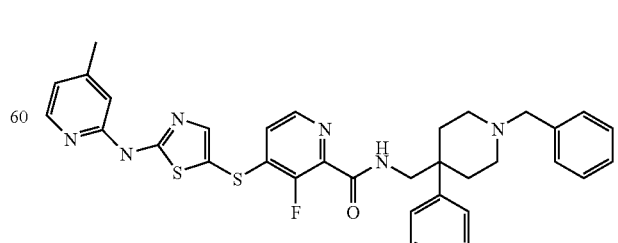

The title material was prepared as described in Example 1 using (1-benzyl-4-phenylpiperidin-4-yl)methanamine (described in the synthesis of amines, Example D). LC/MS (M+H)+: 625. HPLC ret. time (Condition C): 5.093 min. HRMS calcd: 625.2220; found: 625.2232.

EXAMPLE 7

3-Fluoro-N-((1-methyl-4-(pyridin-2-yl)piperidin-4-yl)methyl)-4-(2-(4-methylpyridin-2-ylamino)thiazol-5-ylthio)picolinamide

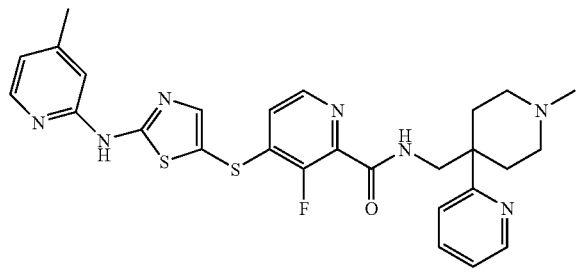

The title material was prepared as described in Example 1 using (1-methyl-4-(pyridin-2-yl)piperidin-4-yl)methanamine (described in the synthesis of amines, Example F). LC/MS (M+H)+: 550. HPLC ret. time (Condition C): 3.531 min.

EXAMPLE 8

3-Fluoro-N-((1-methyl-4-(pyridin-4-yl)piperidin-4-yl)methyl)-4-(2-(4-methylpyridin-2-ylamino)thiazol-5-ylthio)picolinamide

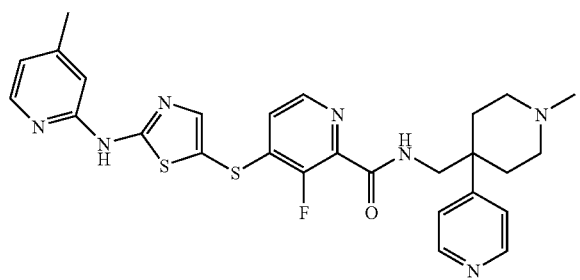 [SMILES: Cc1ccnc(Nc2ncc(Sc3ccnc(C(=O)NCC4(c5ccncc5)CCN(C)CC4)c3F)s2)c1]

The title material was prepared as described in Example 1 using (1-methyl-4-(pyridin-4-yl)piperidin-4-yl)methanamine (described in the synthesis of amines, Example G). LC/MS (M+H)+: 550. HPLC ret. time (Condition C): 3.086 min.

EXAMPLE 9

N-((1-tert-butyl-4-phenylpiperidin-4-yl)methyl)-3-fluoro-4-(2-(4-methylpyridin-2-ylamino)thiazol-5-ylthio)picolinamide

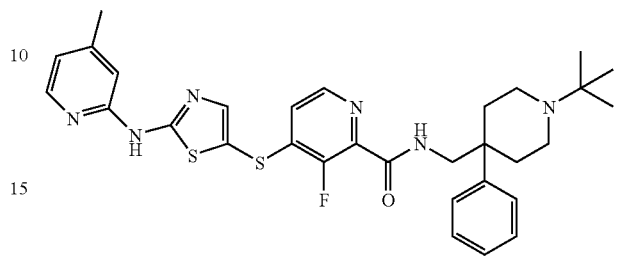

The title material was prepared as described in Example 1 using (1-tert-butyl-4-phenylpiperidin-4-yl)methanamine (described in the synthesis of amines, Example H). LC/MS (M+H)+: 591. HPLC ret. time (Condition C): 4.663 min.

EXAMPLE 10

N-((1-tert-butyl-4-(2-fluorophenyl)piperidin-4-yl)methyl)-3-fluoro-4-(2-(4-methylpyridin-2-ylamino)thiazol-5-ylthio)picolinamide

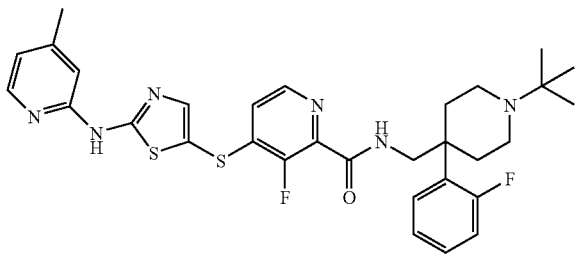 [SMILES: Cc1ccnc(Nc2ncc(Sc3ccnc(C(=O)NCC4(c5ccccc5F)CCN(C(C)(C)C)CC4)c3F)s2)c1]

The title material was prepared as described in Example 1 using (1-tert-butyl-4-(2-fluorophenyl)piperidin-4-yl)methanamine (described in the synthesis of amines, Example I). LC/MS (M+H)+: 609. HPLC ret. time (Condition C): 4.743 min.

EXAMPLE 11

3-Fluoro-4-(2-(4-methylpyridin-2-ylamino)thiazol-5-ylthio)-N-((4-phenylpiperidin-4-yl)methyl)picolinamide Tert-butyl 4-((3-fluoro-4-(2-(4-methylpyridin-2-ylamino)thiazol-5-ylthio)picolinamido)methyl)-4-phenylpiperidine-1-carboxylate (~1.80 g, ~2.84 mmol, described in Example 1) was dissolved in trifluoroacetic acid/dichloromethane (1:5, mL). This mixture was stirred at 23° C. for 2 hours, then neutralized with sat. sodium carbonate to pH~7. The aqueous phase was then extracted with ethyl acetate/THF and the combined organic layers were dried over anhydrous magnesium sulfate to give the title material (1.06 g, 70%) as a solid. $^1$H NMR (400 MHz, DMSO-d6) δ ppm 1.99-2.09 (2H, m), 2.28 (2H, br s), 2.31 (3H, s), 2.66-2.82 (2H, m), 3.25 (2H, m), 3.45 (2H, br d), 6.86 (1H, d, J=5.31 Hz), 6.93 (1H, s), 7.05 (1H, t, J=5.18 Hz), 7.26-7.34 (1H, m), 7.38-7.46 (4H, m), 7.81 (1H, s), 8.17 (1H, d, J=5.31 Hz), 8.23 (1H, d, J=5.05 Hz), 8.37 (1H, t, J=6.44 Hz), 11.84 (1H, s). LC/MS (M+H)$^+$: 535. HPLC ret. time (Condition C): 4.085 min.

EXAMPLE 12

N-((1-(2-(dimethylamino)acetyl)-4-phenylpiperidin-4-yl)methyl)-3-fluoro-4-(2-(4-methylpyridin-2-ylamino)thiazol-5-ylthio)picolinamide

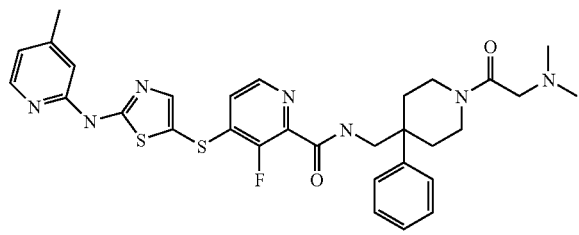 [SMILES: Cc1ccnc(Nc2ncc(Sc3ccnc(C(=O)NCC4(c5ccccc5)CCN(C(=O)CN(C)C)CC4)c3F)s2)c1]

3-Fluoro-4-(2-(4-methylpyridin-2-ylamino)thiazol-5-ylthio)-N-((4-phenylpiperidin-4-yl)methyl)picolinamide (crude from deprotection of 3-fluoro-4-(2-(4-methylpyridin-2-ylamino)thiazol-5-ylthio)-N-((4-phenylpiperidin-4-yl)methyl)picolinamide, 0.140 g, 0.221 mmol) was dissolved in NMP (8 mL) and treated with EDAC (0.063 g, 0.331 mmol), HOBT (0.030 g, 0.221 mmol), diisopropylethylamine (0.196 mL, 1.103 mmol) and dimethylglycine (0.034, 0.331 mmol). The reaction was stirred at 23° C. overnight and then diluted with TFA. This was purified on preparative HPLC (TFA/acetonitrile/water). The fractions containing the desired product were combined and concentrated to ¼ of the volume. The resulting solution was applied on a SCX SPE cartridge (Waters Oasis™), washed with methanol and eluted with 2M ammonia/methanol. After concentration, the resulting solid (0.037 g, 0.0596 mmol, 27%) was suspended in acetonitrile and treated with a 0.1N HCl/methanol solution (0.596 mL). The resulting solution was diluted with water and freeze dried to give the title material as the HCl salt. $^1$H NMR (400 MHz, DMSO-d6) δ ppm: 1.76-1.89 (2H, m), 2.11-2.23 (2H, m), 2.31 (3H, s), 2.55 (6H, br s), 3.00 (1H, t, J=11.1 Hz), 3.10 (1H, t, J=11.0 Hz), 3.47 (2H, d, J=6.57 Hz), 3.63 (1H, d, J=13.1 Hz), 3.94 (1H, d, J=14.6 Hz), 6.86 (1H, d, J=5.56 Hz), 6.92 (1H, s), 7.04 (1H, t, J=5.31 Hz), 7.27 (1H, t, J=7.07 Hz), 7.40 (2H, t, J=7.71 Hz), 7.43-7.47 (2H, m), 7.81 (1H, s), 8.17 (1H, d, J=5.31 Hz), 8.19-8.25 (2H, m), 11.81 (1H, s). LC/MS (M+H)$^+$: 620. HPLC ret. time (Condition C): 4.363 min. HRMS calcd: 620.2278; found: 620.2279.

EXAMPLE 13

N-((1-butyryl-4-phenylpiperidin-4-yl)methyl)-3-fluoro-4-(2-(4-methylpyridin-2-ylamino)thiazol-5-ylthio)picolinamide

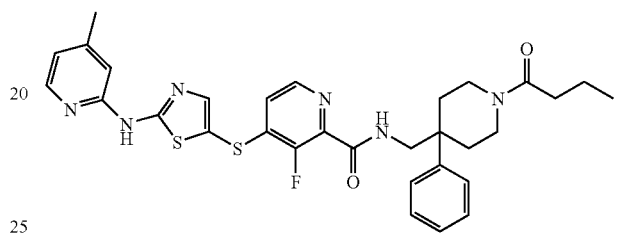

The title material was prepared as described in Example 12 using butyric acid. LC/MS (M+H)$^+$: 605. HPLC ret. time (Condition C): 5.906 min. HRMS calcd: 605.2169; found: 605.2181.

EXAMPLE 14

N-((1-(cyclopentanecarbonyl)-4-phenylpiperidin-4-yl)methyl)-3-fluoro-4-(2-(4-methylpyridin-2-ylamino)thiazol-5-ylthio)picolinamide

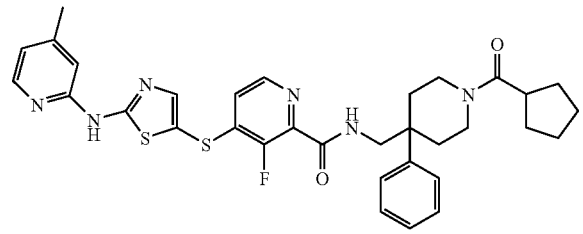 [SMILES: Cc1ccnc(Nc2ncc(Sc3ccnc(C(=O)NCC4(c5ccccc5)CCN(C(=O)C5CCCC5)CC4)c3F)s2)c1]

The title material was prepared as described in Example 12 using cyclopentane carboxylic acid. LC/MS (M+H)$^+$: 631. HPLC ret. time (Condition C): 6.418 min. HRMS calcd: 631.2325; found: 631.2346.

EXAMPLE 15

3-Fluoro-N-((1-(1-methyl-1H-pyrrole-2-carbonyl)-4-phenylpiperidin-4-yl)methyl)-4-(2-(4-methylpyridin-2-ylamino)thiazol-5-ylthio)picolinamide

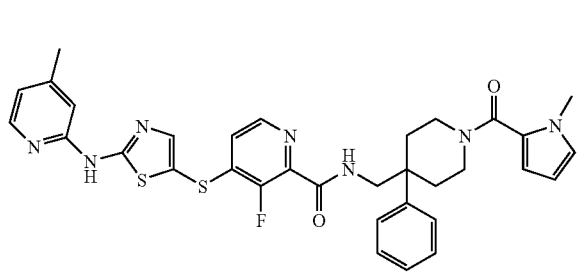 [SMILES: Cc1ccnc(Nc2ncc(Sc3ccnc(C(=O)NCC4(c5ccccc5)CCN(C(=O)c5cccs5)CC4)c3F)s2)c1]

The title material was prepared as described in Example 12 using 1-methyl-1H-pyrrole-2-carboxylic acid. LC/MS (M+H)$^+$: 642. HPLC ret. time (Condition C): 6.063 min. HRMS calcd: 642.2121; found: 642.2131.

EXAMPLE 16

3-Fluoro-4-(2-(4-methylpyridin-2-ylamino)thiazol-5-ylthio)-N-((4-phenyl-1-(thiophene-2-carbonyl)piperidin-4-yl)methyl)picolinamide

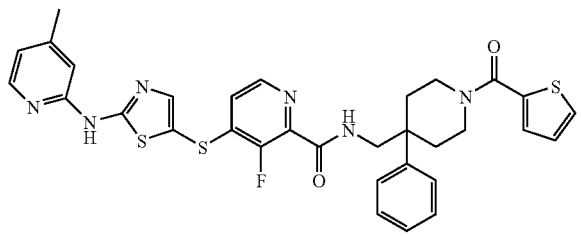 [SMILES: Cc1ccnc(Nc2ncc(Sc3ccnc(C(=O)NCC4(c5ccccc5)CCN(C(=O)c5ccco5)CC4)c3F)s2)c1]

The title material was prepared as described in Example 12 using thiophene-2-carboxylic acid. LC/MS (M+H)$^+$: 645. HPLC ret. time (Condition C): 6.101 min.

EXAMPLE 17

3-Fluoro-N-((1-(furan-2-carbonyl)-4-phenylpiperidin-4-yl)methyl)-4-(2-(4-methylpyridin-2-ylamino)thiazol-5-ylthio)picolinamide

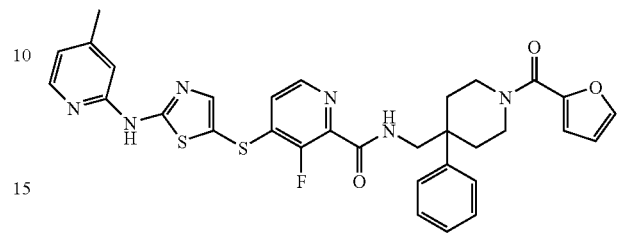

The title material was prepared as described in Example 12 using furan-2-carboxylic acid. LC/MS (M+H)$^+$: 629. HPLC ret. time (Condition C): 5.815 min.

EXAMPLE 18

3-Fluoro-4-(2-(4-methylpyridin-2-ylamino)thiazol-5-ylthio)-N-((1-nicotinoyl-4-phenylpiperidin-4-yl)methyl)picolinamide

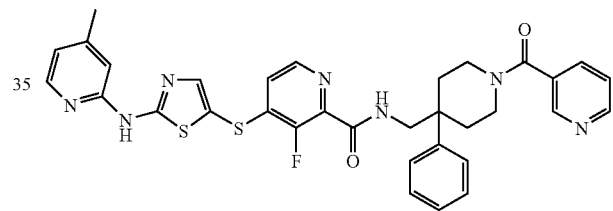

The title material was prepared as described in Example 12 using nicotinic acid. LC/MS (M+H)$^+$: 640. HPLC ret. time (Condition C): 4.778 min. HRMS calcd: 640.1965; found: 640.1982.

EXAMPLE 19

N-((1-(1H-benzo[d]imidazole-6-carbonyl)-4-phenylpiperidin-4-yl)methyl)-3-fluoro-4-(2-(4-methylpyridin-2-ylamino)thiazol-5-ylthio)picolinamide

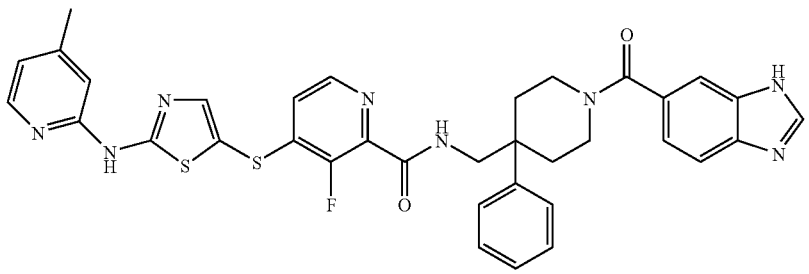 [SMILES: Cc1ccnc(Nc2ncc(Sc3ccnc(C(=O)NCC4(c5ccccc5)CCN(C(=O)c5ccc6nc[nH]c6c5)CC4)c3F)s2)c1]

The title material was prepared as described in Example 12 using 1H-benzo[d]imidazole-6-carboxylic acid. LC/MS (M+H)+: 679. HPLC ret. time (Condition C): 4.465 min. HRMS calcd: 679.2074; found: 679.2105.

EXAMPLE 20

3-Fluoro-N-((1-(2-hydroxy-2-phenylacetyl)-4-phenylpiperidin-4-yl)methyl)-4-(2-(4-methylpyridin-2-ylamino)thiazol-5-ylthio)picolinamide

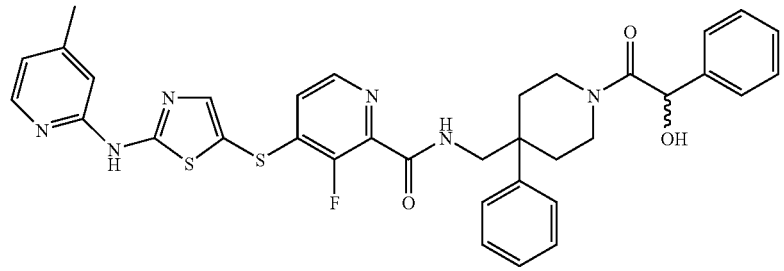 [SMILES: Cc1ccnc(Nc2ncc(Sc3ccnc(C(=O)NCC4(c5ccccc5)CCN(C(=O)C(O)c5ccccc5)CC4)c3F)s2)c1]

The title material was prepared as described in Example 12 using 2-hydroxy-2-phenylacetic acid. LC/MS (M+H)+: 669. HPLC ret. time (Condition C): 5.890 min. HRMS calcd: 669.2118; found: 669.2129.

EXAMPLE 21

N-((1-benzoyl-4-phenylpiperidin-4-yl)methyl)-3-fluoro-4-(2-(4-methylpyridin-2-ylamino)thiazol-5-ylthio)picolinamide

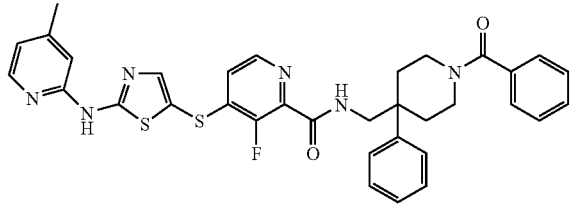 [SMILES: Cc1ccnc(Nc2ncc(Sc3ccnc(C(=O)NCC4(c5ccccc5)CCN(C(=O)c5ccccc5)CC4)c3F)s2)c1]

The title material was prepared as described in Example 12 using benzoic acid. LC/MS (M+H)+: 639. HPLC ret. time (Condition C): 6.121 min. HRMS calcd: 639.2012; found: 639.2025.

EXAMPLE 22

N-((1-acetyl-4-phenylpiperidin-4-yl)methyl)-3-fluoro-4-(2-(4-methylpyridin-2-ylamino)thiazol-5-ylthio)picoliamide

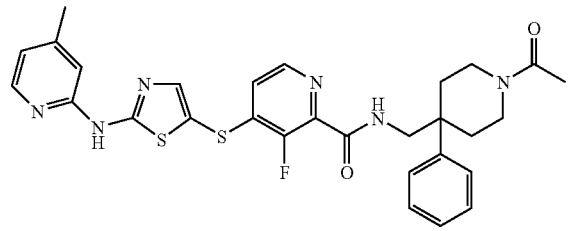 [SMILES: CC(=O)N1CCC(CNC(=O)c2nccc(Sc3cnc(Nc4cc(C)ccn4)s3)c2F)(c2ccccc2)CC1]

3-Fluoro-4-(2-(4-methylpyridin-2-ylamino)thiazol-5-ylthio)-N-((4-phenylpiperidin-4-yl)methyl)picolinamide (crude from deprotection of 3-fluoro-4-(2-(4-methylpyridin-2-ylamino)thiazol-5-ylthio)-N-((4-phenylpiperidin-4-yl)methyl)picolinamide, 0.042 g, 0.066 mmol) was dissolved in NMP (1 mL) and treated with acetyl chloride (0.007 g, 0.086 mmol) and diisopropylethylamine (0.059 mL, 0.331 mmol). The reaction was stirred at 23° C. overnight, then diluted with 10% water in acetonitrile+0.5% TFA. This was purified by preparative HPLC (water/acetonitrile/TFA) and the resulting TFA salt was dissolved in DMF and applied on a SCX SPE cartridge (Waters Oasis™), washed with methanol and eluted with 2M ammonia/methanol/THF. After concentration, the resulting solid (0.0214 g, 0.037 mmol, 55%) was suspended in acetonitrile and treated with a 0.1N HCl/methanol solution (0.370 mL). The solution was diluted with water and concentrated on speedvac to give the title material as the HCl salt. $^1$H NMR (400 MHz, DMSO-d6) δ ppm: 1.72 (1H, ddd, J=13.8, 10.2 and 3.8 Hz), 1.82 (1H, ddd, J=13.3, 9.7 and 3.8 Hz), 2.06-2.17 (2H, m), 2.15 (3H, s), 2.31 (3H, s), 2.86-2.94 (2H, m), 3.07-3.14 (1H, m), 3.45 (2H, d, J=6.32 Hz), 3.60-3.69 (1H, m), 3.88-3.95 (1H, m), 6.86 (1H, d, J=5.56 Hz), 6.93 (1H, s), 7.03 (1H, t, J=5.3 Hz), 7.07-7.12 (1H, m), 7.20-7.28 (2H, m), 7.33-7.46 (3H, m), 7.81 (1H, s), 8.17 (1H, d, J=5.31 Hz), 8.21 (1H, d, J=5.01 Hz), 11.84 (1H, s). LC/MS (M+H)+: 577. HPLC ret. time (Condition C): 5.371 min. HRMS calcd: 577.1856; found: 577.1877.

EXAMPLE 23

3-Fluoro-4-(2-(4-methylpyridin-2-ylamino)thiazol-5-ylthio)-N-(piperidin-4-ylmethyl)picolinamide

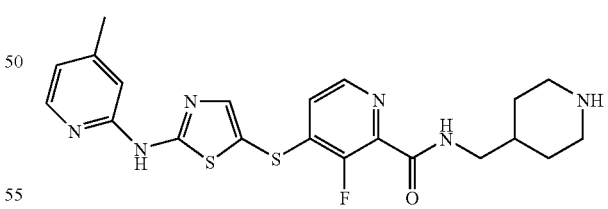

A solution of tert-butyl 4-((3-fluoro-4-(2-(4-methylpyridin-2-ylamino)thiazol-5-ylthio)picolinamido)methyl)piperidine-1-carboxylate (0.78 g, 1.40 mmol, described in Example 3) in dichloromethane (4 mL) and trifluoroacetic acid (4 mL) was stirred at 23° C. for 1 hour. The reaction was then concentrated to dryness and diluted with 10% water in acetonitrile+0.05% trifluoroacetic acid. This was purified on Preparative HPLC (acetonitrile/water/ammonium acetate) to give the title material (0.292 g, 45%) as a solid. $^1$H NMR (400 MHz, DMSO-d6) δ ppm: 1.12-1.23 (2H, m), 1.69 (2H, d, J=11.9 Hz), 2.31 (3H, s), 2.56-2.65 (2H, m), 3.08 (2H, d, J=12.4 Hz), 3.15 (2H, t, J=6.19 Hz), 6.86 (1H, d, J=5.31 Hz), 6.92 (1H, s), 7.06 (1H, t, J=5.31 Hz), 7.82 (1H, s), 8.17 (1H, d, J=5.30 Hz), 8.26 (1H, d, J=5.05 Hz), 8.74 (1H, t, J=6.06 Hz). LC/MS (M+H)+: 459. HPLC ret. time (Condition C): 3.333 min.

EXAMPLE 24

3-Fluoro-4-(2-(4-methylpyridin-2-ylamino)thiazol-5-ylthio)-N-((1-(methylsulfonyl)-4-phenylpiperidin-4-yl)methyl)picolinamide

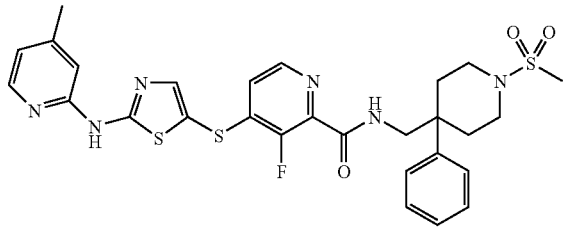 [SMILES: Cc1ccnc(Nc2ncc(Sc3ccnc(C(=O)NCC4(c5ccccc5)CCN(S(C)(=O)=O)CC4)c3F)s2)c1]

3-Fluoro-4-(2-(4-methylpyridin-2-ylamino)thiazol-5-ylthio)-N-((4-phenylpiperidin-4-yl)methyl)picolinamide (crude from deprotection of 3-fluoro-4-(2-(4-methylpyridin-2-ylamino)thiazol-5-ylthio)-N-((4-phenylpiperidin-4-yl)methyl)picolinamide, 0.042 g, 0.066 mmol) was diluted in NMP (1 mL) and treated with methanesulfonyl chloride (0.010 g, 0.086 mmol) and diisopropylethylamine (0.059 mL, 0.331 mmol) at 23° C. The reaction was stirred overnight, then diluted in 10% water in acetonitrile+0.05% TFA and purified on preparative HPLC (acetonitrile/water/trifluoroacetic acid). The fractions containing the desired product were evaporated and the residue was diluted with DMF and applied on a SCX SPE cartridge. This was washed with methanol and eluted with 2M ammonia/methanol/THF. The fractions containing the desired product were concentrated to give a solid (0.0129 g, 32%) which was triturated with ethyl ether, suspended in acetonitrile and treated with a 0.1N hydrochloric acid/methanol solution (0.210 mL). The solution was diluted with water and concentrated on speedvac to give the HCl salt of the title material. $^1$H NMR (400 MHz, DMSO-d6) δ ppm: 1.92 (1H, ddd, J=13.58, 10.04 and 3.41 Hz), 2.25 (2H, dd, J=13.14 and 3.79 Hz), 2.31 (3H, s), 2.76-2.84 (4H, m), 2.86 (3H, s), 6.84-6.88 (1H, br d), 6.93 (1H, s), 7.03 (1H, t, J=5.31 Hz), 7.11-7.16 (2H, m), 7.23-7.29 (2H, m), 7.36-7.45 (3H, m), 7.81 (1H, s), 8.17 (1H, d, J=5.05 Hz), 8.22 (1H, d, J=5.05 Hz), 8.28 (1H, t, J=6.32 Hz), 11.84 (1H, s). LC/MS (M+H)+: 613. HPLC ret. time (Condition C): 5.588 min.

EXAMPLE 25

N-((1-(cyclopropylmethyl)-4-phenylpiperidin-4-yl)methyl)-3-fluoro-4-(2-(4-methylpyridin-2-ylamino)thiazol-5-ylthio)picolinamide

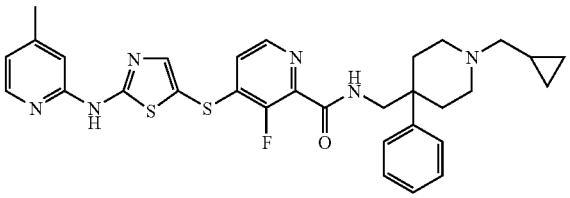 [SMILES: Cc1ccnc(Nc2ncc(Sc3ccnc(C(=O)NCC4(c5ccccc5)CCN(CC5CC5)CC4)c3F)s2)c1]

3-Fluoro-4-(2-(4-methylpyridin-2-ylamino)thiazol-5-ylthio)-N-((4-phenylpiperidin-4-yl)methyl)picolinamide (0.050 g, 0.0935 mmol, described in Example 11) was dissolved in DMF (3 mL) and treated with trimethylorthoformate (3 mL). Cyclopropanecarbaldehyde (0.065 g, 0.935 mmol) and acetic acid (3 drops) were then added and the reaction was stirred at 23° C. for 1.5 hours. The reaction was then treated with sodium triacetoxyborohydride (0.059 g, 0.281 mmol) and the reaction was stirred at 23° C. overnight. Water and acetic acid were added and after 15 minutes of stirring, this was extracted with ethyl acetate/THF. The combined extracts were dried over anhydrous magnesium sulfate, filtered and concentrated. The residue was purified by Biotage silica gel chromatography (5%-20% methanol in dichloromethane) to give the title material which was converted to the corresponding HCl salt using 0.1HCl in methanol. The desired compound was obtained as an HCl salt (0.058 g, 33%) as a solid. $^1$H NMR (400 MHz, DMSO-d6, free base) δ ppm: 0.07 (2H, s), 0.46 (2H, s), 0.81 (1H, s), 1.86-2.35 (6H, m), 2.31 (3H, s), 2.61 (1H, m), 2.68 (1H, m), 2.73 (1H, s), 2.90 (1H, s), 3.37-3.47 (2H, m), 6.86 (1H, d, J=5.30 Hz), 6.92 (1H, s), 7.04 (1H, t, J=5.43 Hz), 7.23 (1H, t, J=6.82 Hz), 7.35-7.42 (4H, m), 7.79-7.82 (1H, m), 8.16 (1H, t, J=5.94 Hz), 8.21 (1H, d, J=5.05 Hz), 11.82 (1H, s). LC/MS (M+H)+: 589. HPLC ret. time (Condition C): 4.788 min.

EXAMPLE 26

3-Fluoro-4-(2-(4-methylpyridin-2-ylamino)thiazol-5-ylthio)-N-((4-phenyl-1-(tetrahydro-2H-pyran-4-yl)piperidin-4-yl)methyl) picolinamide

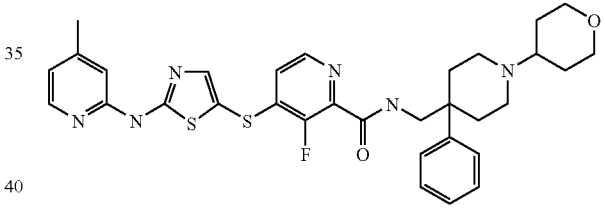

The title material was prepared as described in Example 25 using dihydro-2H-pyran-4(3H)-one. LC/MS (M+H)+: 619. HPLC ret. time (Conditions C): 4.378 min. HRMS calcd: δ 619.2325; found: 619.2317.

EXAMPLE 27

3-Fluoro-N-((1-(3-hydroxypropyl)-4-phenylpiperidin-4-yl)methyl)-4-(2-(4-methylpyridin-2-ylamino)thiazol-5-ylthio)picolinamide

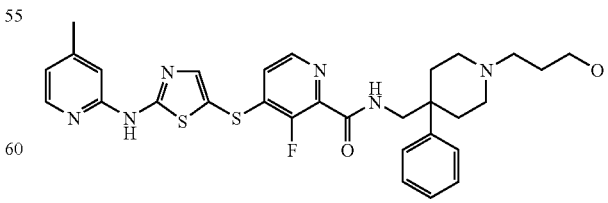

The title material was prepared as described in Example 25 using 3-(tert-butyldimethylsilyloxy)propanal. LC/MS (M+H)+: 593. HPLC ret. time (Condition C): 4.128 min. HRMS calcd: 593.2169; found: 593.2159.

EXAMPLE 28

3-Fluoro-N-((1-(3-fluoropropyl)-4-phenylpiperidin-4-yl)methyl)-4-(2-(4-methylpyridin-2-ylamino)thiazol-5-ylthio)picolinamide

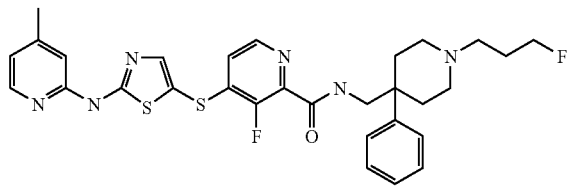 [SMILES: Cc1ccnc(Nc2ncc(Sc3ccnc(C(=O)NCC4(c5ccccc5)CCN(CCCF)CC4)c3F)s2)c1]

A. Synthesis of 3-fluoropropanal

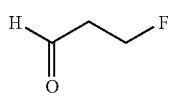

To a stirred solution of 3-fluoropropanol (0.32 g, 4.1 mmol) was added Dess-Martin reagent (1.3 g, 3.0 mmol) at 23° C. The reaction was stirred for 5 days and was used as such without any purification.

B. Synthesis of 3-fluoro-N-((1-(3-fluoropropyl)-4-phenylpiperidin-4-yl)methyl)-4-(2-(4-methylpyridin-2-ylamino)thiazol-5-ylthio)picolinamide

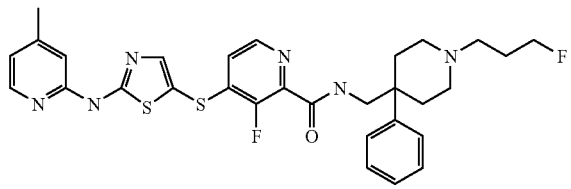 [SMILES: Cc1ccnc(Nc2ncc(Sc3ccnc(C(=O)NCC4(c5ccccc5)CCN(CCCF)CC4)c3F)s2)c1]

The title material was prepared as described in Example 25 using the solution of 3-fluoropropanal prepared above and sodium cyanoborohydride. LC/MS (M+H)+: 595. HPLC ret. time (Condition C): 4.520 min.

EXAMPLE 29

N-((1-cyclopropyl-4-phenylpiperidin-4-yl)methyl)-3-fluoro-4-(2-(4-methylpyridin-2-ylamino)thiazol-5-ylthio)picolinamide

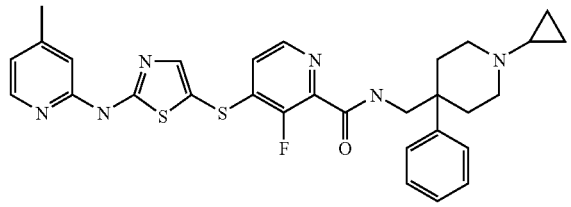 [SMILES: Cc1ccnc(Nc2ncc(Sc3ccnc(C(=O)NCC4(c5ccccc5)CCN(C5CC5)CC4)c3F)s2)c1]

3-Fluoro-4-(2-(4-methylpyridin-2-ylamino)thiazol-5-ylthio)-N-((4-phenylpiperidin-4-yl)methyl)picolinamide (0.150 g, 0.281 mmol, described in Example 11) was dissolven methanol (10 mL) and acetic acid (5 drops). Molecular sieves were added (powder, 200 mgs), followed by (1-ethoxycyclopropoxy)trimethylsilane (0.696 g, 4.0 mmol) and sodium cyanoborohydride (0.125 g, 2.0 mmol). The reaction was stirred at 23° C. for 10 minutes and then refluxed for 3 hours. The mixture was then applied on MCX cartridge, washed with water and methanol and eluted with ammonia in methanol and dichloromethane. After evaporation of the solvents, the residue was dissolved in methanol and treated with HCl (0.1N in methanol). The solvent was evaporated and the compound was lyophilized to give the HCl salt of the title material (0.043 g, 25%) as a solid. $^1$H NMR (400 MHz, DMSO-d6, free base) δ ppm: 0.25 (2H, s), 0.35 (1H, d, J=4.3 Hz), 1.42-1.50 (1H, m), 1.74-1.85 (2H, m), 2.08 (2H, br d), 2.25-2.36 (2H, m), 2.31 (3H, s), 2.65-2.77 (2H, m), 3.41 (2H, d, J=5.8 Hz), 6.86 (1H, d, J=5.31 Hz), 6.92 (1H, s), 7.03 (1H, t, J=5.31H), 7.23 (1H, t, J=6.57 Hz), 7.34-7.45 (4H, m), 7.80 (1H, s), 8.10 (1H, br t), 8.19 (2H, dd, J=12.51 and 4.93 Hz), 11.80 (1H, s). LC/MS (M+H)+: 575. HPLC ret. time (Condition C): 4.541 min.

EXAMPLE 30

N-((1-(cyanomethyl)-4-phenylpiperidin-4-yl)methyl)-3-fluoro-4-(2-(4-methylpyridin-2-ylamino)thiazol-5-ylthio)picolinamide

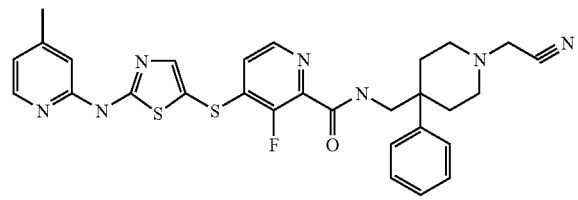 [SMILES: Cc1ccnc(Nc2ncc(Sc3ccnc(C(=O)NCC4(c5ccccc5)CCN(CC#N)CC4)c3F)s2)c1]

3-Fluoro-4-(2-(4-methylpyridin-2-ylamino)thiazol-5-ylthio)-N-((4-phenylpiperidin-4-yl)methyl)picolinamide (0.150 g, 0.281 mmol, described in Example 11) was diluted in THF and treated with triethylamine (0.153 mL, 1.124 mmol) and bromoacetonitrile (0.059 mL, 0.843 mmol). The reaction was stirred at 100° C. with microwaves for 30 minutes and then the solvent was evaporated. The residue was purified by preparative HPLC (acetonitrile/water/ammonium acetate) and the fractions containing the desired product were lyophilized. The resulting residue was dissolved in methanol and treated with 0.1N HCl in methanol (1 eq.). The solvent was evaporated and water was added. The solution was lyophilized to give the HCl salt of the starting material (0.051 g, 30%) as a solid. $^1$H NMR (400 MHz, DMSO-d6, free base) δ ppm: 1.85-1.96 (2H, m), 2.17 (2H, d, J=14.4 Hz), 2.24-2.35 (2H, m), 2.31 (3H, s), 2.60-2.69 (2H, m), 3.41 (2H, d, J=6.32 Hz), 3.64 (2H, s), 6.86 (1H, d, J=5.05 Hz), 6.92 (1H, s), 7.03 (1H, t, J=5.31 Hz), 7.24 (1H, t, J=6.95 Hz), 7.34-7.45 (4H, m), 7.81 (1H, s), 8.13-8.19 (2H, m), 8.21 (1H, d, J=5.05 Hz), 11.77 (1H, s). LC/MS (M+H)+: 574. HPLC ret. time (Condition C): 4.615 min. HRMS calcd: 574.1859; found: 574.1843.

EXAMPLE 31

3-Fluoro-N-((1-(2-methoxyethyl)-4-phenylpiperidin-4-yl)methyl)-4-(2-(4-methylpyridin-2-ylamino)thiazol-5-ylthio)picolinamide

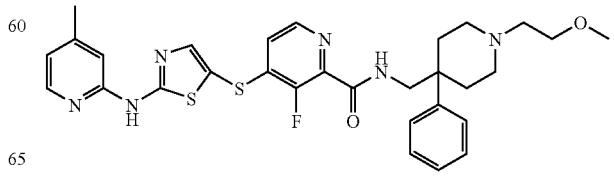

The title material was prepared as described in Example 30 using 1-bromo-2-methoxyethane. LC/MS (M+H)⁺: 593. HPLC ret. time (Condition C): 4.473 min. HRMS calcd: 593.2169; found: 593.2178.

EXAMPLE 32

3-Fluoro-4-(2-(4-methylpyridin-2-yl)amino)thiazol-5-ylthio)-N-((4-phenyl-1-(3,3,3-trifluoropropyl)piperidin-4-yl)methyl)picolinamide

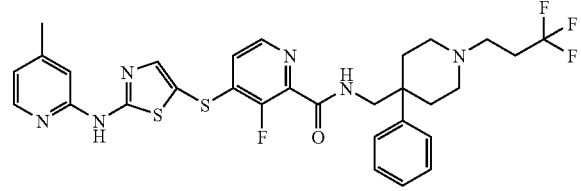 [SMILES: Cc1ccnc(Nc2ncc(Sc3ccnc(C(=O)NCC4(c5ccccc5)CCN(CCC(F)(F)F)CC4)c3F)s2)c1]

The title material was prepared as described in Example 30 using 3-bromo-1,1,1-trifluoropropane. LC/MS (M+H)⁺: 631. HPLC ret. time (Condition C): 4.908 min. HRMS calcd: 631.1937; found: 631.1945.

EXAMPLE 33

N-((1-(2-cyanoethyl)-4-phenylpiperidin-4-yl)methyl)-3-fluoro-4-(2-(4-methylpyridin-2-ylamino)thiazol-5-ylthio)picolinamide

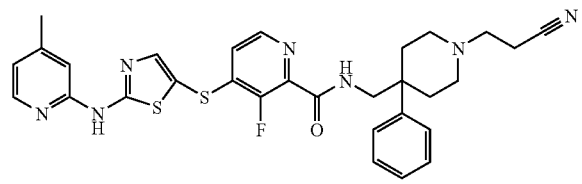 [SMILES: Cc1ccnc(Nc2ncc(Sc3ccnc(C(=O)NCC4(c5ccccc5)CCN(CCC#N)CC4)c3F)s2)c1]

3-Fluoro-4-(2-(4-methylpyridin-2-ylamino)thiazol-5-ylthio)-N-((4-phenylpiperidin-4-yl)methyl)picolinamide (0.150 g, 0.281 mmol, described in Example 11) was dissolved in methanol (6 mL) and treated with diisopropylethylamine (0.490 mL, 2.81 mmol). The reaction was cooled to 0° C. and acrylonitrile (0.037 mL, 0.562 mmol) was added. The reaction was stirred at 23° C. for 30 minutes and then purified by preparative HPLC (acetonitrile/water/ammonium acetate). The fractions containing the desired product were lyophilized. The resulting residue was dissolved in methanol and treated with 0.1N HCl in methanol (1 eq). The solvent was evaporated, water was added and this was lyophilized to give the HCl salt of the title material (0.058 g, 33%) as a solid. ¹H NMR (400 MHz, DMSO-d6, free base) δ ppm: 1.83-1.94 (2H, m), 2.08-2.19 (4H, m), 2.31 (3H, s), 2.43-2.48 (2H, m), 2.59-2.70 (2H, m), 2.62 (2H, t, J=6.69 Hz), 3.42 (2H, d, J=6.32 Hz), 6.86 (1H, d, J=5.31 Hz), 6.92 (1H, s), 7.03 (1H, t, J=5.31 Hz), 7.22 (1H, t, J=6.69 Hz), 7.34-7.41 (4H, m), 7.80 (1H, s), 8.12 (1H, t, J=6.32 Hz), 8.19 (2H, dd, J=14.15 and 5.05 Hz), 11.80 (1H, s). LC/MS (M+H)⁺: 588. HPLC ret. time (Condition C): 4.361 min. HRMS calcd: 588.2016; found: 588.2022.

EXAMPLE 34

3-Fluoro-4-(2-(4-methylpyridin-2-ylamino)thiazol-5-ylthio)-N-((1-(2-(methylsulfonyl)ethyl)-4-phenylpiperidin-4-yl)methyl)picolinamide

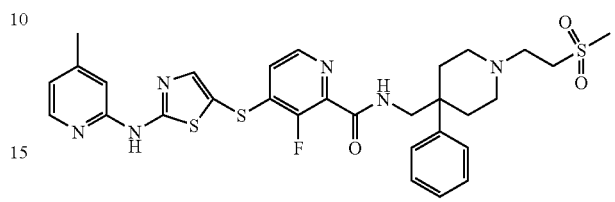

The title material was prepared as described in Example 33 using methylsulfonylethene. LC/MS (M+H)⁺: 641. HPLC ret. time (Condition C): 4.321 min. HRMS calcd: 641.1839; found: 641.1819.

EXAMPLE 35

3-Fluoro-N-4-(2-hydroxy-2-methylpropyl)-4-phenylpiperidin-4-yl)methyl)-4-(2-(4-methylpyridin-2-ylamino)thiazol-5-ylthio)picolinamide

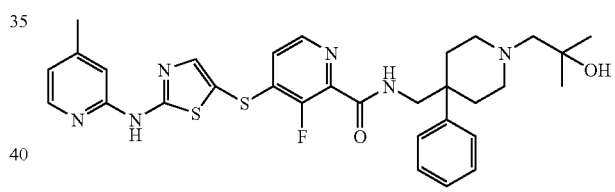

3-Fluoro-4-(2-(4-methylpyridin-2-ylamino)thiazol-5-ylthio)-N-((4-phenylpiperidin-4-yl)methyl)picolinamide (0.100 g, 0.187 mmol, described in Example 11) was dissolved in methanol (10 mL) and treated with triethylamine (0.051 mL, 0.374 mmol) and 2,2-dimethyloxirane (~20 drops, excess). The reaction was stirred at 23° C. overnight. The solvent was then evaporated and the residue was purified by preparative HPLC (acetonitrile/water/ammonium acetate) and the fractions containing the desired compound were lyophilized to give the title material (0.022 g, 19%) as a solid. This was dissolved in methanol and treated with HCl (0.1N in MeOH, 0.36 mL, 0.0363 mmol). The solvent was evaporated, water was added and the mixture was lyophilized to give the HCl salt of the title material (0.028 g) as a solid. ¹H NMR (400 MHz, DMSO-d6, free base) δ ppm: 1.05 (6H, s), 1.83-1.94 (2H, m), 2.03-2.14 (4H, m), 2.25-2.36 (2H, m), 2.31 (3H, s), 2.64-2.74 (2H, m), 3.43 (2H, d, J=6.32 Hz), 6.86 (1H, d, J=5.31 Hz), 6.92 (1H, s), 7.03 (1H, t, J=5.18 Hz), 7.22 (1H, t, J=6.44 Hz), 7.32-7.34 (4H, m), 7.80 (1H, s), 8.03 (1H, t, J=6.19 Hz), 8.18 (2H, dd, J=10.48 and 5.18 Hz). LC/MS (M+H)⁺: 607. HPLC ret. time (Condition C): 4.386 min. HRMS calcd: 607.2325; found: 607.2319.

EXAMPLE 36

3-Fluoro-N-((1-(2-hydroxyethyl)-4-phenylpiperidin-4-yl)methyl)-4-(2-(5-((methylamino)methyl)pyridin-2-ylamino)thiazol-5-ylthio)picolinamide

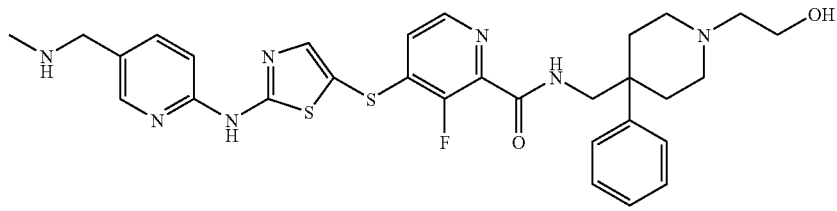 [SMILES: CNCc1ccc(Nc2ncc(Sc3ccnc(C(=O)NCC4(c5ccccc5)CCN(CCO)CC4)c3F)s2)nc1]

A. Synthesis of methyl 4-(2-(5-((tert-butoxycarbonyl(methyl)amino)methyl)pyridin-2-ylamino)thiazol-5-ylthio)-3-fluoropicolinate

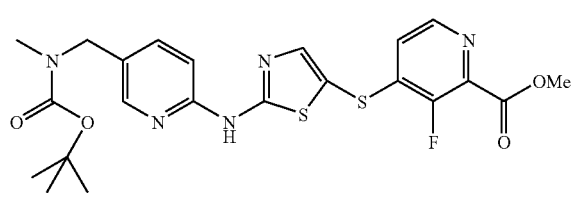 [SMILES: COC(=O)c1nccc(Sc2cnc(Nc3ccc(CN(C)C(=O)OC(C)(C)C)cn3)s2)c1F]

A solution of tert-butyl methyl ((6-(5-thiocyanatothiazol-2-ylamino)pyridine-3-yl)methyl)carbamate (100 mg, 0.265 mmol, described in the synthesis of thiocyanates Example C, Table 2) in methanol (10 mL) was bubbled with Ar for 15 minutes. Dithiothreitol (1.3 eq, 0.344 mmol, 53 mg) was then added and the solution was stirred at 23° C. for 15 minutes. This was treated with methyl 4-chloro-3-fluoropicolinate (0.265 mmol, 50 mg) and a solution of 0.1 mmol/mL of potassium phosphate in water (0.106 mmol, 0.4 eq, 1.06 mL). The reaction was stirred at 23° C. for 2 hours and then concentrated to ¼ of the volume by rotavap. The reaction was diluted in water (40 mL) and neutralized with a saturated solution of ammonium chloride. The solid was collected by filtration to give the title material (94 mg, 70%) as a solid. $^1$H NMR (400 MHz, DMSO-d6) δ ppm: 1.41 (9H, s), 2.76 (3H, s), 3.91 (3H, s), 4.33 (2H, s), 7.06-7.21 (2H, m), 7.67 (1H, d, J=8.84 Hz) 7.84 (1H, s) 8.20 (1H, d, J=1.77 Hz) 8.33 (1H, d, J=5.05 Hz) 11.92 (1H, s). LC/MS (M+H)$^+$: 506. Ret. time: 1.98 min. (Condition A).

B. Synthesis of 4-(2-(5-((tert-butoxycarbonyl(methyl)amino)methyl)pyridin-2-ylamino)thiazol-5-ylthio)-3-fluoropicolinic acid

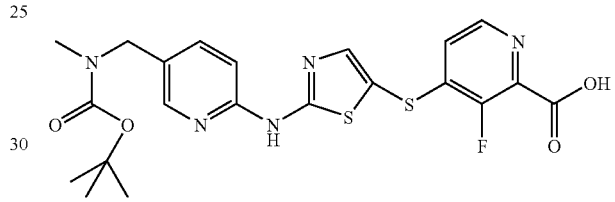

A solution of methyl 4-(2-(5-((tert-butoxycarbonyl(methyl)amino)methyl)pyridin-2-ylamino)thiazol-5-ylthio)-3-fluoropicolinate (2.56 g, 5.06 mmol) in THF (100 mL) was treated with NaOH 5N (6 eq, 30.4 mmol, 6 mL) and stirred at 23° C. for 10 min. Water (10 mL) was added to the mixture which was them stirred at 23° C. for 2 hours. The mixture was then acidified with HCl conc. to pH=4. Water was added and the aqueous phase was extracted with EtOAc (3×). The combined organic extracts were washed with brine, dried over MgSO$_4$, filtered and evaporated to give the crude title material (2.59 g) as a solid. $^1$H NMR (400 MHz, DMSO-d6) δ ppm: 1.41 (9H, s), 2.75 (3H, s), 4.33 (2H, s), 7.04-7.18 (2H, m) 7.66 (1H, d, J=7.33 Hz) 7.84 (1H, s) 8.20 (1H, d, J=1.52 Hz) 8.30 (1H, d, J=4.80 Hz) 11.92 (1H, s). LC/MS (M+H)$^+$: 492. Ret. time: 1.308 min. (Condition B).

C. Synthesis of tert-butyl (6-(5-(3-fluoro-2-((1-(2-hydroxyethyl)-4-phenylpiperidin-4-yl)methylcarbamoyl)pyridin-4-ylthio)thiazol-2-ylamino)pyridin-3-yl)methyl(methyl)carbamate

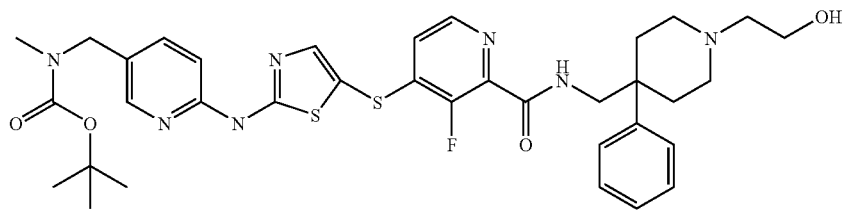 [SMILES: CN(Cc1ccc(Nc2ncc(Sc3ccnc(C(=O)NCC4(c5ccccc5)CCN(CCO)CC4)c3F)s2)nc1)C(=O)OC(C)(C)C]

4-(2-(5-((Tert-butoxycarbonyl(methyl)amino)methyl)pyridin-2-ylamino)thiazol-5-ylthio)-3-fluoropicolinic acid (0.120 g, 0.244 mmol) was diluted in NMP (4 mL) and treated with HOBT (0.043 g, 0.317 mmol), EDAC (0.094 g, 0.488 mmol) and 2-(4-(aminomethyl)-4-phenylpiperidin-1-yl)ethanol (0.074 g, 0.317 mmol) and diisopropylethylamine (0.213 mL, 1.22 mmol) at 23° C. The reaction was stirred overnight then water was added and this was extracted with ethyl acetate/THF (3×). The organic extracts were dried over anhydrous magnesium sulfate, filtered and concentrated to give a residue which was purified on preparative HPLC (acetonitrile/water/TFA). The title material was obtained (0.140 g, ~81%) as a solid which was used as such for the next step. LC/MS (M+H)+: 708. Ret. time: 1.612 min. (Condition F).

D. Synthesis of 3-fluoro-N-((1-(2-hydroxyethyl)-4-phenylpiperidin-4-yl)methyl)-4-(2-(5-((methylamino)methyppyridin-2-ylamino)thiazol-5-ylthio)picolinamide

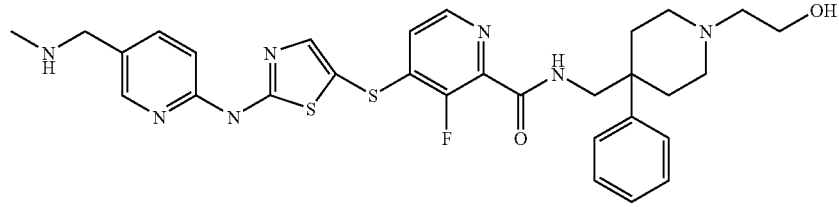 [SMILES: CNCc1ccc(Nc2ncc(Sc3ccnc(C(=O)NCC4(c5ccccc5)CCN(CCO)CC4)c3F)s2)nc1]

Tert-butyl (6-(5-(3-fluoro-2-((1-(2-hydroxyethyl)-4-phenylpiperidin-4-yl)methylcarbamoyl)pyridin-4-ylthio)thiazol-2-ylamino)pyridin-3-yl)methyl(methyl)carbamate (0.140 g, ~0.198 mmol) was dissolved in 20% TFA in dichloromethane (10 mL) at 23° C. The reaction was stirred for 2 hours, then neutralized with aq. sat. sodium carbonate to pH~7. Water was then added and this was extracted with ethyl acetate/THF (2×). The combined organic extracts were dried over anhydrous magnesium sulfate, filtered and concentrated. The residue was purified by preparative HPLC (water/acetonitrile/TFA) and the fractions containing the desired product were lyophilized. The residue was dissolved in methanol and stirred with resin MP Carbonate. After filtration, the resulting solution was treated with 0.1N HCl in methanol. The solvent was evaporated, water was added and this was lyophilized to give the HCl salt of the title material (0.016 g, 13%) as a solid. 1H NMR (400 MHz, DMSO-d6) δ ppm: 1.82-1.93 (2H, m), 2.02-2.23 (4H, m), 2.25-2.34 (2H, m), 2.29 (3H, s), 2.60-2.69 (2H, m), 3.13-3.20 (2H, m), 3.38-3.47 (2H, m), 3.67 (s, 2H), 4.10 (1H, br s), 4.35 (1H, br s), 7.03 (1H, t, J=5.31 Hz), 7.09 (1H, d, J=8.59 Hz), 7.22 (1H, t, J=7.07 Hz), 7.33-7.42 (4H, m), 7.76 (1H, dd, J=8.59 and 2.27 Hz), 7.82 (1H, s), 8.08-8.16 (1H, m), 8.21 (1H, d, J=5.05 Hz), 8.24 (1H, d, J=1.77 Hz), LC/MS (M+H)+: 608. Ret. time: 3.078 min. (Condition C). HRMS calcd: 608.2278; found: 608.2305.

EXAMPLE 37 tert-butyl 4-((3-fluoro-4-(2-(4-methylpyridin-2-ylamino)thiazol-5-ylthio)picolinamido)methyl)-4-(pyridin-4-yl)piperidine-1-carboxylate

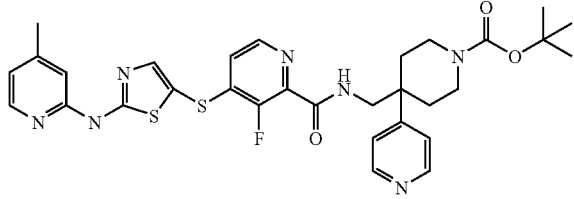 [SMILES: Cc1ccnc(Nc2ncc(Sc3ccnc(C(=O)NCC4(c5ccncc5)CCN(C(=O)OC(C)(C)C)CC4)c3F)s2)c1]

3-Fluoro-4-(2-(4-methylpyridin-2-ylamino)thiazol-5-ylthio)picolinic acid (intermediate B in example 1, 612 mg, 1.7 mmol), tert-butyl 4-(aminomethyl)-4-(pyridin-4-yl)piperidine-1-carboxylate (amine intermediate "L", 640 mg, 2.2 mmol), EDAC (649 mg, 3.4 mmol), HOBt (297 mg, 2.8 mmol) and diisopropyl-ethyl-amine (1.47 ml, 8.4 mmol) were dissolved in 15 ml NMP and stirred until LCMS showed complete consumption of acid starting material. (usually overnight) The product was precipitated out of the reaction mixture by addition of water, filtered, rinsed with water and dried. The title compound was isolated as a solid (1.01 g, 90% pure by HPLC, 83% yield). An analytical sample was purified by prep HPLC (C-18 reversed phase column, water/MeOH gradient, buffered with 0.1% TFA). Alternatively a water/acetonitrile gradient, buffered with 10 mM NH4OAc can be used. Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. of 1.00 N HCl were added and the title compound was isolated as the mono-HCl salt by evaporation. LC/MS (M+H)+: 636. Ret. time: 1.66 min. (Condition M); analytical HPLC Ret. time: 16.74 min (Condition N).

EXAMPLE 38 tert-butyl 4-((3-fluoro-4-(2-(4-methylpyridin-2-ylamino)thiazol-5-ylthio)picolinamido)methyl)-4-(pyridin-3-yl)piperidine-1-carboxylate

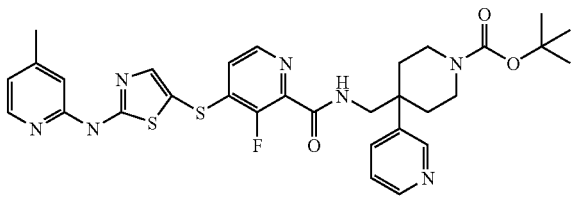 [SMILES: Cc1ccnc(Nc2ncc(Sc3ccnc(C(=O)NCC4(c5cccnc5)CCN(C(=O)OC(C)(C)C)CC4)c3F)s2)c1]

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-(pyridin-3-yl)piperidine-1-carboxylate (amine intermediate "M") were reacted to give the title compound. LC/MS (M+H)+: 636. Ret. time: 1.53 min. (Condition G); analytical HPLC Ret. time: 6.11 min (Condition H).

EXAMPLE 39

3-fluoro-4-(2-(4-methylpyridin-2-ylamino)thiazol-5-ylthio)-N-((4-phenyltetrahydro-2H-pyran-4-yl)methyl)picolinamide

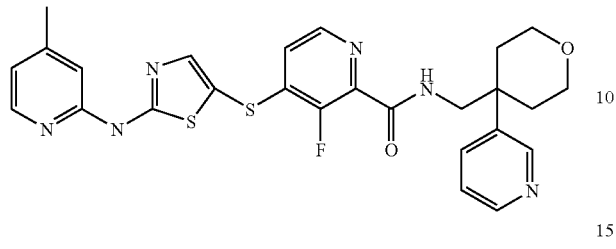

Following the amide bond forming procedure given in example 37, 3-fluoro-4-(2-(4-methylpyridin-2-ylamino)thiazol-5-ylthio)picolinic acid (intermediate B in example 1) and (4-phenyltetrahydro-2H-pyran-4-yl)methanamine (amine intermediate "X") were reacted to give the title compound. LC/MS (M+H)+: 536. Ret. time: 1.59 min. (Condition G); analytical HPLC Ret. time: 7.85 min (Condition H)

EXAMPLE 40

N-((1-(3,4-dimethoxyphenyl)cyclohexyl)methyl)-3-fluoro-4-(2-(4-methylpyridin-2-ylamino)thiazol-5-ylthio)picolinamide

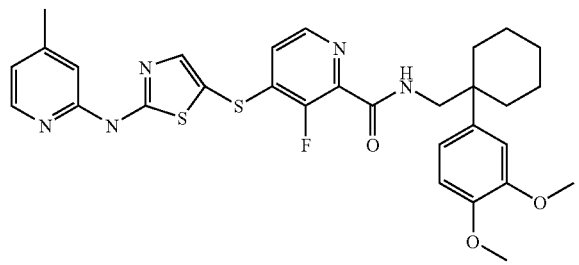 [SMILES: COc1ccc(C2(CNC(=O)c3nccc(Sc4cnc(Nc5cc(C)ccn5)s4)c3F)CCCCC2)cc1OC]

Following the amide bond forming procedure given in example 37, 3-fluoro-4-(2-(4-methylpyridin-2-ylamino)thiazol-5-ylthio)picolinic acid (intermediate B in example 1) and 1-(3,4-dimethoxyphenyl)cyclohexyl)methanamine (amine intermediate "Y") were reacted to give the title compound. LC/MS (M+H)+: 594. Ret. time: 1.85 min. (Condition G); analytical HPLC Ret. time: 8.95 min (Condition H).

EXAMPLE 41

3-fluoro-N-((1-(4-fluorophenyl)-4-hydroxycyclohexyl)methyl)-4-(2-(4-methylpyridin-2-ylamino)thiazol-5-ylthio)picolinamide

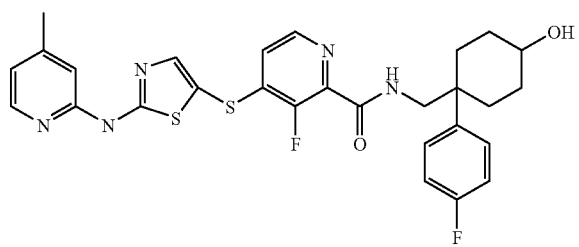 [SMILES: Cc1ccnc(Nc2ncc(Sc3ccnc(C(=O)NCC4(c5ccc(F)cc5)CCC(O)CC4)c3F)s2)c1]

Following the amide bond forming procedure given in example 37, 3-fluoro-4-(2-(4-methylpyridin-2-ylamino)thiazol-5-ylthio)picolinic acid (intermediate B in example 1) and 4-(aminomethyl)-4-(4-fluorophenyl)cyclohexanol (amine intermediate "T") were reacted to give the title compound. LC/MS (M+H)+: 568. Ret. time: 1.51 min. (Condition G); analytical HPLC Ret. time: 8.11 min (Condition H).

EXAMPLE 42

3-fluoro-N-((4-(2-fluorophenyl)-1-methylpiperidin-4-yl)methyl)-4-(2-(4-methylpyridin-2-ylamino)thiazol-5-ylthio)picolinamide

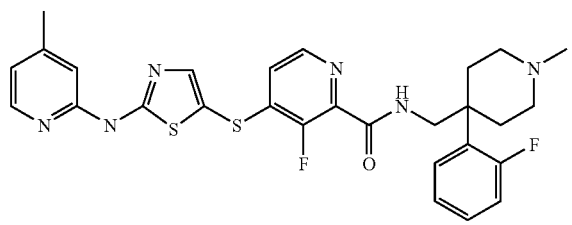 [SMILES: Cc1ccnc(Nc2ncc(Sc3ccnc(C(=O)NCC4(c5ccccc5F)CCN(C)CC4)c3F)s2)c1]

The compound was prepared following the amide bond forming procedure given in example 37, 3-fluoro-4-(2-(4-methylpyridin-2-ylamino)thiazol-5-ylthio)picolinic acid (intermediate B in example 1) and (4-(2-fluorophenyl)-1-methylpiperidin-4-yl)methanamine (amine intermediate "Z") were reacted to give the title compound. LC/MS (M+H)+: 567. Ret. time: 1.45 min. (Condition G); analytical HPLC Ret. time: 5.83 min (Condition H).

EXAMPLE 43

(3-fluoro-4-(2-(4-methylpyridin-2-ylamino)thiazol-5-ylthio)pyridin-2-yl)(isoindolin-2-yl)methanone

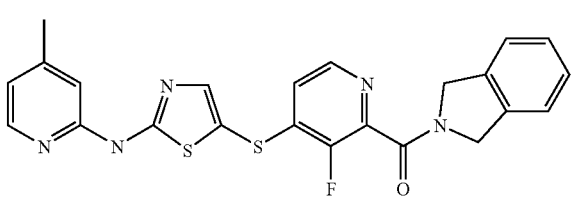 [SMILES: Cc1ccnc(Nc2ncc(Sc3ccnc(C(=O)N4Cc5ccccc5C4)c3F)s2)c1]

Following the amide bond forming procedure given in example 37, 3-fluoro-4-(2-(4-methylpyridin-2-ylamino)thiazol-5-ylthio)picolinic acid (intermediate B in example 1) and isoindoline were reacted to give the title compound. LC/MS (M+H)+: 464. Ret. time: 1.66 min. (Condition M); analytical HPLC Ret. time: 17.03 min (Condition N).

EXAMPLE 44 tert-butyl 4-cyclohexyl-4-((3-fluoro-4-(2-(4-methylpyridin-2-ylamino)thiazol-5-ylthio)picolinamido)methyl)piperidine-1-carboxylate

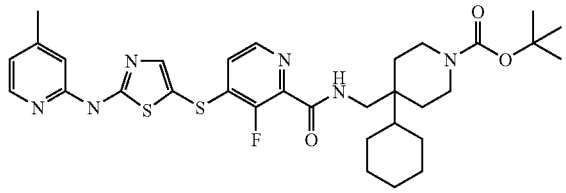 [SMILES: Cc1ccnc(Nc2ncc(Sc3ccnc(C(=O)NCC4(C5CCCCC5)CCN(C(=O)OC(C)(C)C)CC4)c3F)s2)c1]

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-cyclohexylpiperidine-1-carboxylate (amine intermediate "R") were reacted to give the title compound. LC/MS (M+H)$^+$: 641. Ret. time: 2.18 min. (Condition L); analytical HPLC Ret. time: 12.41 min (Condition O).

EXAMPLE 45

3-fluoro-4-(2-(4-methylpyridin-2-ylamino)thiazol-5-ylthio)-N-((4-(pyridin-4-yl)piperidin-4-yl)methyl)picolinamide

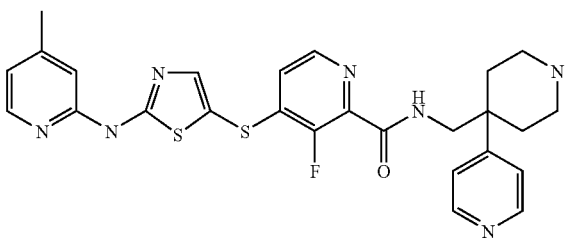 [SMILES: Cc1ccnc(Nc2ncc(Sc3ccnc(C(=O)NCC4(c5ccncc5)CCNCC4)c3F)s2)c1]

Tert-butyl 4-((3-fluoro-4-(2-(4-methylpyridin-2-ylamino)thiazol-5-ylthio)picolinamido)methyl)-4-(pyridin-4-yl)piperidine-1-carboxylate (compound example 37, 1.0 g, 1.4 mmol) was dissolved in a mixture of 30 ml 1,2-Dichloroethane and 10 ml TFA and stirred at room temperature for 18 hours. Evaporation of volatiles gave crude title compound, which could be used for further derivatization without purification. Analytical and biological samples were purified by prep HPLC (C-18 reversed phase column, water/MeOH gradient, buffered with 0.1% TFA). Alternatively a water/acetonitrile gradient, buffered with 10 mM NH$_4$OAc can be used. Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. 1.00 N HCl were added and the title compound was isolated as the mono-HCl salt by evaporation. LC/MS (M+H)$^+$: 536. Ret. time: 0.99 min. (Condition L); analytical HPLC Ret. time: 4.40 min (Condition O).

EXAMPLE 46

3-fluoro-4-(2-(4-methylpyridin-2-ylamino)thiazol-5-ylthio)-N-((4-(pyridin-3-yl)piperidin-4-yl)methyl)picolinamide

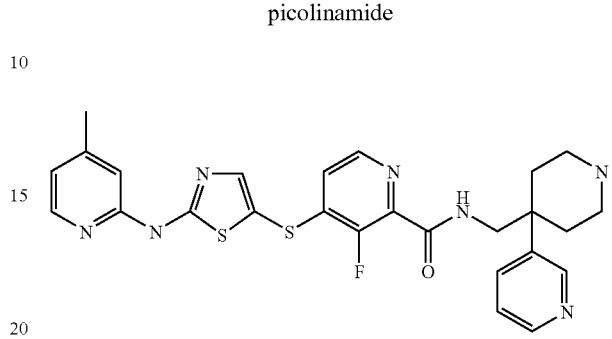

Tert-butyl 4-((3-fluoro-4-(2-(4-methylpyridin-2-ylamino)thiazol-5-ylthio)picolinamido)methyl)-4-(pyridin-3-yl)piperidine-1-carboxylate (compound example 38) was deprotected using the procedure described for example 45 to give the title compound. LC/MS (M+H)$^+$: 536. Ret. time: 1.18 min. (Condition G); analytical HPLC Ret. time: 4.34 min (Condition H).

EXAMPLE 47

3-fluoro-4-(2-(4-methylpyridin-2-ylamino)thiazol-5-ylthio)-N-((4-(pyridin-2-yl)piperidin-4-yl)methyl)picolinamide

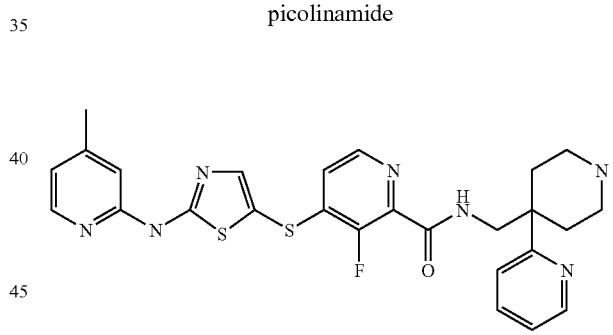

A. Synthesis of tert-butyl 4-((3-fluoro-4-(2-(4-methylpyridin-2-ylamino)thiazol-5-ylthio)picolinamido)methyl)-4-(pyridin-2-yl)piperidine-1-carboxylate

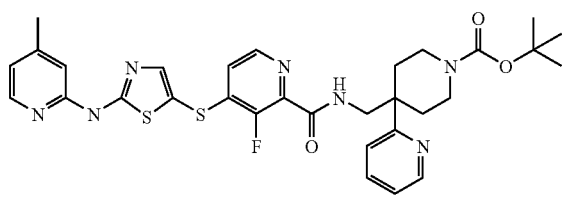 [SMILES: Cc1ccnc(Nc2ncc(Sc3ccnc(C(=O)NCC4(c5ccccn5)CCN(C(=O)OC(C)(C)C)CC4)c3F)s2)c1]

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-(pyridin-2-yl)piperidine-1- carboxylate (amine intermediate "N") were reacted to give the title compound. LC/MS (M+H)+: 636. Ret. time: 1.69 min. (Condition I).

B. Synthesis of 3-fluoro-4-(2-(4-methylpyridin-2-ylamino)thiazol-5-ylthio)-N-((4-(pyridin-2-yl)piperidin-4-yl)methyl)picolinamide

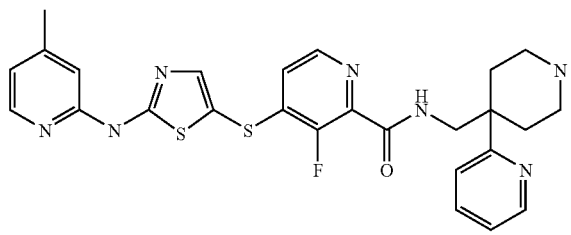 [SMILES: Cc1ccnc(Nc2ncc(Sc3ccnc(C(=O)NCC4(c5ccccn5)CCNCC4)c3F)s2)c1]

Tert-butyl 4-((3-fluoro-4-(2-(4-methylpyridin-2-ylamino)thiazol-5-ylthio)picolinamido)methyl)-4-(pyridin-2-yl)piperidine-1-carboxylate was deprotected following the procedure described for example 45 to give the title compound. LC/MS (M+H)+: 536. Ret. time: 1.24 min. (Condition I); analytical HPLC Ret. time: 5.92 min (Condition H).

EXAMPLE 48

N-((4-(3,4-dichlorophenyl)piperidin-4-yl)methyl)-3-fluoro-4-(2-(4-methylpyridin-2-ylamino)thiazol-5-ylthio)picolinamide

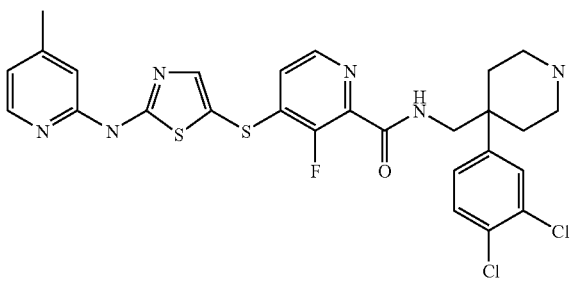 [SMILES: Cc1ccnc(Nc2ncc(Sc3ccnc(C(=O)NCC4(c5ccc(Cl)c(Cl)c5)CCNCC4)c3F)s2)c1]

A. Synthesis of tert-butyl 4-(3,4-dichlorophenyl)-4-((3-fluoro-4-(2-(4-methylpyridin-2-ylamino)thiazol-5-ylthio)picolinamido)methyl)piperidine-1-carboxylate

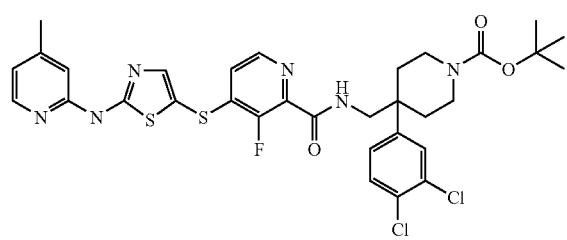 [SMILES: Cc1ccnc(Nc2ncc(Sc3ccnc(C(=O)NCC4(c5ccc(Cl)c(Cl)c5)CCN(C(=O)OC(C)(C)C)CC4)c3F)s2)c1]

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-(3,4-dichlorophenyl)piperidine-1-carboxylate (amine intermediate "K") were reacted to give the title compound. LC/MS (M+H)+: 703. Ret. time: 2.20 min. (Condition I).

B. Synthesis of N-((4-(3,4-dichlorophenyl)piperidin-4-yl)methyl)-3-fluoro-4-(2-(4-methylpyridin-2-ylamino)thiazol-5-ylthio)picolinamide

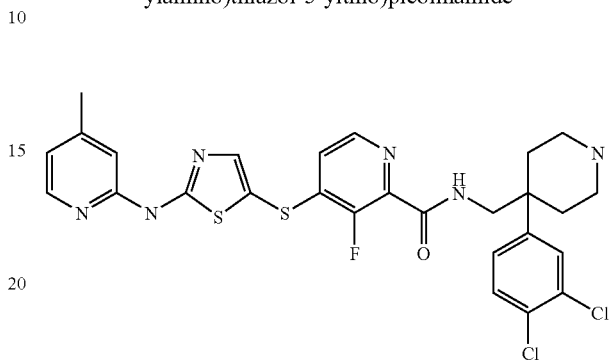

Tert-butyl 4-(3,4-dichlorophenyl)-4-((3-fluoro-4-(2-(4-methylpyridin-2-ylamino)thiazol-5-ylthio)picolinamido)methyl)piperidine-1-carboxylate was deprotected following the procedure described for example 45 to give the title compound. LC/MS (M+H)+: 603. Ret. time: 1.69 min. (Condition I); analytical HPLC Ret. time: 6.59 min (Condition H).

EXAMPLE 49

N-((4-(2,3-dichlorophenyl)piperidin-4-yl)methyl)-3-fluoro-4-(2-(4-methylpyridin-2-ylamino)thiazol-5-ylthio)picolinamide

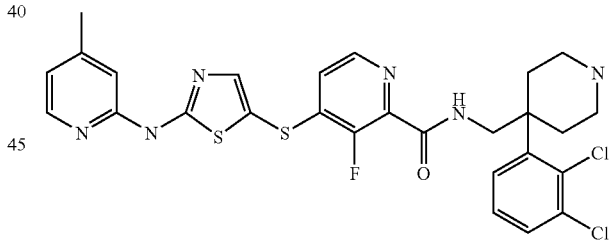

A. Synthesis of tert-butyl 4-(2,3-dichlorophenyl)-4-(3-fluoro-4-(2-(4-methylpyridin-2-ylamino)thiazol-5-ylthio)picolinamido)methyl)piperidine-1-carboxylate

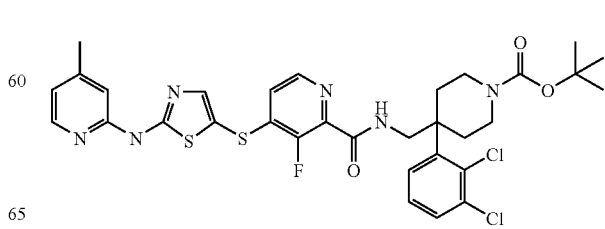

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-(2,3-dichlorophenyl)piperidine-1-carboxylate (amine intermediate "J") were reacted to give the title compound. LC/MS (M+H)$^+$: 703. Ret. time: 2.01 min. (Condition M).

B. Synthesis of N-((4-(2,3-dichlorophenyl)piperidin-4-yl)methyl)-3-fluoro-4-(2-(4-methylpyridin-2-ylamino)thiazol-5-ylthio)picolinamide

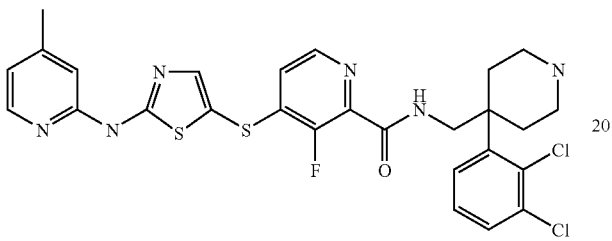

Tert-butyl 4-(2,3-dichlorophenyl)-4-((3-fluoro-4-(2-(4-methylpyridin-2-ylamino)thiazol-5-ylthio)picolinamido)methyl)piperidine-1-carboxylate was deprotected following the procedure described for example 45 to give the title compound. LC/MS (M+H)$^+$: 603. Ret. time: 1.64 min. (Condition L); analytical HPLC Ret. time: 6.40 min (Condition H).

EXAMPLE 50

N-((4-(2,3-dichlorophenyl)-1-methyl)piperidin-4-yl)methyl)-3-fluoro-4-(2-(4-methylpyridin-2-ylamino)thiazol-5-ylthio)picolinamide

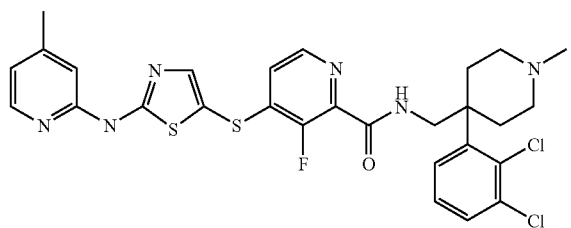 [SMILES: Cc1ccnc(Nc2ncc(Sc3ccnc(C(=O)NCC4(c5cccc(Cl)c5Cl)CCN(C)CC4)c3F)s2)c1]

N-((4-(2,3-dichlorophenyl)piperidin-4-yl)methyl)-3-fluoro-4-(2-(4-methylpyridin-2-ylamino)thiazol-5-ylthio)picolinamide (example 49, 29 mg, 0.048 mmol) was dissolved in 5 ml MeOH+5 ml THF. The pH was adjusted to ~4 by addition of 0.01 ml acetic acid (if starting material was free base) or addition of sodium acetate (5 equiv., if starting material was TFA salt). Trimethylorthoformate (0.5 ml) was added, followed by 0.05 ml formaldehyde (37% aqueous solution, ~0.6 mmol). The mixture was stirred at room temperature for 5 minutes, then NaBH$_3$CN (30 mg, 0.475 mmol) was added and the mixture stirred at room temperature for 1 hour. The crude reaction mixture was filtered through a cartridge filled with cation exchange resin (MCX from Waters or STRATA X-C from Phenomenex), rinsed with methanol, eluted with 2 M solution of ammonia in methanol and evaporated. The crude product was purified by prep HPLC (C-18 reversed phase column, water/MeOH gradient, buffered with 0.1% TFA). Alternatively a water/acetonitrile gradient, buffered with 10 mM NH$_4$OAc can be used. Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. 1.00 N HCl were added and the title compound was isolated as the mono-HCl salt by evaporation. LC/MS (M+H)$^+$: 617. Ret. time: 1.61 min. (Condition L); analytical HPLC Ret. time: 6.44 min (Condition H).

EXAMPLE 51

3-fluoro-N-((4-(4-fluorophenyl)-1-methylpiperidin-4-yl)methyl)-4-(2-(4-methylpyridin-2-ylamino)thiazol-5-ylthio)picolinamide

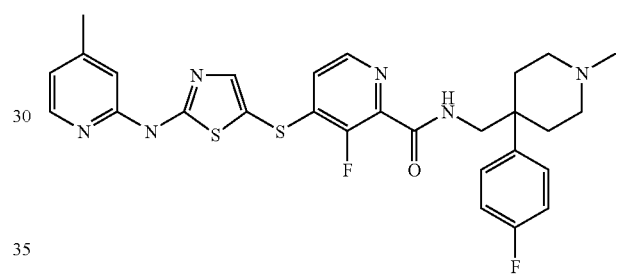

A. Synthesis of tert-butyl 4-((3-fluoro-4-(2-(4-methylpyridin-2-ylamino)thiazol-5-ylthio)picolinamido)methyl)-4-(4-fluorophenyl)piperidine-1-carboxylate

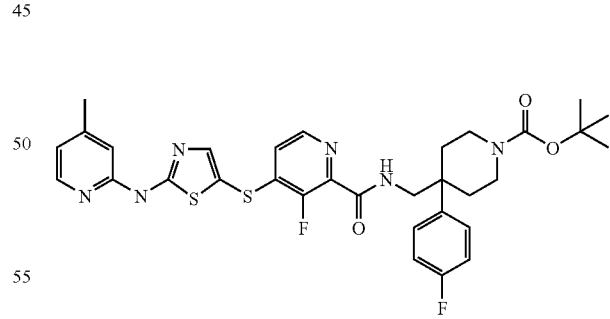

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-(4-fluorophenyl)piperidine-1-carboxylate (amine intermediate "P") were reacted to give the title compound. LC/MS (M+H)$^+$: 653. Ret. time: 2.06 min. (Condition L).

B. Synthesis of 3-fluoro-N-((4-(4-(4-fluorophenyl)piperidin-4-yl)methyl)-4-(2-(4-methylpyridin-2-ylamino)thiazol-5-ylthio)picolinamide

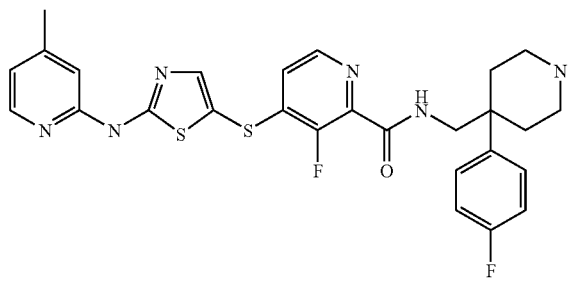 [SMILES: Cc1ccnc(Nc2ncc(Sc3ccnc(C(=O)NCC4(c5ccc(F)cc5)CCNCC4)c3F)s2)c1]

Tert-butyl 4-((3-fluoro-4-(2-(4-methylpyridin-2-ylamino)thiazol-5-ylthio)picolinamido)methyl)-4-(4-fluorophenyl)piperidine-1-carboxylate was deprotected following the procedure described for example 45 to give the title compound. LC/MS (M+H)+: 553. Ret. time: 1.49 min. (Condition L).

C. Synthesis of 3-fluoro-N-β4-(4-fluorophenyl)-1-methylpiperidin-4-yl)methyl)-4-(2-(4-methylpyridin-2-ylamino)thiazol-5-ylthio)picolinamide

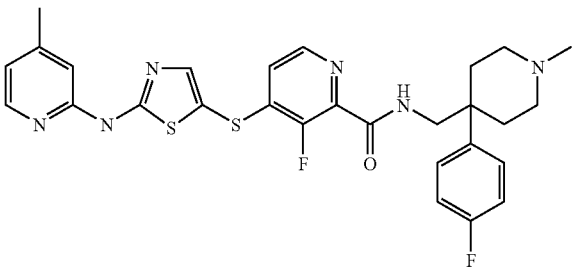 [SMILES: Cc1ccnc(Nc2ncc(Sc3ccnc(C(=O)NCC4(c5ccc(F)cc5)CCN(C)CC4)c3F)s2)c1]

Following the procedure given for example 50, 3-fluoro-N-((4-(4-fluorophenyl)piperidin-4-yl)methyl)-4-(2-(4-methylpyridin-2-ylamino)thiazol-5-ylthio)picolinamide was converted into the title compound. LC/MS (M+H)+: 567. Ret. time: 1.63 min. (Condition M); analytical HPLC Ret. time: 16.89 min (Condition N).

EXAMPLE 52

N-((4-(2,4-difluorophenyl)-1-methylpiperidin-4-yl)methyl)-3-fluoro-4-(2-(4-methylpyridin-2-ylamino)thiazol-5-ylthio)picolinamide

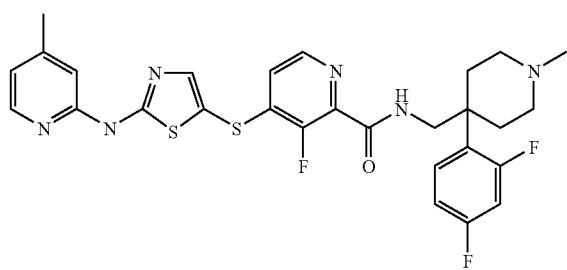 [SMILES: Cc1ccnc(Nc2ncc(Sc3ccnc(C(=O)NCC4(c5ccc(F)cc5F)CCN(C)CC4)c3F)s2)c1]

A. Synthesis of tert-butyl 4-(2,4-difluorophenyl)-4-((3-fluoro-4-(2-(4-methylpyridin-2-ylamino)thiazol-5-ylthio)picolinamido)methyl)piperidine-1-carboxylate

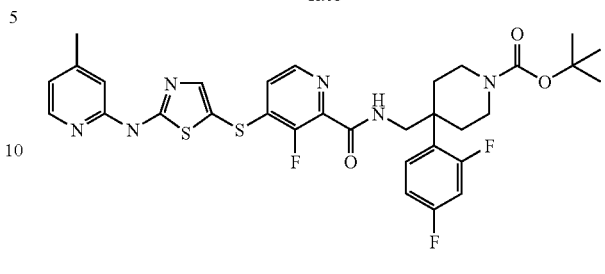

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-(2,4-difluorophenyl)piperidine-1-carboxylate (amine intermediate "Q") were reacted to give the title compound. LC/MS (M+H)+: 671. Ret. time: 2.07 min. (Condition L).

B. Synthesis of N-((4-(2,4-difluorophenyl)piperidin-4-yl)methyl)-3-fluoro-4-(2-(4-methylpyridin-2-ylamino)thiazol-5-ylthio)picolinamide

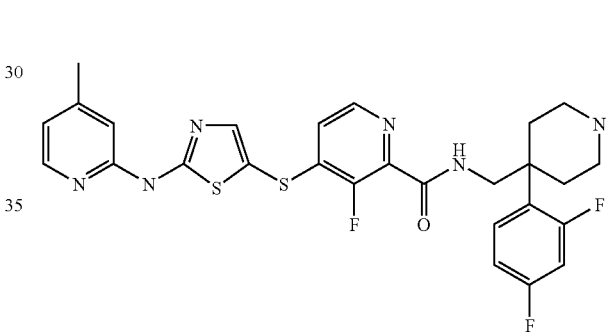

Tert-butyl 4-(2,4-difluorophenyl)-4-((3-fluoro-4-(2-(4-methylpyridin-2-ylamino)thiazol-5-ylthio)picolinamido)methyl)piperidine-1-carboxylate was deprotected following the procedure described for example 45 to give the title compound. LC/MS (M+H)+: 571. Ret. time: 1.51 min. (Condition L).

C. Synthesis of N-((4-(2,4-difluorophenyl)-1-methylpiperidin-4-yl)methyl)-3-fluoro-4-(2-(4-methylpyridin-2-ylamino)thiazol-5-ylthio)picolinamide

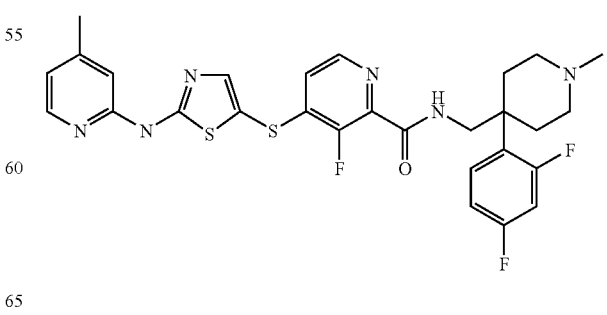

Following the procedure given for example 50, N-((4-(2,4-difluorophenyl)piperidin-4-yl)methyl)-3-fluoro-4-(2-(4- methylpyridin-2-ylamino)thiazol-5-ylthio)picolinamide was converted into the title compound. LC/MS (M+H)+: 585. Ret. time: 1.63 min. (Condition M); analytical HPLC Ret. time: 16.96 min (Condition N).

EXAMPLE 53

N-((4-cyclohexyl-1-methylpiperidin-4-yl)methyl)-3-fluoro-4-(2-(4-methylpyridin-2-ylamino)thiazol-5-ylthio)picolinamide

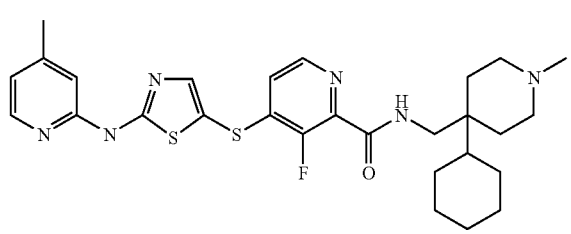 [SMILES: Cc1ccnc(Nc2ncc(Sc3ccnc(C(=O)NCC4(C5CCCCC5)CCN(C)CC4)c3F)s2)c1]

A. Synthesis of N-((4-cyclohexylpiperidin-4-yl)methyl)-3-fluoro-4-(2-(4-methylpyridin-2-ylamino)thiazol-5-ylthio)picolinamide

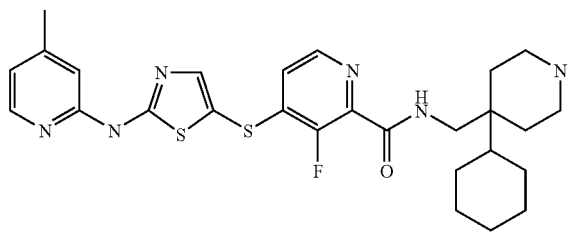 [SMILES: Cc1ccnc(Nc2ncc(Sc3ccnc(C(=O)NCC4(C5CCCCC5)CCNCC4)c3F)s2)c1]

Tert-butyl 4-cyclohexyl-4-((3-fluoro-4-(2-(4-methylpyridin-2-ylamino)thiazol-5-ylthio)picolinamido)methyl)piperidine-1-carboxylate (compound example 44) was deprotected following the procedure described for example 45 to give the title compound. LC/MS (M+H)+: 541. Ret. time: 1.64 min. (Condition L).

B. Synthesis of N-((4-cyclohexyl-1-methylpiperidin-4-yl)methyl)-3-fluoro-4-(2-(4-methylpyridin-2-ylamino)thiazol-5-ylthio)picolinamide

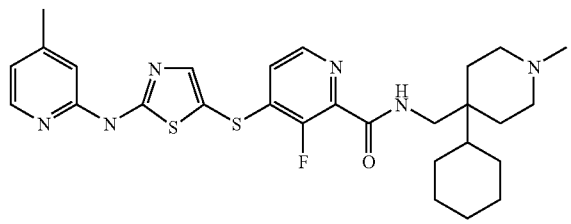 [SMILES: Cc1ccnc(Nc2ncc(Sc3ccnc(C(=O)NCC4(C5CCCCC5)CCN(C)CC4)c3F)s2)c1]

Following the procedure given for example 50, N-((4-cyclohexylpiperidin-4-yl)methyl)-3-fluoro-4-(2-(4-methylpyridin-2-ylamino)thiazol-5-ylthio)picolinamide was converted into the title compound. LC/MS (M+H)+: 555. Ret. time: 1.92 min. (Condition M); analytical HPLC Ret. time: 17.64 min (Condition N).

EXAMPLE 54

3-fluoro-N-((1-methyl-4-(5-methylisoxazol-3-yl)piperidin-4-yl)methyl)-4-(2-(4-methylpyridin-2-ylamino)thiazol-5-ylthio)picolinamide

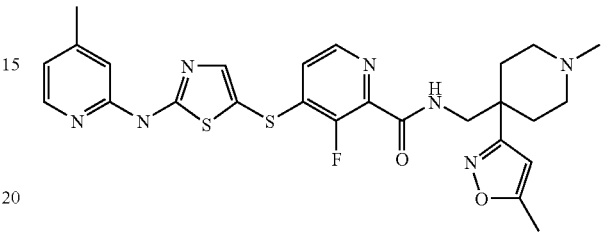

A. Synthesis of tert-butyl 4-((3-fluoro-4-(2-(4-methylpyridin-2-ylamino)thiazol-5-ylthio)picolinamido)methyl)-4-(5-methylisoxazol-3-yl)piperidine-1-carboxylate

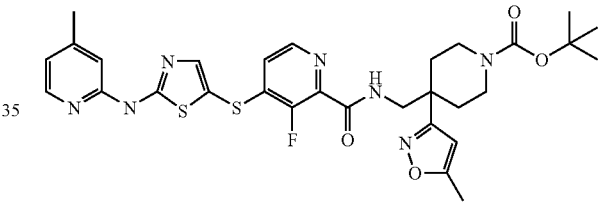

Following the amide bond forming procedure given in example 37, 3-fluoro-4-(2-(4-methylpyridin-2-ylamino)thiazol-5-ylthio)picolinic acid (intermediate B in example 1) and tert-butyl 4-(aminomethyl)-4-(5-methylisoxazol-3-yl)piperidine-1-carboxylate (amine intermediate "S") were reacted to give the title compound. LC/MS (M+H)+: 640. Ret. time: 1.89 min. (Condition L).

B. Synthesis of 3-fluoro-N-((4-(5-methylisoxazol-3-yl)piperidin-4-yl)methyl)-4-(2-(4-methylpyridin-2-ylamino)thiazol-5-ylthio)picolinamide

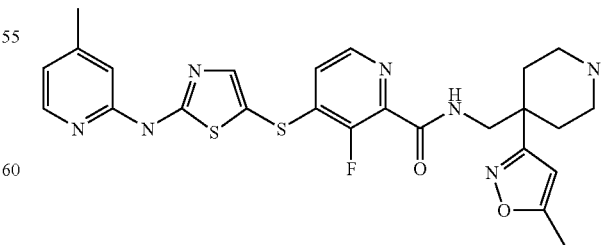

Tert-butyl 4-((3-fluoro-4-(2-(4-methylpyridin-2-ylamino)thiazol-5-ylthio)picolinamido)methyl)-4-(5-methylisoxazol-3-yl)piperidine-1-carboxylate was deprotected follow- C. Synthesis of 3-fluoro-N-((1-methyl-4-(5-methyl-isoxazol-3-yl)piperidin-4-yl)methyl)-4-(2-(4-methylpyridin-2-ylamino)thiazol-5-ylthio)picolinamide

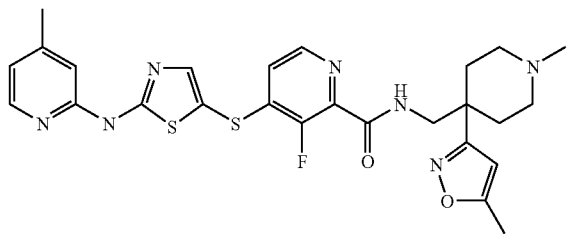 [SMILES: Cc1ccnc(Nc2ncc(Sc3ccnc(C(=O)NCC4(c5cc(C)on5)CCN(C)CC4)c3F)s2)c1]

Following the procedure given for example 50, 3-fluoro-N-((4-(5-methylisoxazol-3-yl)piperidin-4-yl)methyl)-4-(2-(4-methylpyridin-2-ylamino)thiazol-5-ylthio)picolinamide was converted into the title compound. LC/MS (M+H)+: 554. Ret. time: 1.30 min. (Condition L); analytical HPLC Ret. time: 16.09 min (Condition N).

EXAMPLE 55

N-((1-(cyanomethyl)-4-(5-methylisoxazol-3-yl)piperidin-4-yl)methyl)-3-fluoro-4-(2-(4-methylpyridin-2-ylamino)thiazol-5-ylthio)picolinamide

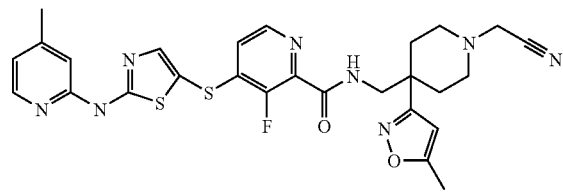 [SMILES: Cc1ccnc(Nc2ncc(Sc3ccnc(C(=O)NCC4(c5cc(C)on5)CCN(CC#N)CC4)c3F)s2)c1]

Following the procedure for reductive amination given for example 50, but without the addition of sodium acetate, the TFA salt of 3-fluoro-N-((4-(5-methylisoxazol-3-yl)piperidin-4-yl)methyl)-4-(2-(4-methylpyridin-2-ylamino)thiazol-5-ylthio)picolinamide was converted into the title compound. LC/MS (M+H)+: 579. Ret. time: 1.40 min. (Condition L); analytical HPLC Ret. time: 15.39 min (Condition N).

EXAMPLE 56

3-fluoro-N-((1-(2-hydroxyethyl)-4-(pyridin-4-yl)piperidin-4-yl)methyl)-4-(2-(4-methylpyridin-2-ylamino)thiazol-5-ylthio)picolinamide

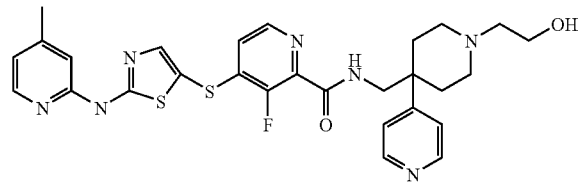 [SMILES: Cc1ccnc(Nc2ncc(Sc3ccnc(C(=O)NCC4(c5ccncc5)CCN(CCO)CC4)c3F)s2)c1]

3-Fluoro-4-(2-(4-methylpyridin-2-ylamino)thiazol-5-ylthio)-N-((4-(pyridin-4-yl)piperidin-4-yl)methyl)picolinamide (compound example 45, 50 mg, 0.093 mmol) was dissolved in 5 ml MeOH+5 ml THF. The pH was adjusted to ~4 by addition of 0.25 ml acetic acid (if starting material was free base) or addition of sodium acetate (5 equiv., if starting material was TFA salt). Trimethylorthoformate (1.0 ml) was added, followed by 91 mg 2-hydroxyacetaldehyde dimer (0.75 mmol). The mixture was stirred at room temperature for 20 minutes, then NaBH3CN (190 mg, 3.8 mmol) was added and the mixture stirred at room temperature for 1 hour. The crude reaction mixture was filtered through a cartridge filled with cation exchange resin (MCX from Waters or STRATA X-C from Phenomenex), rinsed with methanol, eluted with 2 M solution of ammonia in methanol and evaporated. The crude product was purified by prep HPLC (C-18 reversed phase column, water/MeOH gradient, buffered with 0.1% TFA). Alternatively a water/acetonitrile gradient, buffered with 10 mM NH4OAc can be used. Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. 1.00 N HCl were added and the title compound was isolated as the mono-HCl salt by evaporation. LC/MS (M+H)+: 580. Ret. time: 1.03 min. (Condition L); analytical HPLC Ret. time: 4.89 min (Condition P).

EXAMPLE 57

N-((4-(3,4-dichlorophenyl)-1-(2-hydroxyethyl)piperidin-4-yl)methyl)-3-fluoro-4-(2-(4-methylpyridin-2-ylamino)thiazol-5-ylthio)picolinamide

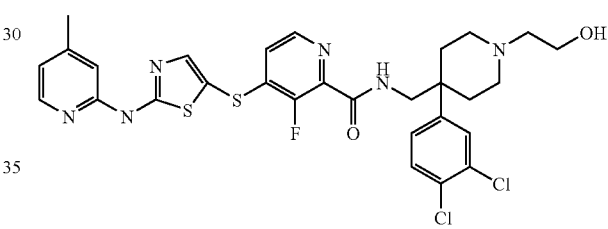

Following the procedure given for example 56, N-((4-(3,4-dichlorophenyl)piperidin-4-yl)methyl)-3-fluoro-4-(2-(4-methylpyridin-2-ylamino)thiazol-5-ylthio)picolinamide (compound example 48) was converted into the title compound. LC/MS (M+H)+: 647. Ret. time: 2.15 min. (Condition J); analytical HPLC Ret. time: 6.17 min (Condition H).

EXAMPLE 58

3-fluoro-N-((1-(2-hydroxyethyl)-4-(pyridin-2-yl)piperidin-4-yl)methyl)-4-(2-(4-methylpyridin-2-ylamino)thiazol-5-ylthio)picolinamide

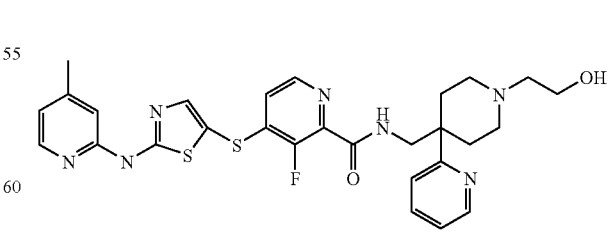

Following the procedure given for example 56, 3-fluoro-4-(2-(4-methylpyridin-2-ylamino)thiazol-5-ylthio)-N-((4-(pyridin-2-yl)piperidin-4-yl)methyl)picolinamide (compound example 47) was converted into the title compound.

LC/MS (M+H)+: 580. Ret. time: 1.72 min. (Condition J); analytical HPLC Ret. time: 4.56 min (Condition H).

EXAMPLE 59

3-fluoro-N-((1-(2-hydroxyethyl)-4-(pyridin-3-yl)piperidin-4-yl)methyl)-4-(2-(4-methylpyridin-2-ylamino)thiazol-5-ylthio)picolinamide

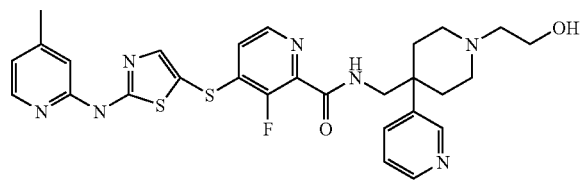 [SMILES: Cc1ccnc(Nc2ncc(Sc3ccnc(C(=O)NCC4(c5cccnc5)CCN(CCO)CC4)c3F)s2)c1]

Following the procedure given for example 56, 3-fluoro-4-(2-(4-methylpyridin-2-ylamino)thiazol-5-ylthio)-N-((4-(pyridin-3-yl)piperidin-4-yl)methyl)picolinamide (compound example 46) was converted into the title compound. LC/MS (M+H)+: 580. Ret. time: 1.13 min. (Condition G); analytical HPLC Ret. time: 4.42 min (Condition H).

EXAMPLE 60

3-fluoro-N-((1-(2-methoxyethyl)-4-(pyridin-4-yl)piperidin-4-yl)methyl)-4-(2-(4-methylpyridin-2-ylamino)thiazol-5-ylthio)picolinamide

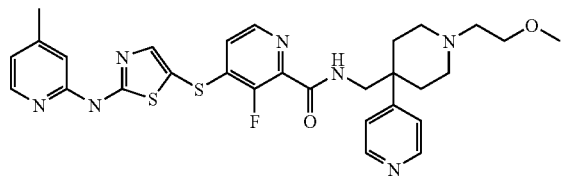 [SMILES: COCCN1CCC(CNC(=O)c2nccc(Sc3cnc(Nc4cc(C)ccn4)s3)c2F)(c2ccncc2)CC1]

A. Synthesis of 2-methoxyacetaldehyde

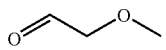

1,1,2-Trimethoxyethane (0.8 ml, 6 mmol) and aqueous HCl (1.0 N, 6 ml, 6 mmol) were combined in a microwave vial, sealed and heated to 8° C. for 10 minutes. The crude solution of the title compound was used "as is".

B. Synthesis of 3-fluoro-N-((1-(2-methoxyethyl)-4-(pyridin-4-yl)piperidin-4-yl)methyl)-4-(2-(4-methylpyridin-2-ylamino)thiazol-5-ylthio)picolinamide

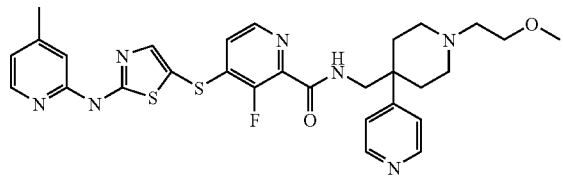 [SMILES: COCCN1CCC(CNC(=O)c2nccc(Sc3cnc(Nc4cc(C)ccn4)s3)c2F)(c2ccncc2)CC1]

3-fluoro-4-(2-(4-methylpyridin-2-ylamino)thiazol-5-ylthio)-N-((4-(pyridin-4-yl)piperidin-4-yl)methyl)picolinamide (compound example 45, 50 mg, 0.093 mmol) was dissolved in 3 ml MeOH and 3 ml THF and 1 ml of the above prepared solution of 2-methoxyacetaldehyde (~0.9 mmol). The pH was adjusted to ~5 by addition of KOAc (250 mg, 2.85 mmol). Trimethylorthoformate (3.0 ml) was added. The mixture was stirred at room temperature for 5 minutes, then NaBH3CN (50 mg, 1.0 mmol) was added and the mixture stirred at room temperature for 1 hour. The reaction mixture was poured into aq. NaHCO3 solution and extracted with dichloromethane. The organic layer was washed with brine, dried over MgSO4, filtered and concentrated in vacuo. The crude product was purified by prep HPLC (C-18 reversed phase column, water/MeOH gradient, buffered with 0.1% TFA). Alternatively a water/acetonitrile gradient, buffered with 10 mM NH4OAc can be used. Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. 1.00 N HCl were added and the title compound was isolated as the mono-HCl salt by evaporation. LC/MS (M+H)+: 594. Ret. time: 1.04 min. (Condition L); analytical HPLC Ret. time: 9.94 min (Condition N).

EXAMPLE 61

N-((4-(3,4-dichlorophenyl)-1-(2-methoxyethyl)piperidin-4-yl)methyl)-3-fluoro-4-(2-(4-methylpyridin-2-ylamino)thiazol-5-ylthio)picolinamide

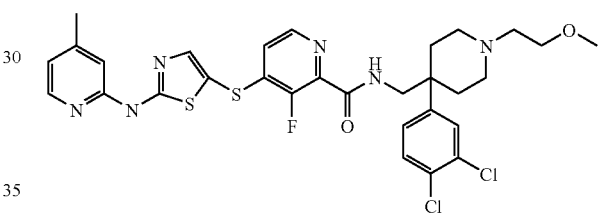

Following the procedure given for example 60, N-((4-(3,4-dichlorophenyl)piperidin-4-yl)methyl)-3-fluoro-4-(2-(4-methylpyridin-2-ylamino)thiazol-5-ylthio)picolinamide (compound example 48) was converted into the title compound. LC/MS (M+H)+: 661. Ret. time: 2.37 min. (Condition J); analytical HPLC Ret. time: 6.52 min (Condition H).

EXAMPLE 62

3-fluoro-N-((1-(2-methoxyethyl)-4-(pyridin-2-yl)piperidin-4-yl)methyl)-4-(2-(4-methylpyridin-2-ylamino)thiazol-5-ylthio)picolinamide

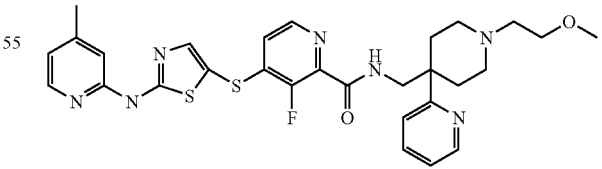

Following the procedure given for example 60, 3-fluoro-4-(2-(4-methylpyridin-2-ylamino)thiazol-5-ylthio)-N-((4-(pyridin-2-yl)piperidin-4-yl)methyl)picolinamide (compound example 47) was converted into the title compound. LC/MS (M+H)+: 594. Ret. time: 1.88 min. (Condition J); analytical HPLC Ret. time: 4.78 min (Condition H).

EXAMPLE 63

N-((4-(3,4-dichlorophenyl)-1-(3-fluoropropyl)piperidin-4-yl)methyl)-3-fluoro-4-(2-(4-methylpyridin-2-ylamino)thiazol-5-ylthio)picolinamide

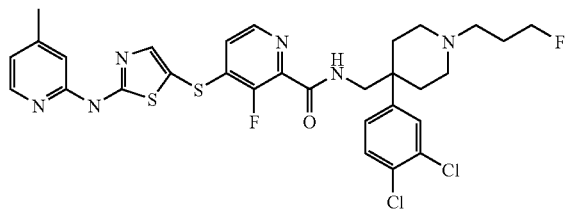 [SMILES: Cc1ccnc(Nc2ncc(Sc3ccnc(C(=O)NCC4(c5ccc(Cl)c(Cl)c5)CCN(CCCF)CC4)c3F)s2)c1]

Following the procedure given for example 28, N-((4-(3,4-dichlorophenyl)piperidin-4-yl)methyl)-3-fluoro-4-(2-(4-methylpyridin-2-ylamino)thiazol-5-ylthio)picolinamide (compound example 48) was converted into the title compound. LC/MS (M+H)$^+$: 663. Ret. time: 1.64 min. (Condition G); analytical HPLC Ret. time: 7.24 min (Condition H).

EXAMPLE 64

3-fluoro-N-((1-(3-fluoropropyl)-4-(pyridin-2-yl)piperidin-4-yl)methyl)-4-(2-(4-methylpyridin-2-ylamino)thiazol-5-ylthio)picolinamide

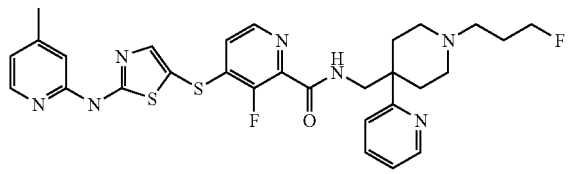 [SMILES: Cc1ccnc(Nc2ncc(Sc3ccnc(C(=O)NCC4(c5ccccn5)CCN(CCCF)CC4)c3F)s2)c1]

Following the procedure given for example 28, 3-fluoro-4-(2-(4-methylpyridin-2-ylamino)thiazol-5-ylthio)-N-((4-(pyridin-2-yl)piperidin-4-yl)methyl)picolinamide (compound example 47) was converted into the title compound. LC/MS (M+H)$^+$: 596. Ret. time: 1.32 min. (Condition G); analytical HPLC Ret. time: 5.25 min (Condition H).

EXAMPLE 65

3-fluoro-4-(2-(4-methylpyridin-2-ylamino)thiazol-5-ylthio)-N-((1-propyl-4-(pyridin-2-yl)piperidin-4-yl)methyl)picolinamide

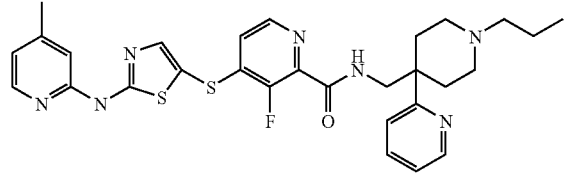 [SMILES: CCCN1CCC(CNC(=O)c2nccc(Sc3cnc(Nc4cc(C)ccn4)s3)c2F)(c2ccccn2)CC1]

The title compound was isolated as a byproduct (~5% yield) during the formation of compound example 64 as described above. LC/MS (M+H)$^+$: 578. Ret. time: 1.34 min. (Condition G); analytical HPLC Ret. time: 5.27 min (Condition H).

EXAMPLE 66

N-((4-(2,4-difluorophenyl)-1-(1,3-dihydroxypropan-2-yl)piperidin-4-yl)methyl)-3-fluoro-4-(2-(4-methylpyridin-2-ylamino)thiazol-5-ylthio)picolinamide

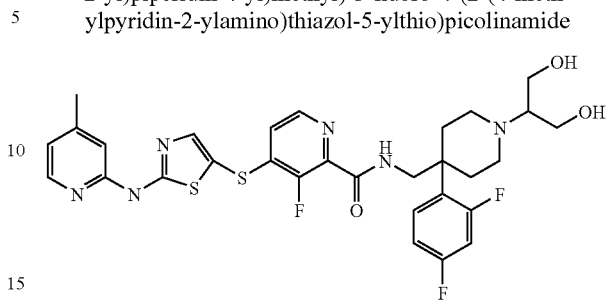

N-((4-(2,4-difluorophenyl)piperidin-4-yl)methyl)-3-fluoro-4-(2-(4-methylpyridin-2-ylamino)thiazol-5-ylthio) picolinamide (intermediate B in synthesis of example 52, 88 mg, crude TFA salt, ~0.07 mmol) was dissolved in 3 ml MeOH+3 ml THF. The pH was adjusted to ~4 by addition of sodium acetate (43 mg, 0.52 mmol) (alternatively, add 0.01 ml acetic acid if starting material was free base). Trimethylorthoformate (0.25 ml) was added, followed by dihydroxyacetone (38 mg, as its dimer, 0.42 mmol calc for monomer). The mixture was stirred at room temperature for 50 minutes, then NaBH$_3$CN (25 mg, 0.5 mmol) was added and the mixture stirred at room temperature for 18 hours. The crude reaction mixture was filtered, rinsed with methanol, eluted with 2 M solution of ammonia in methanol and evaporated. The crude product was purified by prep HPLC (C-18 reversed phase column, water/MeOH gradient, buffered with 0.1% TFA). Alternatively a water/acetonitrile gradient, buffered with 10 mM NH$_4$OAc can be used. Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. of 1.00 N HCl were added and the title compound was isolated as the mono-HCl salt by evaporation. LC/MS (M+H)$^+$: 645. Ret. time: 1.46 min. (Condition L); analytical HPLC Ret. time: 16.09 min (Condition N).

EXAMPLE 67

N-((4-cyclohexyl-1-(1,3-dihydroxypropan-2-yl)piperidin-4-yl)methyl)-3-fluoro-4-(2-(4-methylpyridin-2-ylamino)thiazol-5-ylthio)picolinamide

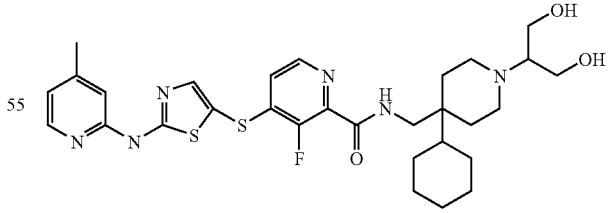

Following the procedure described for example 66, N-((4-cyclohexylpiperidin-4-yl)methyl)-3-fluoro-4-(2-(4-methylpyridin-2-ylamino)thiazol-5-ylthio)picolinamide (intermediate A in synthesis of example 53) was converted into the title compound. LC/MS (M+H)$^+$: 615. Ret. time: 1.62 min. (Condition L); analytical HPLC Ret. time: 17.14 min (Condition N).

EXAMPLE 68

N-((1-(1,3-dihydroxypropan-2-O-4-(5-methylisoxazol-3-yl)piperidin-4-yl)methyl)-3-fluoro-4-(2-(4-methylpyridin-2-ylamino)thiazol-5-ylthio)picolinamide

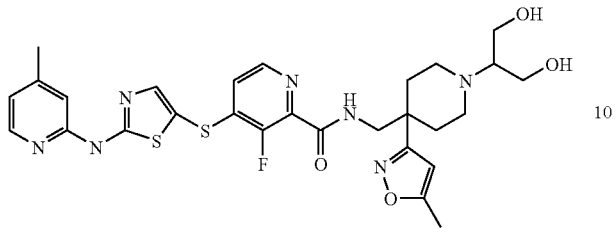

Following the procedure described for example 66, 3-fluoro-N-((4-(5-methylisoxazol-3-yl)piperidin-4-yl)methyl)-4-(2-(4-methylpyridin-2-ylamino)thiazol-5-ylthio)picolinamide (intermediate B in synthesis of example 54) was converted into the title compound. LC/MS (M+H)⁺: 614. Ret. time: 1.30 min. (Condition L); analytical HPLC Ret. time: 15.04 min (Condition N).

EXAMPLE 69

(S)—N-((1-(((2,2-dimethyl-1,3-dioxolan-4-yl)methyl)-4-(pyridin-3-yl)piperidin-4-yl)methyl)-3-fluoro-4-(2-(4-methylpyridin-2-ylamino)thiazol-5-ylthio)picolinamide

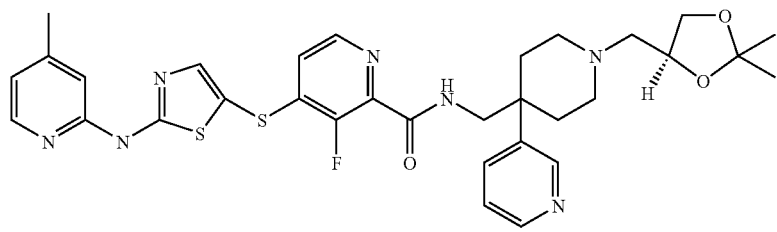 [SMILES: Cc1ccnc(Nc2ncc(Sc3ccnc(C(=O)NCC4(c5cccnc5)CCN(C[C@H]5COC(C)(C)O5)CC4)c3F)s2)c1]

3-fluoro-4-(2-(4-methylpyridin-2-ylamino)thiazol-5-ylthio)-N-((4-(pyridin-3-yl)piperidin-4-yl)methyl)picolinamide (compound example 48, 50 mg, crude free base, ~0.09 mmol) was dissolved in 3 ml MeOH+3 ml DMF. The pH was adjusted to ~4 by addition of acetic acid (1 drop) (alternatively, sodium acetate is added if starting material was TFA salt). Trimethylorthoformate (0.25 ml) was added, followed by (R)-2,2-dimethyl-1,3-dioxolane-4-carbaldehyde (65 mg, 0.5 mmol). The mixture was stirred at room temperature for 5 minutes, then NaBH₃CN (35 mg, 0.7 mmol) was added and the mixture stirred at room temperature for 30 minutes. The crude reaction mixture was filtered, rinsed with methanol, eluted with 2 M solution of ammonia in methanol and evaporated. The crude product was purified by prep HPLC (C-18 reversed phase column, water/acetonitrile gradient, buffered with 10 mM NH₄OAc). Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. 1.00 N HCl were added and the title compound was isolated as the mono-HCl salt by evaporation. LC/MS (M+H)⁺: 650. Ret. time: 1.17 min. (Condition G); analytical HPLC Ret. time: 5.26 min (Condition H).

EXAMPLE 70

(S)—N-((1-(((2,2-dimethyl-1,3-dioxolan-4-yl)methyl)-4-(pyridin-2-yl)piperidin-4-yl)methyl)-3-fluoro-4-(2-(4-methylpyridin-2-ylamino)thiazol-5-ylthio)picolinamide

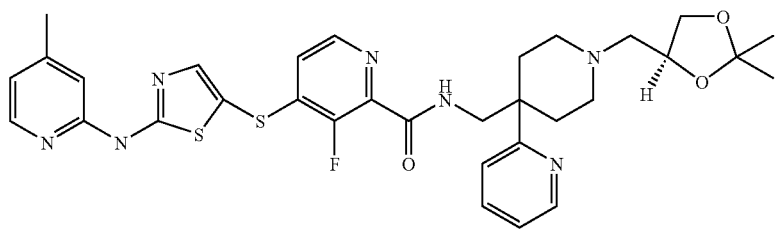 [SMILES: Cc1ccnc(Nc2ncc(Sc3ccnc(C(=O)NCC4(c5ccccn5)CCN(C[C@H]5COC(C)(C)O5)CC4)c3F)s2)c1]

Following the procedure described for example 69, 3-fluoro-4-(2-(4-methylpyridin-2-ylamino)thiazol-5-ylthio)-N-((4-(pyridin-2-yl)piperidin-4-yl)methyl)picolinamide (compound example 47) was converted into the title compound. LC/MS (M+H)⁺: 650. Ret. time: 1.25 min. (Condition G); analytical HPLC Ret. time: 5.40 min (Condition H).

EXAMPLE 71

(S)—N-((1-(2,3-dihydroxypropyl)-4-(pyridin-2-yl)piperidin-4-yl)methyl)-3-fluoro-4-(2-(4-methylpyridin-2-ylamino)thiazol-5-ylthio)picolinamide

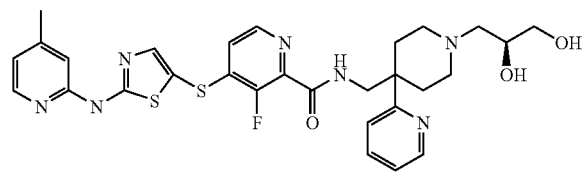

(S)—N-((1-((2,2-dimethyl-1,3-dioxolan-4-yl)methyl)-4-(pyridin-2-yl)piperidin-4-yl)methyl)-3-fluoro-4-(2-(4-methylpyridin-2-ylamino)thiazol-5-ylthio)picolinamide (compound example 70) was dissolved in 3 ml methanol and 1 ml aqueous 1 N HCl. The solution was stirred overnight at room temperature, then filtered through a cartridge filled with strong cation exchange resin, rinsed with methanol, eluted with 2 M solution of ammonia in methanol and evaporated. The crude product was purified by prep HPLC (C-18 reversed phase column, water/acetonitrile gradient, buffered with 10 mM NH₄OAc or water/methanol gradient, buffered with 0.1% TFA). Product containing fractions were filtered through a cartridge filled with cation exchange resin, rinsed with methanol, eluted with 2 M solution of ammonia in methanol and evaporated. The residue was dissolved in methanol, 1.0 equiv. aq. 1.00 N HCl were added and the title compound was isolated as the mono-HCl salt by evaporation. LC/MS (M+H)⁺: 610. Ret. time: 1.21 min. (Condition G); analytical HPLC Ret. time: 4.65 min (Condition H).

EXAMPLE 72

(S)—N-((1-(2,3-dihydroxypropyl)-4-(pyridin-3-yl)piperidin-4-yl)methyl)-3-fluoro-4-(2-(4-methylpyridin-2-ylamino)thiazol-5-ylthio)picolinamide

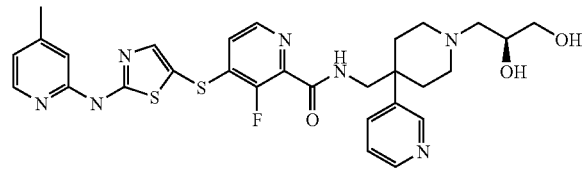

Following the procedure described for example 71, (S)—N-((1-((2,2-dimethyl-1,3-dioxolan-4-yl)methyl)-4-(pyridin-3-yl)piperidin-4-yl)methyl)-3-fluoro-4-(2-(4-methylpyridin-2-ylamino)thiazol-5-ylthio)picolinamide (compound example 70) converted into the title compound. LC/MS (M+H)⁺: 610. Ret. time: 1.13 min. (Condition G); analytical HPLC Ret. time: 4.27 min (Condition H).

EXAMPLE 73

(S)—N-((1-(2,3-dihydroxypropyl)-4-(pyridin-4-yl)piperidin-4-yl)methyl)-3-fluoro-4-(2-(4-methylpyridin-2-ylamino)thiazol-5-ylthio)picolinamide

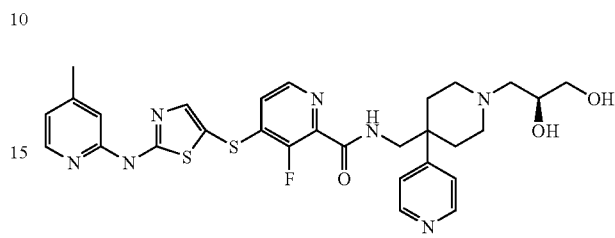

3-Fluoro-4-(2-(4-methylpyridin-2-ylamino)thiazol-5-ylthio)-N-((4-(pyridin-4-yl)piperidin-4-yl)methyl)picolinamide (compound example 45, 50 mg, 0.093 mmol) was dissolved in 5 ml MeOH+5 ml THF. The pH was adjusted to ~4 by addition of acetic acid (5 ul) (alternatively, sodium acetate is added if starting material was TFA salt). Trimethylorthoformate (1 ml) was added, followed by (R)-2,2-dimethyl-1,3-dioxolane-4-carbaldehyde (65 mg, 0.5 mmol). The mixture was stirred at room temperature for 5 minutes, then NaBH₃CN (35 mg, 0.7 mmol) was added and the mixture stirred at room temperature for 30 minutes. The crude reaction mixture was filtered, rinsed with methanol, eluted with 2 M solution of ammonia in methanol and evaporated. The crude product (a mixture of the diol title compound and it's acetonide) was dissolved in 5 ml methanol and 1 ml 1.0 N aq. HCl and stirred at room temperature for 18 hours, then filtered through a cartridge filled with strong cation exchange resin, rinsed with methanol, eluted with 2 M solution of ammonia in methanol and evaporated. The crude product was purified by prep HPLC (C-18 reversed phase column, water/acetonitrile gradient, buffered with 10 mM NH₄OAc or water/methanol gradient, buffered with 0.1% TFA). Product containing fractions were filtered through a cartridge filled with cation exchange resin, rinsed with methanol, eluted with 2 M solution of ammonia in methanol and evaporated. The residue was dissolved in methanol, 1.0 equiv. aq. 1.00 N HCl were added and the title compound isolated as it's mono-HCl salt by evaporation. LC/MS (M+H)⁺: 610. Ret. time: 1.18 min. (Condition M); analytical HPLC Ret. time: 8.43 min (Condition N).

EXAMPLE 74

(S)—N-((4-cyclohexyl-1-(2,3-dihydroxypropyl)piperidin-4-yl)methyl)-3-fluoro-4-(2-(4-methylpyridin-2-ylamino)thiazol-5-ylthio)picolinamide

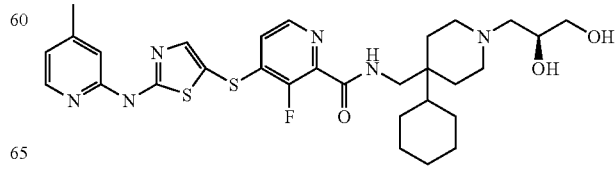

Following the procedure described for example 73, N-((4-cyclohexylpiperidin-4-yl)methyl)-3-fluoro-4-(2-(4-methylpyridin-2-ylamino)thiazol-5-ylthio)picolinamide (intermediate A from example 53) was converted into the title compound. LC/MS (M+H)+: 615. Ret. time: 1.59 min. (Condition L); analytical HPLC Ret. time: 13.57 min (Condition N).

EXAMPLE 75

(S)—N-((1-(2,3-dihydroxypropyl)-4-(5-methylisoxazol-3-yl)piperidin-4-yl)methyl)-3-fluoro-4-(2-(4-methylpyridin-2-ylamino)thiazol-5-ylthio)picolinamide

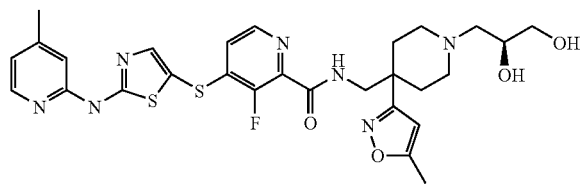 [SMILES: Cc1ccnc(Nc2ncc(Sc3ccnc(C(=O)NCC4(c5cc(C)on5)CCN(C[C@H](O)CO)CC4)c3F)s2)c1]

Following the procedure described for example 73, 3-fluoro-N-((4-(5-methylisoxazol-3-yl)piperidin-4-yl)methyl)-4-(2-(4-methylpyridin-2-ylamino)thiazol-5-ylthio)picolinamide (intermediate B from example 54) was converted into the title compound. LC/MS (M+H)+: 614. Ret. time: 1.31 min. (Condition L); analytical HPLC Ret. time: 14.91 min (Condition N).

EXAMPLE 76

(S)—N-((1-(2,3-dihydroxypropyl)-4-(4-fluorophenyl)piperidin-4-yl)methyl)-3-fluoro-4-(2-(4-methylpyridin-2-ylamino)thiazol-5-ylthio)picolinamide

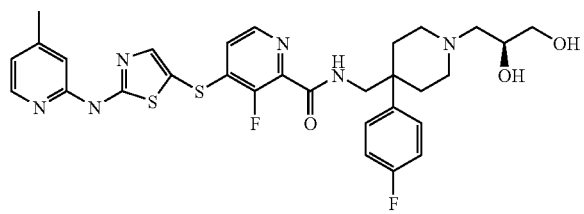 [SMILES: Cc1ccnc(Nc2ncc(Sc3ccnc(C(=O)NCC4(c5ccc(F)cc5)CCN(C[C@H](O)CO)CC4)c3F)s2)c1]

Following the procedure described for example 73, 3-fluoro-N-((4-(4-fluorophenyl)piperidin-4-yl)methyl)-4-(2-(4-methylpyridin-2-ylamino)thiazol-5-ylthio)picolinamide (intermediate B from example 51) was converted into the title compound. LC/MS (M+H)+: 627. Ret. time: 1.43 min. (Condition L); analytical HPLC Ret. time: 16.43 min (Condition N).

EXAMPLE 77

(S)—N-((4-(2,4-difluorophenyl)-1-(2,3-dihydroxypropyl)piperidin-4-yl)methyl)-3-fluoro-4-(2-(4-methylpyridin-2-ylamino)thiazol-5-ylthio)picolinamide

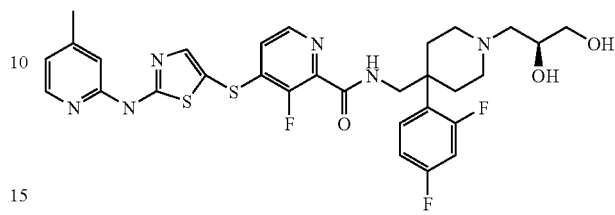

Following the procedure described for example 73, N-((4-(2,4-difluorophenyl)piperidin-4-yl)methyl)-3-fluoro-4-(2-(4-methylpyridin-2-ylamino)thiazol-5-ylthio)picolinamide (intermediate B from example 52) was converted into the title compound. LC/MS (M+H)+: 645. Ret. time: 1.44 min. (Condition L); analytical HPLC Ret. time: 15.98 min (Condition N).

EXAMPLE 78

(S)—N-((1-(2,3-dihydroxypropyl)-4-phenylpiperidin-4-yl)methyl)-3-fluoro-4-(2-(4-methylpyridin-2-ylamino)thiazol-5-ylthio)picolinamide

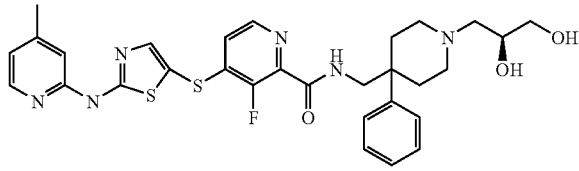

Following the procedure described for example 73, 3-Fluoro-4-(2-(4-methylpyridin-2-ylamino)thiazol-5-ylthio)-N-((4-phenylpiperidin-4-yl)methyl)picolinamide (compound example 11) was converted into the title compound. LC/MS (M+H)+: 609. Ret. time: 1.37 min. (Condition M); analytical HPLC Ret. time: 10.73 min (Condition N).

EXAMPLE 79

N-((4-cyclohexyl-1-(2-hydroxy-2-methylpropyl)piperidin-4-yl)methyl)-3-fluoro-4-(2-(4-methylpyridin-2-ylamino)thiazol-5-ylthio)picolinamide

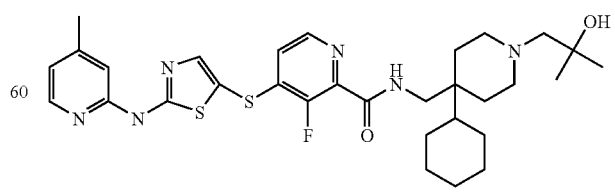

Following the procedure described for example 35, N-((4-cyclohexylpiperidin-4-yl)methyl)-3-fluoro-4-(2-(4-methylpyridin-2-ylamino)thiazol-5-ylthio)picolinamide (intermediate A from example 53) was converted into the title compound. LC/MS (M+H)+: 613. Ret. time: 1.62 min. (Condition L); analytical HPLC Ret. time: 19.25 min (Condition N).

EXAMPLE 80

N-((4-(2,4-difluorophenyl)-1-(2-hydroxy-2-methylpropyl)piperidin-4-yl)methyl)-3-fluoro-4-(2-(4-methylpyridin-2-ylamino)thiazol-5-ylthio)picolinamide

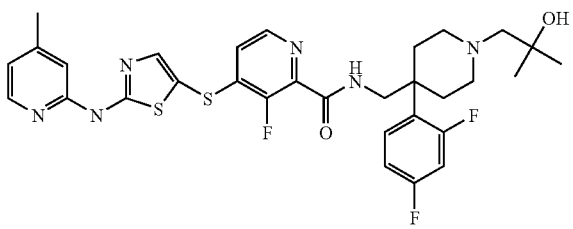 [SMILES: Cc1ccnc(Nc2ncc(Sc3ccnc(C(=O)NCC4(c5ccc(F)cc5F)CCN(CC(C)(C)O)CC4)c3F)s2)c1]

Following the procedure described for example 35, N-((4-(2,4-difluorophenyl)piperidin-4-yl)methyl)-3-fluoro-4-(2-(4-methylpyridin-2-ylamino)thiazol-5-ylthio)picolinamide (intermediate B from example 52) was converted into the title compound. LC/MS (M+H)+: 643. Ret. time: 1.48 min. (Condition L); analytical HPLC Ret. time: 17.59 min (Condition N).

EXAMPLE 81

Methyl 4-((3-fluoro-4-(2-(4-methylpyridin-2-ylamino)thiazol-5-ylthio)picolinamido)methyl)-4-phenylpiperidine-1-carboxylate

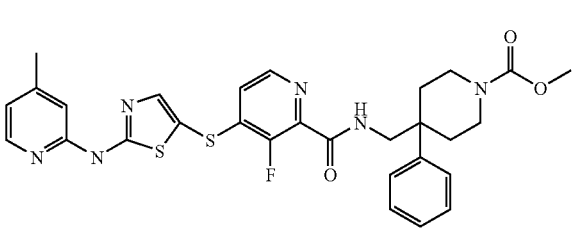

3-Fluoro-4-(2-(4-methylpyridin-2-ylamino)thiazol-5-ylthio)-N-((4-phenylpiperidin-4-yl)methyl)picolinamide (compound example 11, 50 mg) was dissolved in 1 ml methanol and 0.05 ml diisopropylethylamine 0.05 ml methyl chloroformate was added slowly and the mixture stirred at room temperature overnight. Volatiles were evaporated using under a stream of nitrogen and the crude product was purified by prep HPLC (C-18 reversed phase column, water/acetonitrile gradient, buffered with 10 mM NH4OAc or water/methanol gradient, buffered with 0.1% TFA). Product containing fractions were filtered through a cartridge filled with cation exchange resin (MCX from Waters or STRATA X-C from Phenomenex), rinsed with methanol, eluted with 2 M solution of ammonia in methanol and evaporated. The residue was dissolved in methanol, 1.0 equiv. aq. 1.00 N HCl were added and the title compound isolated as it's mono-HCl salt by evaporation. (14.5 mg, 25%). LC/MS (M+H)+: 593. Ret. time: 1.95 min. (Condition I); analytical HPLC Ret. time: 8.95 min (Condition H).

EXAMPLE 82

2-Methoxyethyl 4-((3-fluoro-4-(2-(4-methylpyridin-2-ylamino)thiazol-5-ylthio)picolinamido)methyl)-4-phenylpiperidine-1-carboxylate

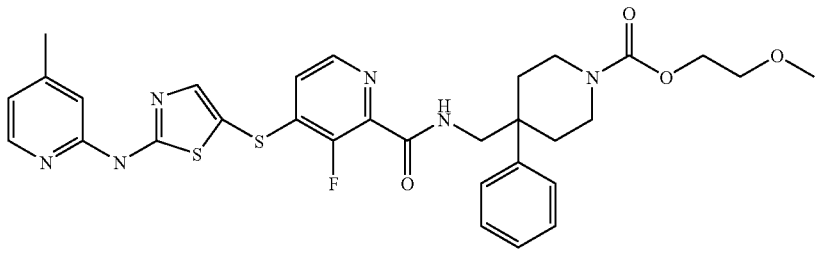

Following the procedure given for example 81, 3-fluoro-4-(2-(4-methylpyridin-2-ylamino)thiazol-5-ylthio)-N-((4-phenylpiperidin-4-yl)methyl)picolinamide (compound example 11) was reacted with 2-methoxyethyl chloroformate to give the title compound. LC/MS (M+H)+: 637. Ret. time: 1.91 min. (Condition I); analytical HPLC Ret. time: 8.66 min (Condition H).

EXAMPLE 83

Methyl 4-((3-fluoro-4-(2-(4-methylpyridin-2-ylamino)thiazol-5-ylthio)picolinamido)methyl)-4-(pyridin-4-yl)piperidine-1-carboxylate

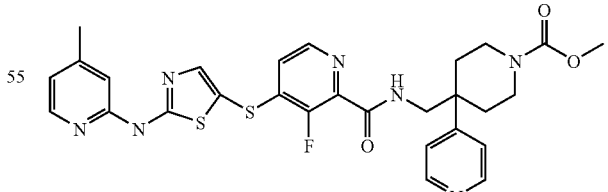

Following the procedure given for example 81, 3-fluoro-4-(2-(4-methylpyridin-2-ylamino)thiazol-5-ylthio)-N-((4-(pyridin-4-yl)piperidin-4-yl)methyl)picolinamide (compound example 45) was reacted with methyl chloroformate to give the title compound. LC/MS (M+H)+: 594. Ret. time: 1.32 min. (Condition I); analytical HPLC Ret. time: 5.23 min (Condition H).

EXAMPLE 84

2-Methoxyethyl 4-((3-fluoro-4-(2-(4-methylpyridin-2-ylamino)thiazol-5-ylthio)picolinamido)methyl)-4-(pyridin-4-yl)piperidine-1-carboxylate

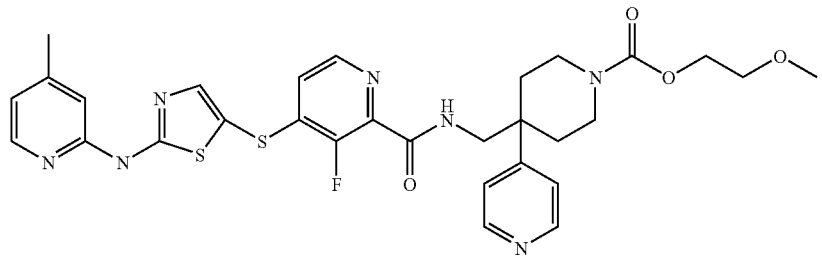 [SMILES: COCCOC(=O)N1CCC(CNC(=O)c2nccc(Sc3cnc(Nc4cc(C)ccn4)s3)c2F)(c2ccncc2)CC1]

Following the procedure given for example 81, 3-fluoro-4-(2-(4-methylpyridin-2-ylamino)thiazol-5-ylthio)-N-((4-(pyridin-4-yl)piperidin-4-yl)methyl)picolinamide (compound example 45) was reacted with 2-methoxyethyl chloroformate to give the title compound. LC/MS (M+H)+: 638. Ret. time: 1.31 min. (Condition I); analytical HPLC Ret. time: 5.30 min (Condition H).

EXAMPLE 85

Methyl 4-(3,4-dichlorophenyl)-4-((3-fluoro-4-(2-(4-methylpyridin-2-ylamino)thiazol-5-ylthio)picolinamido)methyl)piperidine-1-carboxylate

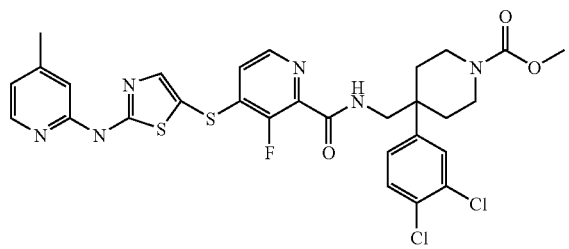 [SMILES: COC(=O)N1CCC(CNC(=O)c2nccc(Sc3cnc(Nc4cc(C)ccn4)s3)c2F)(c2ccc(Cl)c(Cl)c2)CC1]

Following the procedure given for example 81, N-((4-(3,4-dichlorophenyl)piperidin-4-yl)methyl)-3-fluoro-4-(2-(4-methylpyridin-2-ylamino)thiazol-5-ylthio)picolinamide (compound example 48) was reacted with methyl chloroformate to give the title compound. LC/MS (M+H)+: 661. Ret. time: 2.09 min. (Condition I); analytical HPLC Ret. time: 10.35 min (Condition H).

EXAMPLE 86

2-methoxyethyl 4-(3,4-dichlorophenyl)-4-((3-fluoro-4-(2-(4-methylpyridin-2-ylamino)thiazol-5-ylthio)picolinamido)methyl)piperidine-1-carboxylate

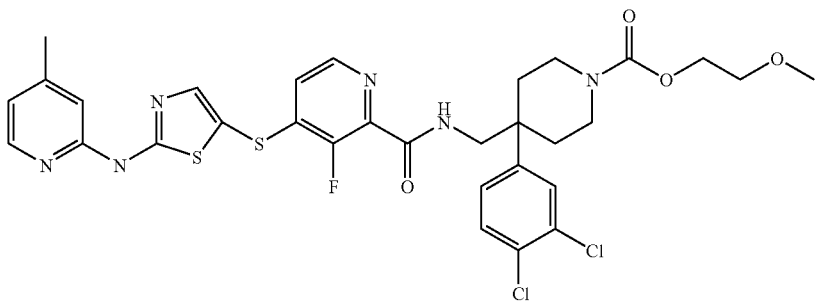 [SMILES: COCCOC(=O)N1CCC(CNC(=O)c2nccc(Sc3cnc(Nc4cc(C)ccn4)s3)c2F)(c2ccc(Cl)c(Cl)c2)CC1]

Following the procedure given for example 81, N-((4-(3,4-dichlorophenyl)piperidin-4-yl)methyl)-3-fluoro-4-(2-(4-methylpyridin-2-ylamino)thiazol-5-ylthio)picolinamide (compound example 48) was reacted with 2-methoxyethyl chloroformate to give the title compound. LC/MS (M+H)+: 705. Ret. time: 2.06 min. (Condition I); analytical HPLC Ret. time: 9.77 min (Condition H).

EXAMPLE 87

Methyl 4-((3-fluoro-4-(2-(4-methylpyridin-2-ylamino)thiazol-5-ylthio)picolinamido)methyl)-4-(pyridin-2-yl)piperidine-1-carboxylate

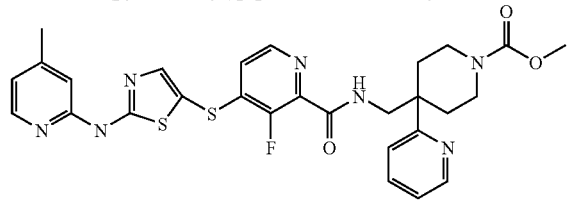 [SMILES: COC(=O)N1CCC(CNC(=O)c2nccc(Sc3cnc(Nc4cc(C)ccn4)s3)c2F)(c2ccccn2)CC1]

Following the procedure given for example 81, 3-fluoro-4-(2-(4-methylpyridin-2-ylamino)thiazol-5-ylthio)-N-((4-(pyridin-2-yl)piperidin-4-yl)methyl)picolinamide (compound example 47) was reacted with methyl chloroformate to give the title compound. LC/MS (M+H)+: 594. Ret. time: 1.41 min. (Condition I); analytical HPLC Ret. time: 5.73 min (Condition H).

EXAMPLE 88

2-Methoxyethyl 4-((3-fluoro-4-(2-(4-methylpyridin-2-ylamino)thiazol-5-ylthio)picolinamido)methyl)-4-(pyridin-2-yl)piperidine-1-carboxylate

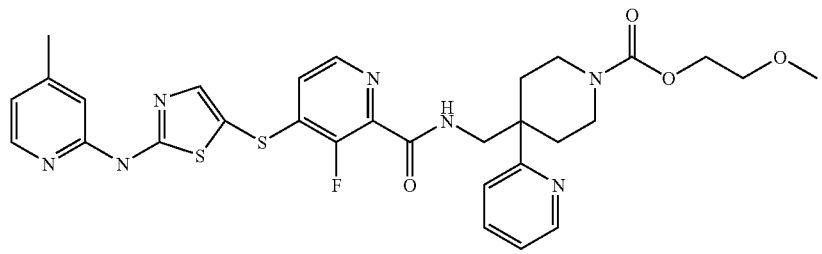 [SMILES: COCCOC(=O)N1CCC(CNC(=O)c2nccc(Sc3cnc(Nc4cc(C)ccn4)s3)c2F)(c2ccccn2)CC1]

Following the procedure given for example 81, 3-fluoro-4-(2-(4-methylpyridin-2-ylamino)thiazol-5-ylthio)-N-((4-(pyridin-2-yl)piperidin-4-yl)methyl)picolinamide (compound example 47) was reacted with 2-methoxyethyl chloroformate to give the title compound. LC/MS (M+H)+: 638. Ret. time: 1.42 min. (Condition I); analytical HPLC Ret. time: 5.63 min (Condition H).

EXAMPLE 89

N-((1-(dimethylcarbamoyl)-4-phenylpiperidin-4-yl)methyl)-3-fluoro-4-(2-(4-methylpyridin-2-ylamino)thiazol-5-ylthio)picolinamide

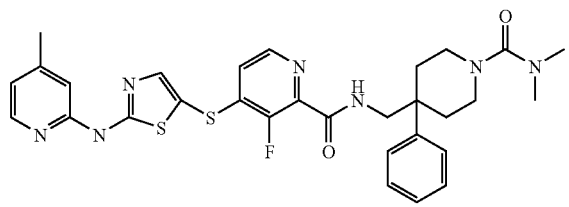 [SMILES: Cc1ccnc(Nc2ncc(Sc3ccnc(C(=O)NCC4(c5ccccc5)CCN(C(=O)N(C)C)CC4)c3F)s2)c1]

Following the procedure given for example 81, 3-fluoro-4-(2-(4-methylpyridin-2-ylamino)thiazol-5-ylthio)-N-((4-phenylpiperidin-4-yl)methyl)picolinamide (compound example 11) was reacted with dimethylcarbamic chloride to give the title compound. LC/MS (M+H)+: 606. Ret. time: 1.53 min. (Condition G); analytical HPLC Ret. time: 7.53 min (Condition H).

EXAMPLE 90

3-Fluoro-4-(2-(4-methylpyridin-2-ylamino)thiazol-5-ylthio)-N-((1-(morpholine-4-carbonyl)-4-phenylpiperidin-4-yl)methyl)picolinamide

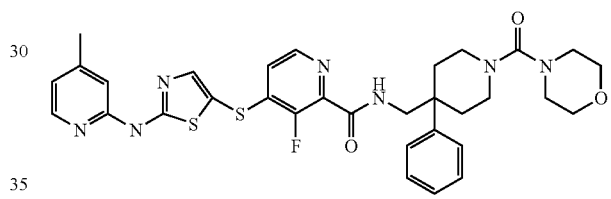

Following the procedure given for example 81, 3-fluoro-4-(2-(4-methylpyridin-2-ylamino)thiazol-5-ylthio)-N-((4-phenylpiperidin-4-yl)methyl)picolinamide (compound example 11) was reacted with morpholine-4-carbonyl chloride to give the title compound. LC/MS (M+H)+: 648. Ret. time: 1.48 min. (Condition G); analytical HPLC Ret. time: 7.35 min (Condition H).

EXAMPLE 91

3-Fluoro-N-((1-(4-methylpiperazine-1-carbonyl)-4-phenylpiperidin-4-yl)methyl)-4-(2-(4-methylpyridin-2-ylamino)thiazol-5-ylthio)picolinamide

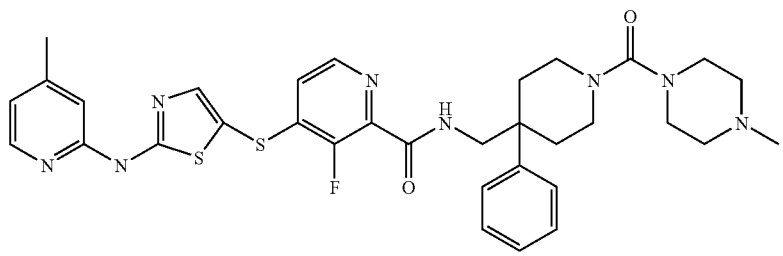 [SMILES: Cc1ccnc(Nc2ncc(Sc3ccnc(C(=O)NCC4(c5ccccc5)CCN(C(=O)N5CCN(C)CC5)CC4)c3F)s2)c1]

Following the procedure given for example 81, 3-fluoro-4-(2-(4-methylpyridin-2-ylamino)thiazol-5-ylthio)-N-((4-phenylpiperidin-4-yl)methyl)picolinamide (compound example 11) was reacted with 4-methylpiperazine-1-carbonyl chloride to give the title compound. LC/MS (M+H)+: 661. Ret. time: 1.46 min. (Condition G); analytical HPLC Ret. time: 6.16 min (Condition H).

EXAMPLE 92

N-((1-(4-chloro-3-sulfamoylbenzoyl)-4-phenylpiperidin-4-yl)methyl)-3-fluoro-4-(2-(4-methylpyridin-2-ylamino)thiazol-5-ylthio)picolinamide

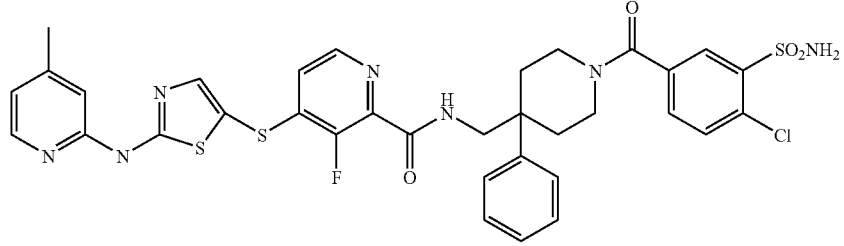 [SMILES: Cc1ccnc(Nc2ncc(Sc3ccnc(C(=O)NCC4(c5ccccc5)CCN(C(=O)c5ccc(Cl)c(S(N)(=O)=O)c5)CC4)c3F)s2)c1]

50 mg of 3-fluoro-4-(2-(4-methylpyridin-2-ylamino)thiazol-5-ylthio)-N-((4-phenylpiperidin-4-yl)methyl)picolinamide (compound example 11) was mixed with 0.05 ml diisopropylethylamine and 1 ml DMF. 24 mg of 4-chloro-3-sulfamoylbenzoic acid and 40 mg HATU were added and the mixture stirred at room temperature overnight. LC/MS showed completed consumption of compound II. Volatiles were evaporated under a stream of nitrogen and the crude product re-dissolved in 2 ml 5% TFA/MeOH and purified by prep HPLC (C-18 reversed phase column, water/MeOH gradient, buffered with 0.1% TFA). Alternatively a water/acetonitrile gradient, buffered with 10 mM NH4OAc can be used. Product containing fractions were filtered through a cartridge filled with cation exchange resin, rinsed with methanol, eluted with 2 M solution of ammonia in methanol and evaporated. The residue was dissolved in methanol, 1.0 equiv. aq. 1.00 N HCl were added and the title compound was isolated as the mono-HCl salt by evaporation. LC/MS (M+H)+: 752. Ret. time: 2.12 min. (Condition J); analytical HPLC Ret. time: 13.29 min (Condition K).

EXAMPLE 93

N-((1-(2-chloro-4-fluoro-5-sulfamoylbenzoyl)-4-phenylpiperidin-4-yl)methyl)-3-fluoro-4-(2-(4-methylpyridin-2-ylamino)thiazol-5-ylthio)picolinamide

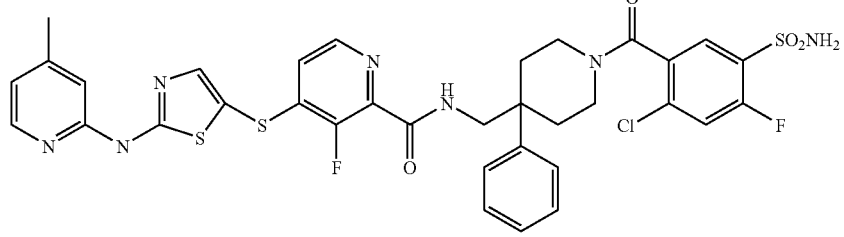

Following the procedure given for example 92, 3-fluoro-4-(2-(4-methylpyridin-2-ylamino)thiazol-5-ylthio)-N-((4-phenylpiperidin-4-yl)methyl)picolinamide (compound example 11) was reacted with 2-chloro-4-fluoro-5-sulfamoylbenzoic acid to give the title compound. LC/MS (M+H)+: 770. Ret. time: 2.17 min. (Condition J); analytical HPLC Ret. time: 12.91 min (Condition K).

EXAMPLE 94

N-((1-(1-aminocyclopropanecarbonyl)-4-phenylpiperidin-4-yl)methyl)-3-fluoro-4-(2-(4-methylpyridin-2-ylamino)thiazol-5-ylthio)picolinamide

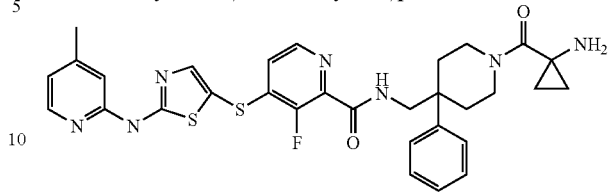

40 mg of 3-fluoro-4-(2-(4-methylpyridin-2-ylamino)thiazol-5-ylthio)-N-((4-phenylpiperidin-4-yl)methyl)picolinamide (compound example 11) was mixed with 0.05 ml diisopropylethylamine and 1 ml DMF. 25 mg of 1-(tert-butoxycarbonylamino)cyclopropanecarboxylic acid was added followed by 40 mg O-(7-azabenzotriazol-1-yl)-N,N,N',N'-tetramethyluronium hexafluorophosphate. The mixture was then stirred at r.t. overnight. LC/MS showed completed conversion. Volatiles were evaporated under a stream of nitrogen and the crude product re-dissolved in 2 ml 5% TFA/MeOH and purified by prep HPLC (C-18 reversed phase column, water/MeOH gradient, buffered with 0.1% TFA). Alternatively a water/acetonitrile gradient, buffered with 10 mM NH4OAc can be used. Product containing fractions were concentrated by Speedvac, re-dissolved in 2 ml dichloromethane+0.5 ml TFA and stirred for 1 hour to remove the Boc protecting group. Volatiles were evaporated under a stream of nitrogen. The product was dissolved in Methanol and filtered through a MCX cartridge (Waters, strong cation exchange resin, 20 cc, 1 g), which was washed with MeOH, then eluted with 2N ammonia in MeOH and concentrated under nitrogen stream. The salt-free product was treated with 1 equiv. of 1N HCl to give the mono-HCl salt of the title compound. (9.9 mg, 20%). LC/MS (M+H)+: 618. Ret. time: 1.35 min. (Condition G); analytical HPLC Ret. time: 6.58 min (Condition Q).

EXAMPLE 95

N-((1-(2-amino-2-methylpropanoyl)-4-phenylpiperidin-4-yl)methyl)-3-fluoro-4-(2-(4-methylpyridin-2-ylamino)thiazol-5-ylthio)picolinamide

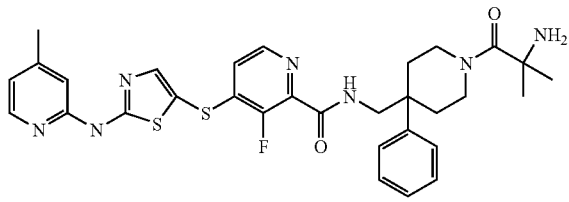 [SMILES: Cc1ccnc(Nc2ncc(Sc3ccnc(C(=O)NCC4(c5ccccc5)CCN(C(=O)C(C)(C)N)CC4)c3F)s2)c1]

Following the procedure given for example 94, 3-fluoro-4-(2-(4-methylpyridin-2-ylamino)thiazol-5-ylthio)-N-((4-phenylpiperidin-4-yl)methyl)picolinamide (compound example 11) was reacted with 2-(tert-butoxycarbonylamino)-2-methylpropanoic acid to give the title compound. LC/MS (M+H)+: 620. Ret. time: 1.35 min. (Condition G); analytical HPLC Ret. time: 6.55 min (Condition Q).

EXAMPLE 96

(S)-3-amino-4-(4-((3-fluoro-4-(2-(4-methylpyridin-2-ylamino)thiazol-5-ylthio)picolinamido)methyl)-4-phenylpiperidin-1-yl)-4-oxobutanoic acid

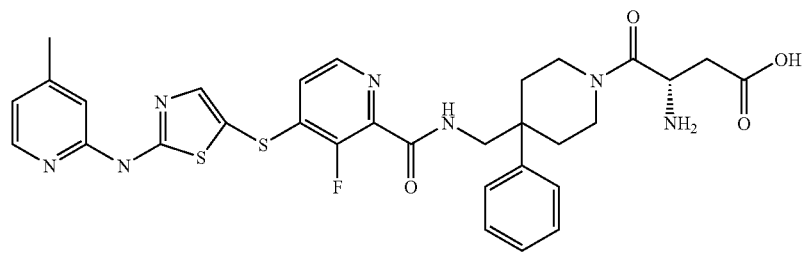 [SMILES: Cc1ccnc(Nc2ncc(Sc3ccnc(C(=O)NCC4(c5ccccc5)CCN(C(=O)[C@@H](N)CC(=O)O)CC4)c3F)s2)c1]

Following the procedure given for example 94, 3-fluoro-4-(2-(4-methylpyridin-2-ylamino)thiazol-5-ylthio)-N-((4-phenylpiperidin-4-yl)methyl)picolinamide (compound example 11) was reacted with (S)-2-(tert-butoxycarbonylamino)succinic acid give the title compound. LC/MS (M+H)+: 650. Ret. time: 1.12 min. (Condition G); analytical HPLC Ret. time: 6.33 min (Condition Q).

EXAMPLE 97

(S)—N-((1-(2-amino-3-methylbutanoyl)-4-phenylpiperidin-4-yl)methyl)-3-fluoro-4-(2-(4-methylpyridin-2-ylamino)thiazol-5-ylthio)picolinamide

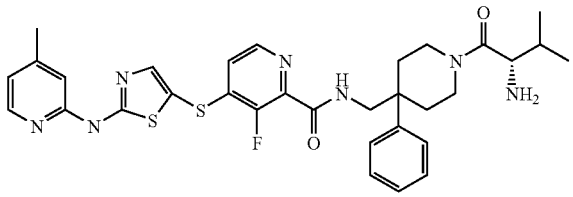 [SMILES: Cc1ccnc(Nc2ncc(Sc3ccnc(C(=O)NCC4(c5ccccc5)CCN(C(=O)[C@@H](N)C(C)C)CC4)c3F)s2)c1]

Following the procedure given for example 94, 3-fluoro-4-(2-(4-methylpyridin-2-ylamino)thiazol-5-ylthio)-N-((4-phenylpiperidin-4-yl)methyl)picolinamide (compound example 11) was reacted with (S)-2-(tert-butoxycarbonylamino)-3-methylbutanoic acid give the title compound. LC/MS (M+H)+: 634. Ret. time: 1.42 min. (Condition G); analytical HPLC Ret. time: 6.58 min (Condition Q).

The invention claimed is:
1. The compound according to formula III

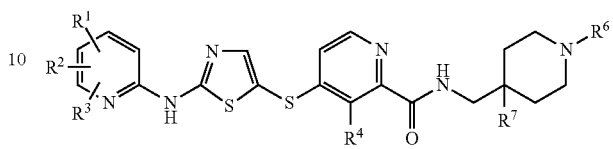

(III)

wherein
$R^1$, $R^2$ and $R^3$ are independently selected from the group consisting of hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, nitro, carboxy, alkoxycarbonyl, alkylcarbonyloxy, carbamoyl, substituted carbamoyl, alkenyl, substituted alkenyl, alkynyl, substituted alkynyl, alkylcarbonyl, or
$R^1$ and $R^2$ or $R^2$ and $R^3$ can be taken together to form an optionally substituted carbocyclic or heterocyclic ring;

$R^4$ is hydrogen, alkyl, substituted alkyl, hydroxy, cyano or halogen;

$R^6$ and $R^7$ are independently selected from the group consisting of hydrogen, alkyl, substituted alkyl, aryl, substituted aryl, alkylidene, substituted alkylidene, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, cyanoalkyl, sulfonamide, substituted sulfonamide, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, alkylaminocarbonyl, —COOalkyl, —COaminoalkyl, —COalkyl, —COcycloalkyl, —COheteroaryl and —CO substituted heteroaryl;

or a pharmaceutically acceptable salt or a stereoisomer thereof.

2. The compound according to formula IV

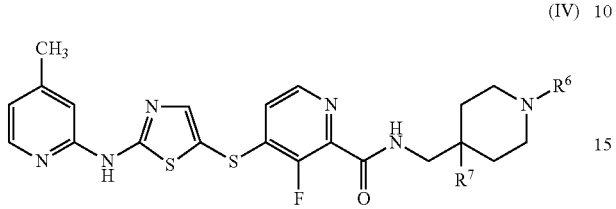

(IV)

wherein:

R$^6$ and R$^7$ are independently selected from the group consisting of hydrogen, alkyl, substituted alkyl, aryl, substituted aryl, alkylidene, substituted alkylidene, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, cyanoalkyl, sulfonamide, substituted sulfonamide, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, alkylaminocarbonyl, —COOalkyl, —COaminoalkyl, —COalkyl, —COcycloalkyl, —COheteroaryl and —CO substituted heteroaryl;

or a pharmaceutically acceptable salt or a stereoisomer thereof.

3. A pharmaceutical composition comprising a pharmaceutically acceptable carrier and one or more compounds of claim 1 or pharmaceutically acceptable salts or stereoisomers thereof.

4. A pharmaceutical composition comprising a pharmaceutically acceptable carrier and one or more compounds of claim 2 or pharmaceutically acceptable salts or stereoisomers thereof.

* * * * *